US007351535B2

(12) United States Patent
Lawn et al.

(10) Patent No.: US 7,351,535 B2
(45) Date of Patent: Apr. 1, 2008

(54) COMPOSITIONS AND METHODS FOR INCREASING CHOLESTEROL EFFLUX AND RAISING HDL USING ATP BINDING CASSETTE TRANSPORTER PROTEIN ABC1

(75) Inventors: Richard M Lawn, San Francisco, CA (US); David Wade, Palo Alto, CA (US); Michael Garvin, San Francisco, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 329 days.

(21) Appl. No.: 10/920,989

(22) Filed: Aug. 18, 2004

(65) Prior Publication Data

US 2005/0009089 A1 Jan. 13, 2005

Related U.S. Application Data

(62) Division of application No. 09/596,141, filed on Jun. 16, 2000, now Pat. No. 6,821,774.

(60) Provisional application No. 60/166,573, filed on Nov. 19, 1999, provisional application No. 60/153,872, filed on Sep. 14, 1999, provisional application No. 60/140,264, filed on Jun. 18, 1999.

(51) Int. Cl.

| | |
|---|---|
| *C12Q 1/68* | (2006.01) |
| *C07H 21/04* | (2006.01) |
| *C12P 21/02* | (2006.01) |
| *C12N 1/21* | (2006.01) |
| *C12N 15/00* | (2006.01) |

(52) U.S. Cl. ........................ 435/6; 536/24.1; 536/24.5; 536/23.4; 435/69.1; 435/252.3; 435/320.1

(58) Field of Classification Search .................... 435/4, 435/6, 69.1, 183, 252.3, 320.1, 325; 536/23.2, 536/23.4, 24.1, 24.5

See application file for complete search history.

(56) References Cited

U.S. PATENT DOCUMENTS

2004/0137423 A1* 7/2004 Hayden et al. ................ 435/4

* cited by examiner

*Primary Examiner*—Rebecca Prouty
*Assistant Examiner*—Rosanne Kosson

(57) ABSTRACT

The present invention relates to novel ABC1 polypeptides and nucleic acid molecules encoding the same. The invention also relates to recombinant vectors, host cells, and compositions comprising ABC1 polynucleotides, as well as to methods for producing ABC1 polypeptides. The invention also relates to antibodies that bind specifically to ABC1 polypeptides. In addition, the invention relates to methods for increasing cholesterol efflux as well as to methods for increasing ABC1 expression and activity. The present invention further relates to methods for identifying compounds that modulate the expression of ABC1 and methods for detecting the comparative level of ABC1 polypeptides and polynucleotides in a mammalian subject. The present invention also provides kits and compositions suitable for screening compounds to determine the ABC1 expression modulating activity of the compound, as well as kits and compositions suitable to determine whether a compound modulates ABC1-dependent cholesterol efflux.

7 Claims, 10 Drawing Sheets

ABC1 gene 5' flanking region

```
1 GAATTCCTTGCTGGTGGCTCCACATGCACTTCCAGGGCCTGCTTGGCTCTTCTATGGGTCTGTCCTGAGTGTTGATAGAACCACTGATGTGAGTACCTGG
101 GCTTGAGCGTGGCCTGGAGATCCTGTTGACTGTAGCATGGAGGGGGCTTGTCAGCTGAATGTCTGTATGCAGGTGGTGGGAGTTCTGGAATATGATGGAG
201 CTGGAGGTGGGAAGAGAAGTAGGCTTGGGGCAGCTCTCTCATGCCACCTCATTCTGGCCAAAACTCAGGTCAAACTGTGAAGAGTCTAAATGTGAATCTG
301 CCCTTCAAGGTGGCTACAAAGGTATCTTTGTCAAGGTAGGAGACCTTGTGGCCTCCACGTGCACTTCCAGGGCCTGCTTGGCCTCTTCTACGGGTCTGTC
401 CTGAGTCTTCTATGAATCTCCCTTCAGGGCAGATTCATATTTAGACTCTTCACAGTTTGACCTGAGTTTTGGCCAGAATAAGGTGACATTTAGTTTGTTG
501 GCTTGATGAATGACTTAAATATTTAGACATATGGTGTGTAGGCCTGCATTCCTACTCTTGCCTTTTTTTTTGCCCCTCCAGTGTTTTGGGTAGTTTTGCT
601 CCCCCTACAGCCAAAGGCAAACAGATAAGTTGGAGGTCTGGAGTGGCTACATAATTTTACACGACTGCAATTCTCTGGCTGCACTTCACAAATGTATACA
701 AACTAAATACAAGTCCTGTGTTTTTATCACAGGGAGGCTGATCAATATAATGAAATTAAAAGGGGGCTGGTCCCATATTGTTCTGTGTTTTTGTTTGTTT
801 GTTTCTTTTTTTGTTTTTGTGGCCTCCTTCCTCTCAATTTATGAAGAGAAGCAGTAAGATGTTCCTCTCGGGTCCTCTGAGGGACCTGGGGAGCTCAGGC
901 TGGGAATCTCCAAGGCAGTAGGTCGCCTATCAAAAATCAAAGTCCAGGTTTGTGGGGGGAAAACAAAAGCAGCCCATTACCCAGAGGACTGTCCGCCTTC
1001 CCCTCACCCCAGCCTAGGCCTTTGAAAGGAAACAAAAGACAAGACAAAATGATTGGCGTCCTGAGGGAGATTCAGCCTAGAGCTCTCTCTCCCCCAATCC
1101 CTCCCTCCGGCTGAGGAAACTAACAAAGGAAAAAAAAATTGCGGAAAGCAGGATTTAGAGGAAGCAAATTCCACTGGTGCCCTTGGCTGCCGGGAACGTG
1201 GACTAGAGAGTCTGCGGCGCAGCCCCGAGCCCAGCGCTTCCCGCGCGTCTTAGGCCGGCGGGCCCGGGCGGGGGAAGGGGACGCAGACCGCGGACCCTAA
1301 GACACCTGCTGTACCCTCCACCCCCACCCCACCCACCTCCCCCCAACTCCCTAGATGTGTCGTGGGCGGCTGAACGTCGCCCGTTTAAGGGGCGGGCCCC
1401 GGCTCCACGTGCTTTCTGCTGAGTGACTGAACTACATAAACAGAGGCCGGGAACGGGGCGGGGAGGAGGGAGAGCACAGGCTTTGACCGATAGTAACCTC
1501 TGCGCTCGGTGCAGCCGAATCTATAAAAGGAACTAGTCCCGGCAAAAACCCCGTAATTGCGAGCGAGAGTGAGTGGGGCCGGGACCCGCAGAGCCGAGCC
1601 GACCCTTCTCTCCCGGGCTGCGGCAGGGCAGGGCGGGGAGCTC (SEQ ID NO. 3)
```

transcription start site

TATA box nuclear hormone receptor half site

LXR response element

SP1 site

FIG. 13

COMPOSITIONS AND METHODS FOR INCREASING CHOLESTEROL EFFLUX AND RAISING HDL USING ATP BINDING CASSETTE TRANSPORTER PROTEIN ABC1

This application is a divisional of U.S. patent application Ser. No. 09/596,141, filed Jun. 16, 2000, now U.S. Pat. No. 6,821,774, issued Nov. 23, 2004, which claims benefit of U.S. Provisional Application No. 60/140,264 filed Jun. 18, 1999, U.S. Provisional Application No. 60/153,872 filed Sep. 14, 1999 and U.S. Provisional Application No. 60/166,573 filed Nov. 19, 1999.

TECHNICAL FIELD OF INVENTION

The present invention relates to novel ABC1 polypeptides and nucleic acid molecules encoding the same. The invention also relates to recombinant vectors, host cells, and compositions comprising ABC1 polynucleotides, as well as to methods for producing ABC1 polypeptides. The invention also relates to antibodies that bind specifically to ABC1 polypeptides. In addition, the invention relates to methods for increasing cholesterol efflux as well as to methods for increasing ABC1 expression and activity. The present invention further relates to methods for identifying compounds that modulate the expression of ABC1 and methods for detecting the comparative level of ABC1 polypeptides and polynucleotides in a mammalian subject. The present invention also provides kits and compositions suitable for screening compounds to determine the ABC1 expression modulating activity of the compound, as well as kits and compositions suitable to determine whether a compound modulates ABC1-dependent cholesterol efflux.

BACKGROUND OF THE INVENTION

Circulating lipids in human plasma or lymphatic fluid consist of cholesterol, cholesteryl esters, triglycerides and phospholipids. These lipids are transported in large molecular complexes called lipoproteins, which consist of a core of cholesteryl esters and/or triglycerides, an envelope of phospholipids and free cholesterol, and apolipoproteins (Scriver et al., Eds., *The Metabolic and Molecular Basis of Inherited Disease,* 7$^{th}$ Ed., p. 1841-1851 (McGraw-Hill, New York 1995)). Apolipoproteins are involved in the assembly and secretion of the lipoprotein, as well as the activation of lipoprotein modifying enzymes, such as lecithin cholesterol acyl transferase (LCAT). In addition, apolipoproteins provide structural integrity and are ligands for a large spectrum of receptors and membrane docking proteins. The plasma lipoproteins are categorized into five types according to size: chylomicrons (largest in size and lowest in density), very low density lipoproteins (VLDL), intermediate density lipoproteins (IDL), low density lipoproteins (LDL) and high density lipoprotein (HDL).

Chylomicrons, VLDLs, IDLs, and LDLs transport exogenous and endogenous cholesterol and triacylglycerols to peripheral sites, where the lipids play a role in various metabolic pathways and serve as a major constituent of cell membranes. Chylomicrons are assembled in the intestinal mucosa as a means to transport dietary cholesterol and triacylglycerols to various tissues. VLDLs are formed in the liver to transport endogenous cholesterol and triacylglycerols synthesized by the liver to extra-hepatic tissues, such as muscle and adipose tissue. In fasting serum, VLDLs contain 10-15% of the total serum cholesterol and most of the triglyceride. In circulation, VLDLs are converted to LDLs through the action of lipoprotein lipase. LDLs are the primary plasma carriers of cholesterol for delivery to all tissues, typically containing 60-70% of the total fasting serum cholesterol.

In contrast, HDLs are involved in "reverse cholesterol transport", the pathway by which excess cholesterol is transported from peripheral sites back to the liver, where it is excreted in the form of bile salts (Glomset, J. A., *J. Lipid Res.,* 9, 155-167 (1968)). Nascent HDLs are synthesized de novo in the liver and small intestine, as protein-rich disc-shaped particles devoid of cholesterol and cholesterol esters. In fact, a major function of HDLs is to act as circulating stores of apolipoproteins, primarily apo C-I, apo C-II, and apoE. The nascent or protein-rich HDLs are converted into spherical lipoprotein particles through the accumulation of cholesteryl esters obtained from cellular sources. The HDL normally contain 20-30% of the total fasting serum cholesterol.

According to current theories, the reverse efflux of cellular cholesterol to HDL is mediated through two mechanisms: an aqueous diffusion pathway and an apolipoprotein-mediated pathway. The relative importance of these distinguishable mechanisms depends on the cell type and metabolic state (Oram et al., *J. Lipid Res.,* 37:2743-2491 (1996); Rothblat et al., *J. Lipid Res.,* 40:781-796 (1999); Stein et al., *Atherosclerosis,* 144:285-301 (1999)). For many cells, the aqueous diffusion pathway is the principle pathway through which cholesterol efflux occurs (Johnson et al., *Biochim. Biophys. Acta,* 1085:273-298 (1991)). This pathway involves the bidirectional exchange of cholesterol between cell membranes and a lipoprotein acceptor, such as HDL, in the extracellular space through a process of passive transport (Remaley et al., *Arterioscler. Thromb. Vasc. Biol.,* 17:1813-1821 (1997); Rothblat et al., *J. Lip. Res.,* 40:781-796 (1999)). The exchange may occur primarily at surface microdomains known as caveolae (Fielding et al., *Biochemistry,* 34:14288-14292 91995)). Net efflux can be driven by conversion of cholesterol in the exteracellular compartment to cholesteryl ester by the action of LCAT.

Alternatively, in macrophage and fibroblast cells, cholesterol and phospholipid efflux is primarily mediated through apolipoproteins, such as apo A-I, apo A-II, and Apo E (Remaley, supra (1997); Francis, et al., *J. Clin. Invest.,* 96:78-87 (1995); Vega et al., *J. Intern. Med.,* 226:5-15 (1989); Sakar et al., *Biochim. Biophys. Acta,* 1438: 85-98 (1999); Hara et al., *J. Biol. Chem.,* 266:3080-3086 (1991); Fielding et al., *J. Lipid Res.,* 38, 1503-1521 (1997); Oram et al., *J. Lipid Res.,* 37, 2743-2491 (1996)). The process of apolipoprotein-mediated lipid efflux particularly dominates in macrophages and other scavenger cells when they are cholesterol-loaded and/or growth-arrested. Apolipoprotein-mediated efflux is an active transport process that requires the direct interaction of the apolipoprotein with the cell surface, the lipidation of the apolipoprotein, and the subsequent dissociation of the lipid-apolipoprotein particle from the cell (Oram, supra (1996); Mendez, A. J., *J. Lipid Res.,* 38, 1807-1821 (1997); Remaley, supra (1997); Mendez, A. J., *J.Lipid Res.,* 37, 2510-2524 (1996)). Once removed from the cell, the cholesterol-rich HDL particles are transported to the liver and removed from the body as described.

Abnormal lipoprotein function and/or metabolism resulting from genetic defect or as a secondary effect of another disorder can have serious biological consequences. In addition to dietary influences, disorders such as diabetes, hypothyroidism, and liver disease can result in elevated plasma levels of LDL-cholesterol and triglycerides. Elevated levels of LDL-cholesterol and triglycerides have been identified as major risk factors associated with the incidence of coronary heart disease, which is the primary cause of death in the United States and other industrialized nations (Hokanson et al., *J. Cardiovasc. Risk.,* 3:213-219 (1996); The Expert Panel, *JAMA,* 269:3015-3023 (1993)). The accumulation of excess LDL-cholesterol on arterial walls can lead to the formation of atherosclerotic plaques, which play a major role in the development of heart disease. A plaque is believed to form when free radicals released from arterial walls oxidize LDL. According to theory, the oxidized form of LDL triggers an inflammatory response, attracting circulating cells to the site which contribute to the formation of a lipid plaque. Among these are macrophages and other cells that contain scavenger receptors that accumulate cholesterol in an unregulated manner (Brown et al., *Ann. Rev. Biochem.,* 52:223-261 (1986)). Vast stores of internal cholesterol result in conversion to a foam cell phenotype, which is believed to be a major contributor to the development of vascular lesions. As the plaque builds up, the arterial walls constrict, reducing blood flow to the heart.

Interestingly, however, an estimated 60% of heart attacks occur in persons who do not have elevated blood levels of LDL-cholesterol. Of these, an estimated 45% are associated with below average blood levels of HDL-cholesterol, indicating that low HDL-cholesterol level is a significant risk factor for coronary heart disease. In fact, recent studies have indicated that a decreased HDL-cholesterol level is the most common lipoprotein abnormality seen in patients with premature coronary artery disease (Genest J., *Circulation,* 85:2025-2033 (1992); Genest et al., *Arterioscler. Thromb.,* 13:1728-1737 (1993)). Although the basis for the inverse association between HDL-cholesterol and coronary heart disease is not well understood, it has been suggested that the cardioprotective role of HDL may stem from its activity relating to the promotion of cholesterol efflux from macrophage foam cells in atherosclerotic lesions.

One example of cardiovascular disease associated with low HDL is Tangier disease (TD), a rare genetic disorder characterized by a near or complete absence of circulating HDL. In addition to near zero plasma levels of HDL, patients with TD have a massive deposition and accumulation of cholesteryl esters in several tissues, including tonsils, lymph nodes, liver, spleen, thymus, intestine, and Schwann cells (Fredrickson, D. S., *J. Clin. Invest.,* 43, 228-236 (1964); Assmann et al., *The Metabolic Basis of Inherited Disease*, (McGraw-Hill, New York, 1995)). Although the cellular mechanisms have not been previously identified, recent studies have shown that cells from subjects with TD are defective in the process of apolipoprotein-mediated removal of cholesterol and phospholipids (Remaley et al., *Arterioscler. Thromb. Vasc. Biol.,* 17, 1813-1821 (1997); Francis et al., *J. Clin. Invest.,* 96, 78-87 (1995); Rogler et al., *Arterioscler. Thromb. Vasc. Biol.,* 15, 683-690 (1995)). These results have led to the proposal that the severe HDL deficiency in TD patients stems from the inability of nascent apo A-I to acquire lipids. Because they do not mature into lipid-rich particles, the nascent HDL in TD patients is rapidly catabolized and removed from the plasma, resulting in the near zero levels of circulating HDL (Remaley, supra (1997); Francis, supra (1995); Horowitz et al., *J. Clin. Invest.,* 91, 1743-1752 (1993); Schaefer et al., *J. Lip. Res.,* 22:217-228 (1981)).

Other disorders associated with severe premature atherosclerosis and high risk for coronary heart disease resulting from diminished HDL-cholesterol levels are hypoalphalipoproteinemia and familial HDL deficiency syndrome (FHA). Persons with these disorders often have normal LDL-cholesterol and triglyceride levels. In addition, disorders such as diabetes, alcoholism, hypothyroidism, liver disease, and elevated blood pressure can result in diminished plasma levels of HDL-cholesterol, although many of these disorders are also accompanied by elevated LDL-cholesterol and triglceride levels.

Current treatments for coronary heart disease have focused primarily on diet manipulations and/or drug therapies aimed at lowering the plasma level of LDL-cholesterol by inhibiting LDL secretion or promoting LDL turnover. Derivatives of fibric acid, such as clofibrate, gemfibrozil, and fenofibrate, promote rapid VLDL turnover by activating lipoprotein lipase. Nicotinic acid reduces plasma levels of VLDL and LDL by inhibiting hepatic VLDL secretion. In addition, HMG-CoaA reductase inhibitors, such as mevinolin, mevastatin, pravastatin, simvastatin, fluvastatin, and lovastatin reduce plasma LDL levels by inhibiting the intracellular synthesis of cholesterol, which causes an increase in the cellular uptake of LDL. In addition, bile acid-binding resins, such as cholestyrine, colestipol and probucol decrease the level of LDL-cholesterol by increasing the catabolism of LDL-cholesterol in the liver.

However, many of these therapies are associated with low efficacy and/or side effects that may prevent long-term use. For example, use of HMG-CoaA reductase inhibitors carry a significant risk of toxicity because they inhibit the synthesis of mevalonate, which is required for the synthesis of other important isoprenoid compounds in addition to cholesterol. Also, gemfibrozil and nicotinic acid are associated with serious adverse effects, including renal injury, myopathy, myoglobinuria and intolerable skin flushing and itching. In addition, the role of probucol in treating patients with coronary heart disease is uncertain because its administration results in lower HDL-cholesterol levels as a side effect of reducing LDL-cholesterol.

Furthermore, treating patients who have isolated low HDL-cholesterol levels provides a particularly difficult therapeutic challenge. For instance, patients with Tangier disease exhibit a 4- to 6-fold increase in cardiovascular disease even though their LDL levels are already reduced by about 50%. While there is some evidence that gemfibrozil and nicotinic acid may simultaneously elevate HDL levels, in general, therapies aimed at lowering plasma LDL-cholesterol levels are not effective for Tangier patients who suffer from coronary heart disease as a result of diminished HDL levels. Likewise, patients with hypoalphalipoproteinemia, familial HDL deficiency syndrome, or other cardiovascular disease resulting from low levels of HDL will not benefit from therapies aimed at lowering the level of plasma LDL.

The problems associated with current therapies for cardiovascular disease stem partially from the fact that the biology involved in the movement of cholesterol in and out of cells is not fully understood. Furthermore, the proteins that play a role in cholesterol movement are not fully known. Therefore, there remains a need for a better understanding of cholesterol cell biology, as well as new methods for treating humans suffering from cardiovascular disease and other disorders associated with hypercholesterolemia. Additionally, there remains a need for new methods of diagnosing cardiovascular disease and new methods of screening patients to identify those at high risk for developing cardiovascular disease.

The identification of genes and proteins involved in cholesterol transport would be useful in the development of pharmaceutical agents for the treatment of heart disease and other disorders associated with hypercholesterolemia and atherosclerosis. In addition, the identification of such genes would be useful in the development of screening assays to screen for compounds that regulate the expression of genes associated with cholesterol transport. The identification of such regulatory compounds would be useful in the development of further therapeutic agents. Furthermore, the identification of genes and proteins involved in cholesterol transport would be useful as diagnostic indicators of cardiovascular disease and other disorders associated with hypercholesterolemia.

SUMMARY OF THE INVENTION

The present invention provides novel polypeptides and polynucleotides involved in cholesterol efflux. Specifically, the present invention provides novel ATP-Binding Cassette (ABC1) polypeptides and novel polynucleotides that encode ABC1 polypeptides. The terms "ABC1" and "ABCA1" are alternative names for the same ATP-Binding Cassette protein and gene. The invention provides ABC1 polypeptides, polypeptide fragments, and polypeptide variants. In one preferred embodiment, the present invention provides an isolated polypeptide comprising SEQ ID NO: 2. In another preferred embodiment, the present invention provides an isolated polypeptide comprising an amino acid sequence that has at least 98% identity to SEQ ID NO: 2. The present invention also provides ABC1 polypeptides from Tangier disease patients. In one preferred embodiment, the present invention provides an isolated polypeptide comprising SEQ ID NO: 8. In another preferred embodiment, the present invention provides an isolated polypeptide comprising SEQ ID NO: 10.

In addition, the present invention provides ABC1 polynucleotides, polynucleotide fragments, and polynucleotide variants. In one preferred embodiment, the present invention provides an isolated polynucleotide that encodes the polypeptide comprising SEQ ID NO: 2. In another preferred embodiment, the invention provides an isolated polynucleotide that encodes a polypeptide comprising an amino acid sequence that has at least 98% identity to SEQ ID NO: 2. Also, in other preferred embodiments, the invention provides an isolated polynucleotide comprising a nucleotide sequence that is complementary to a polynucleotide encoding the polypeptide comprising SEQ ID NO: 2 or an isolated polynucleotide comprising a nucleotide sequence that is complementary to a polynucleotide encoding the polypeptide comprising an amino acid sequence that has at least 98% identity to SEQ ID NO: 2.

In another preferred embodiment, the present invention provides an isolated ABC1 polynucleotide comprising SEQ ID NO: 1. In a further preferred embodiment, the present invention provides an isolated polynucleotide comprising nucleotides 291-7074 of SEQ ID NO: 1. In yet another preferred embodiment, the invention provides a polynucleotide comprising a nucleotide sequence that has at least 90% identity with SEQ ID NO: 1. More preferably, the polynucleotide comprises a nucleotide sequence that has at least 95% identity with SEQ ID NO: 1. In other more preferred embodiments, the polynucleotide comprises a nucleotide sequence that has at least 96%, 97%, 98%, or 99% identity to SEQ ID NO: 1. Also, in other preferred embodiments, the present invention provides an isolated polynucleotide comprising a nucleotide sequence that is complementary to the polynucleotide comprising SEQ ID NO: 1, an isolated polynucleotide comprising a nucleotide sequence that is complementary to a polynucleotide comprising nucleotides 291-7074 of SEQ ID NO: 1, and an isolated polynucleotide that is complementary to a polynucleotide comprising a nucleotide sequence that has at least 90% identity with SEQ ID NO: 1.

The present invention also provides ABC1 polynucleotides corresponding to the 5' flanking region of the ABC1 gene. In one preferred embodiment, the invention provides an isolated polynucleotide comprising SEQ ID NO: 3. In other preferred embodiments, the invention provides an isolated polynucleotide comprising nucleotides 1-1532, 1080-1643, 1181-1643, 1292-1643, or 1394-1532 of SEQ ID NO: 3. Preferably, the isolated polynucleotide comprises nucleotides 1394-1532 of SEQ ID NO: 3. In another preferred embodiment, the invention provides an isolated polynucleotide that hybridizes under stringent conditions to a polynucleotide comprising SEQ ID NO: 3. Also, in other preferred embodiments, the present invention provides an isolated polynucleotide that hybridizes under stringent conditions to a polynucleotide comprising nucleotides 1-1532, 1080-1643, 1181-1643, 1292-1643, or 1394-1532 of SEQ ID NO: 3. In yet another preferred embodiment of the present invention, an isolated polynucleotide that has at least 80% identity to a polynucleotide comprising SEQ ID NO: 3 is provided. More preferably, the polynucleotide has at least 90% identity to a polynucleotide comprising SEQ ID NO: 3. Even more preferably, the polynucleotide has at least 95% identity to a polynucleotide comprising SEQ ID NO: 3. Also provided in preferred embodiments is an isolated polynucleotide that has at least 80% identity to a polynucleotide comprising nucleotides 1-1532, 1080-1643, 1181-1643, 1292-1643, or 1394-1532 of SEQ ID NO: 3. More preferably, the polynucleotide has at least 90% identity, and even more preferably at least 95% identity, to a polynucleotide comprising nucleotides 1-1532, 1080-1643, 1181-1643, 1292-1643, or 1394-1532 of SEQ ID NO: 3. In addition, the present invention provides an isolated polynucleotide comprising a nucleotide sequence that is complementary to the above described 5' flanking ABC1 polynucleotides. In one preferred embodiment, the invention provides an isolated polynucleotide comprising a nucleotide sequence that is complementary to a polynucleotide comprising SEQ ID NO: 3. In another preferred embodiment, the present invention provides an isolated polynucleotide comprising a nucleotide sequence that is complementary to a polynucleotide comprising nucleotides 1-1532, 1080-1643, 1181-1643, 1292-1643, or 1394-1532 of SEQ ID NO: 3.

The present invention also provides ABC1 polynucleotides corresponding to the 3' flanking region of the ABC1 gene. In preferred embodiments, the invention provides an isolated polynucleotide comprising SEQ ID NO: 4, SEQ ID NO: 5, or SEQ ID NO: 6, and the complementary sequences thereof. In other preferred embodiments, the invention provides an isolated polynucleotide that hybridizes under stringent conditions to a polynucleotide comprising SEQ ID NO: 4, SEQ ID NO: 5, or SEQ ID NO: 6, and the complementary sequences thereof. In still other preferred embodiments, the invention provides an isolated polynucleotide that has at least 80% identity to a polynucleotide comprising SEQ ID NO: 4, SEQ ID NO: 5, or SEQ ID NO: 6, and the complementary sequence thereof. More preferably, the polynucleotide has at least 90% identity to a polynucleotide comprising SEQ ID NO: 4, SEQ ID NO: 5, or SEQ ID NO: 6. Even more preferably, the polynucleotide has at least 95% identity to a polynucleotide comprising SEQ ID NO: 4, SEQ ID NO: 5, or SEQ ID NO: 6.

In addition, the present invention also provides ABC1 polynucleotides from Tangier disease patients. In one preferred embodiment, the present invention provides an isolated polynucleotide encoding the polypeptide comprising SEQ ID NO: 8. In another preferred embodiment, the present invention provides an isolated polynucleotide comprising SEQ ID NO: 7. In yet another embodiment, the present invention provides an isolated polynucleotide encoding the polypeptide comprising SEQ ID NO: 10. In still another preferred embodiment, the present invention provides an isolated polynucleotide comprising SEQ ID NO: 9. The present invention further provides an isolated polynucleotide comprising a nucleotide sequence that is complementary to the described polynucleotides.

In another aspect, the present invention provides a composition comprising any of the above described polynucleotides and a suitable carrier. In one preferred embodiment, the present invention provides a composition comprising an isolated polynucleotide encoding a polypeptide comprising SEQ ID NO: 2, a polynucleotide comprising SEQ ID NO: 1, a polynucleotide comprising nucleotides 291-7074 of SEQ ID NO: 1, or a polynucleotide encoding a polypeptide comprising an amino acid sequence that has at least 98% identity to SEQ ID NO: 2, and a suitable carrier. In another preferred embodiment, the composition comprises an isolated polynucleotide comprising a nucleotide sequence that has at least 90% identity with a polynucleotide comprising SEQ ID NO: 1 and a suitable carrier. In other preferred embodiments, the composition comprises an isolated polynucleotide comprising SEQ ID NO: 3 or an isolated polynucleotide comprising nucleotides 1-1532, 1080-1643, 1181-1643, 1292-1643, or 1394-1532 of SEQ ID NO: 3 and a suitable carrier. In still other preferred embodiments, the invention provides a composition comprising a polynucleotide that hybridizes under stringent conditions to a polynucleotide comprising SEQ ID NO: 3, or a polynucleotide comprising nucleotides 1-1532, 1080-1643, 1181-1643, 1292-1643, or 1394-1532 of SEQ ID NO: 3, as well as a composition comprising a polynucleotide that has at least 80% identity to a polynucleotide comprising SEQ ID NO: 3, or a polynucleotide comprising nucleotides 1-1532, 1080-1643, 1181-1643, 1292-1643, or 1394-1532 of SEQ ID NO: 3 and a suitable carrier. Also provided by the present invention is a composition comprising an isolated polynucleotide comprising a nucleotide sequence that is complementary to any of the described polynucleotides and a suitable carrier.

In addition, the present invention provides recombinant vectors and host cells comprising any of the described ABC1 polynucleotide sequences. In one preferred embodiment, the present invention provides a recombinant vector comprising an isolated polynucleotide encoding a polypeptide comprising SEQ ID NO: 2, an isolated polynucleotide comprising SEQ ID NO: 1, an isolated polynucleotide comprising nucleotides 291-7074 of SEQ ID NO: 1, or an isolated polynucleotide encoding the polypeptide comprising an amino acid sequence that has at least 98% identity to SEQ ID NO: 2. In another preferred embodiment, the recombinant vector comprises an isolated polynucleotide comprising a nucleotide sequence that has at least 90% identity, and more preferably at least 95% identity, with a polynucleotide comprising SEQ ID NO: 1. In still another preferred embodiment, the recombinant vector comprises an isolated polynucleotide comprising SEQ ID NO: 7 or SEQ ID NO: 9. The present invention further provides a recombinant vector comprising an isolated polynucleotide comprising a nucleotide sequence that is complementary to any of the described polynucleotides. In yet another preferred embodiment, the recombinant vector comprises any of the described polynucleotides and further comprises a heterologous promoter polynucleotide. One suitable heterologous promoter is a cytomegalovirus promoter. In a particularly preferred embodiment, the recombinant vector is pCEPhABC1.

The present invention also provides a recombinant vector comprising an isolated polynucleotide comprising an ABC1 5' flanking sequence. In one preferred embodiment, the invention provides a recombinant vector comprising an isolated polynucleotide comprising SEQ ID NO: 3 or an isolated polynucleotide comprising nucleotides 1-1532, 1080-1643, 1181-1643, 1292-1643, or 1394-1532 of SEQ ID NO: 3. In still other preferred embodiments, the invention provides a recombinant vector comprising a polynucleotide that hybridizes under stringent conditions to the polynucleotide of SEQ ID NO: 3, or a polynucleotide comprising nucleotides 1-1532, 1080-1643, 1181-1643, 1292-1643, or 1394-1532 of SEQ ID NO: 3, as well as a recombinant vector comprising a polynucleotide that has at least 80% identity to these polynucleotides. The present invention further provides a recombinant vector comprising an isolated polynucleotide comprising a nucleotide sequence that is complementary to any of the described polynucleotides. In yet another preferred embodiment, the recombinant vector comprises any of the described polynucleotides and further comprises at least one polynucleotide encoding a heterologous polypeptide. Suitable heterologous polypeptides include luciferase, β-galactosidase, chloramphenicol acetyl transferase transferase, and green fluorescent proteins. Preferably, the heterologous polypeptide is a luciferase protein. In a particularly preferred embodiment, the recombinant vector is pAPR1.

In addition, the present invention provides host cells comprising any of the described recombinant vectors. The present invention further provides compositions comprising any of the described recombinant vectors and a suitable carrier.

The present invention also provides methods for producing the ABC1 protein in a mammalian host cell as well as methods for expressing the ABC1 protein in a mammalian subject. The method for producing an ABC1 protein in a mammalian host cell comprises the steps of: (a) transfecting the mammalian host cell with a recombinant expression vector comprising a polynucleotide encoding ABC1 in an amount sufficient to produce a detectable level of ABC1 protein, and (b) purifying the produced ABC1 protein. The method for expressing ABC1 protein in a mammalian subject comprises the step of administering to a mammalian subject a recombinant expression vector comprising a polynucleotide encoding ABC1 in an amount sufficient to express ABC1 protein in the mammalian subject.

In addition, the present invention provides compositions and methods suitable for increasing cholesterol efflux from cells of a mammalian subject. In one preferred embodiment, the method comprises administering to the mammalian subject a recombinant expression vector comprising a polynucleotide encoding ABC1 in an amount sufficient to increase cholesterol efflux from the cells. Suitable recombinant expression vectors include vectors comprising an isolated polynucleotide encoding a polypeptide comprising SEQ ID NO: 2, an isolated polynucleotide comprising SEQ ID NO: 1, an isolated polynucleotide comprising nucleotides 291-7074 of SEQ ID NO: 1, and an isolated polynucleotide encoding the polypeptide comprising an amino acid sequence that has at least 98% identity to SEQ ID NO: 2. Preferred expression vectors include viral vectors, especially adenoviral vectors and lentiviral vectors. In other embodiments, the invention provides non-viral delivery systems, including DNA-ligand complexes, adenovirus-ligand-DNA complexes, direct injection of DNA, $CaPO_4$ precipitation, gene gun techniques, electroporation, liposomes and lipofection.

In another preferred embodiment, the method for increasing cholesterol efflux from cells of a mammalian subject comprises administering to the mammalian subject a therapeutic amount of a compound that increases the expression of ABC1 in the cells. One suitable method comprises administering to the mammalian subject a cAMP analogue. Suitable cAMP analogues include 8-bromo cAMP, N6-benzoyl cAMP, and 8-thiomethyl cAMP. Another suitable method comprises administering to the mammalian subject a compound that increases the synthesis of cAMP, e.g. forskolin. Yet another suitable method comprises administering to the mammalian subject a compound that inhibits the degradation of cAMP, such as a phosphodiesterase inhibitor. Suitable phosphodiesterase inhibitors include rolipram, theophylline, 3-isobutyl-1-methylxanthine, R020-1724, vinpocetine, zaprinast, dipyridamole, milrinone, amrinone, pimobendan, cilostamide, enoximone, peroximone, and vesnarinone.

In addition, another suitable method for increasing cholesterol efflux from cells of a mammalian subject comprises administering to the mammalian subject a least one ligand for a nuclear receptor in an amount sufficient to increase cholesterol efflux. Suitable ligands include LXR, RXR, FXR, SXR and PPAR ligands. In one preferred embodiment, the method comprises administering to a mammalian subject a ligand for an LXR nuclear receptor. Suitable LXR ligands include 20(S) hydroxycholesterol, 22(R) hydroxycholesterol, 24(S) hydroxycholesterol, 25-hydroxycholesterol, and 24(S), 25 epoxycholesterol. Preferably, the LXR ligand is 20(S) hydroxycholesterol. In another preferred embodiment, the method comprises administering to a mammalian subject a ligand for an RXR nuclear receptor. Suitable RXR ligands include 9-cis retinoic acid, retinol, retinal, all-trans retinoic acid, 13-cis retinoic acid, acitretin, fenretinide, etretinate, CD 495, CD564, TTNN, TTNNPB, TTAB, and LGD 1069. Preferably, the RXR ligand is 9-cis retinoic acid. In another preferred embodiment, the method comprises administering to a mammalian subject a ligand for a PPAR nuclear receptor. One suitable ligand is a ligand selected from the class of thiazolidinediones. In yet another preferred embodiment, the method comprises administering at least two ligands for a nuclear receptor. In a particularly preferred embodiment, the ligands are 20(S) hydroxycholesterol and 9-cis retinoic acid.

In addition, another suitable method for increasing cholesterol efflux from cells of a mammalian subject comprises administering to the mammalian subject an eicosanoid in an amount sufficient to increase cholesterol efflux. Suitable eicosanoids include prostaglandin E2, prostaglandin J2, and prostacyclin (prostaglandin 12).

In another embodiment, the present invention provides a method for increasing cholesterol efflux from cells of a mammalian subject comprising administering to the mammalian subject a compound that increases ABC1 activity in an amount sufficient to increase cholesterol efflux from the cells.

The present invention also provides methods suitable for increasing the gene expression of ABC1 in a mammalian subject. In one preferred embodiment, the method comprises administering to the mammalian subject at least one ligand for a nuclear receptor in an amount sufficient to increase the gene expression of ABC1. Suitable ligands include ligands for LXR, RXR, FXR, SXR, and PPAR nuclear receptors. In another preferred embodiment, the method comprises administering to the mammalian subject a cAMP analogue in an amount sufficient to increase the gene expression of ABC1. In yet another preferred embodiment, the method comprises administering to the mammalian subject a compound that increases the synthesis of cAMP in an amount sufficient to increase the gene expression of ABC1.

In addition, the present invention provides a method for screening a test compound for ABC1 expression modulating activity comprising the steps of: (a) operatively linking a reporter cDNA with an expression modulating portion of the mammalian ABC1 gene to produce a recombinant reporter construct; (b) transfecting the recombinant reporter construct into a population of host cells; (c) assaying the level of reporter gene expression in a sample of the host cells; (d) contacting the host cells with the test compound being screened; (e) assaying the level of reporter gene expression in a sample of the host cells after contact with the test compound; and (f) comparing the relative change in the level of reporter gene expression caused by exposure to the test compound, thereby determining the ABC1 expression modulating activity. The recombinant reporter construct comprises a reporter gene operatively linked to an expression modulating portion of the mammalian ABC1 gene, such as any of the ABC1 5' flanking region sequences provided by the present invention. In one preferred embodiment, the expression modulating portion of the ABC1 gene comprises SEQ ID NO: 3. In another preferred embodiment, the expression modulating portion of the ABC1 gene comprises nucleotides 1-1532, 1080-1643, 1181-1643, 1292-1643, 1394-1643, or 1394-1532 of SEQ ID NO: 3. Suitable reporter cDNAs include luciferase, β-galactosidase, chloramphenicol acetyl transferase, and green fluorescent protein cDNA. Preferably, the host cell is a mammalian cell. In a particularly preferred embodiment of the method, the recombinant reporter construct is pAPR1.

Also provided by the present invention is a method for screening a test compound to determine whether the test compound promotes ABC1-mediated cholesterol efflux from cells in culture comprising the steps of: (a) assaying the level of cholesterol efflux in a sample of mammalian cells maintained in culture to determine a control level of cholesterol efflux; (b) contacting the cells with the test compound being screened; (c) assaying the level of cholesterol efflux in a sample of cells after contact with the test compound; (d) assaying the level of ABC1-mediated cholesterol efflux in a sample of cells after contact with the test compound, thereby determining whether the test compound promotes ABC1-mediated cholesterol efflux from cells in culture. The cells can be derived from primary cultures or a cell line. Suitable cells for screening the test compound include fibroblast, macrophage, hepatic, and intestinal cell lines. Preferably, the cell line is RAW 264.7. In one preferred embodiment, the ABC1-mediated cholesterol efflux is measured using an anti-ABC1 antibody that inhibits the activity of ABC1 upon binding. In another preferred embodiment, the ABC1-mediated cholesterol efflux is measured using an antisense ABC1 polynucleotide. In a particularly preferred embodiment, the antisense polynucleotide comprises SEQ ID NO: 57.

In addition, the present invention provides methods for detecting the comparative level of ABC1 expression in cells of a mammalian subject. Such methods can be used to determine the susceptibility of a subject to coronary heart disease. A method for detecting the comparative level of ABC1 expression in cells of a mammalian subject is provided which comprises (a) obtaining a cell sample from the mammalian subject, (b) assaying the level of ABC1 mRNA expression in the cell sample; and (c) comparing the level of ABC1 mRNA expression in the cell sample with a pre-determined standard level of ABC1 mRNA expression, thereby detecting the comparative level of ABC1 gene expression in the cells of a mammalian subject. Suitable methods for measuring the level of ABC1 mRNA expression include, for example, RT-PCR, northern blot, and RNAse protection assay.

The present invention also provides methods for detecting the comparative level of ABC1 protein in cells of a mammalian subject. Such methods can be used to determine the susceptibility of a subject to coronary heart disease. A method for detecting the comparative amount of ABC1 protein in the cells of a mammalian subject is provided which comprises (a) obtaining a cell sample from the mammalian subject, (b) assaying the amount of ABC1 protein in the cell sample, and (c) comparing the amount of ABC1 protein in the cell sample with a pre-determined standard amount of ABC1 protein, thereby detecting the comparative level of ABC1 protein in the cells of the mammalian subject. The amount of ABC1 protein can be determined using various immunoassays available in the art. For example, the amount of ABC1 protein can be determined by (a) contacting the cell sample with a population of anti-ABC1 antibodies and (b) detecting the specific-binding ABC1 antibodies associated with the sample. Suitable methods for detecting ABC1 antibodies include western blotting, immunoprecipitation, and FACS.

In another aspect, the present invention provides antibodies that bind specifically to the described ABC1 polypeptides. In one preferred embodiment, the present invention provides an isolated antibody that binds specifically to an isolated polypeptide comprising SEQ ID NO: 2. In another preferred embodiment, the invention provides an isolated antibody that bind specifically to an isolated polypeptide comprising an amino acid sequence that has at least 98% identity with SEQ ID NO: 2. The antibody can be a monoclonal antibody or the antibody can be a polyclonal antibody. In yet another embodiment, the antibody, upon binding to an ABC1 polypeptide, inhibits the cholesterol transport activity of the ABC1 polypeptide.

In addition, the present invention provides kits suitable for screening a compound to determine the ABC1 expression modulating activity of the compound comprising a reporter cDNA operatively linked to an expression modulating portion of the mammalian ABC1 gene in an amount sufficient for at least one assay and instructions for use. In one preferred embodiment, the kit further comprises means for detecting the reporter gene. In another preferred embodiment, the expression modulating portion of the mammalian ABC1 gene comprises SEQ ID NO: 3. In yet another preferred embodiment, the expression modulating portion of the mammalian ABC1 gene comprises nucleotides 1-1532, 1080-1643, 1181-1643, 1292-1643, 1394-1643, or 1394-1532 of SEQ ID NO: 3. Suitable reporter cDNAs include luciferase, β-galactosidase, chloramphenicol acetyl transferase, and green fluorescent protein cDNA. Preferably, the reporter cDNA is luciferase. In a particularly preferred embodiment of the method, the recombinant reporter construct is pAPR1.

The present invention also provides kits suitable for screening a compound to determine whether the compound modulates ABC1-dependent cholesterol efflux. In one preferred embodiment, the kit comprises an inactivating anti-ABC1 antibody in an amount sufficient for at least one assay and instructions for use. In another preferred embodiment, the kit comprises an antisense ABC1 oligonucleotide in an amount sufficient for at least one assay and instructions for use. In a particularly preferred embodiment, the antisense ABC1 oligonucleotide comprises SEQ ID NO: 53.

Figure 10:
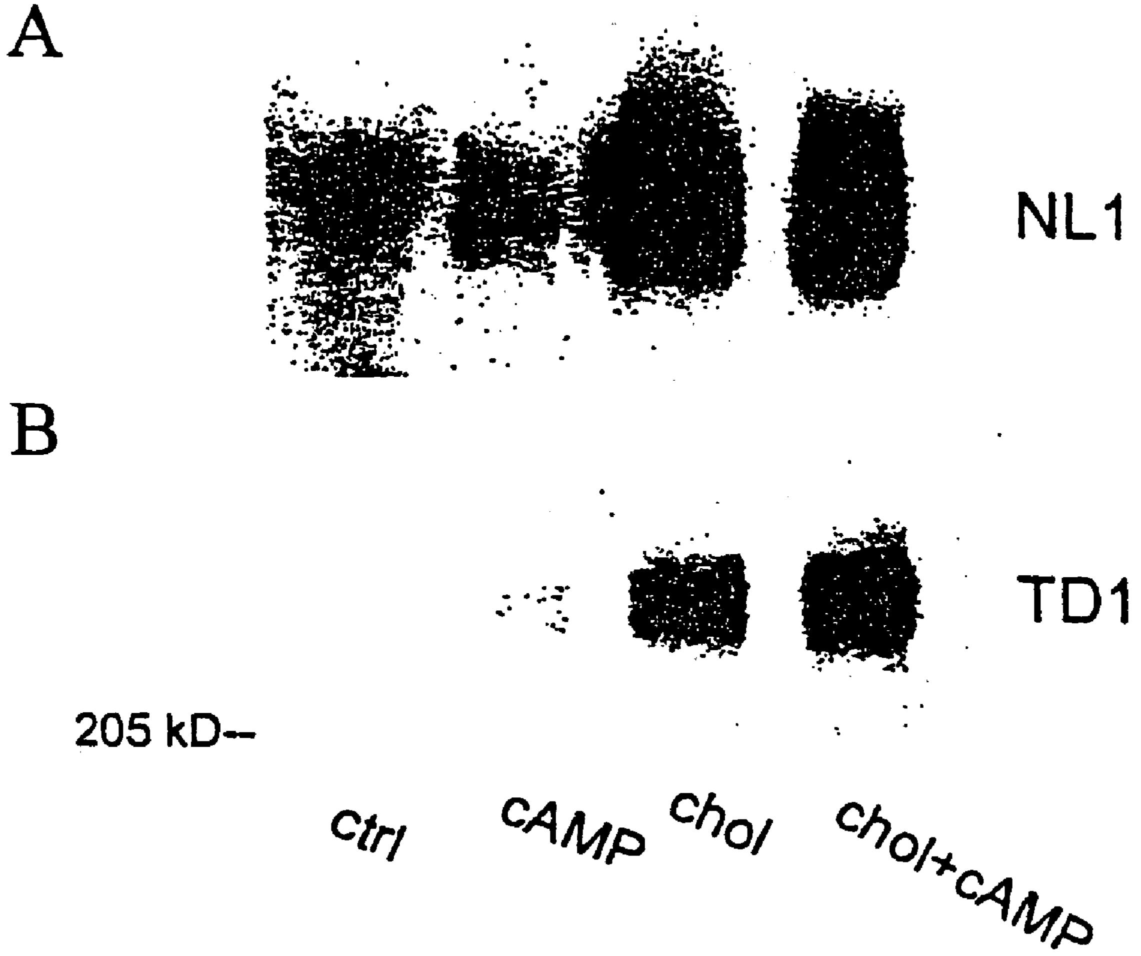
Figure 11:
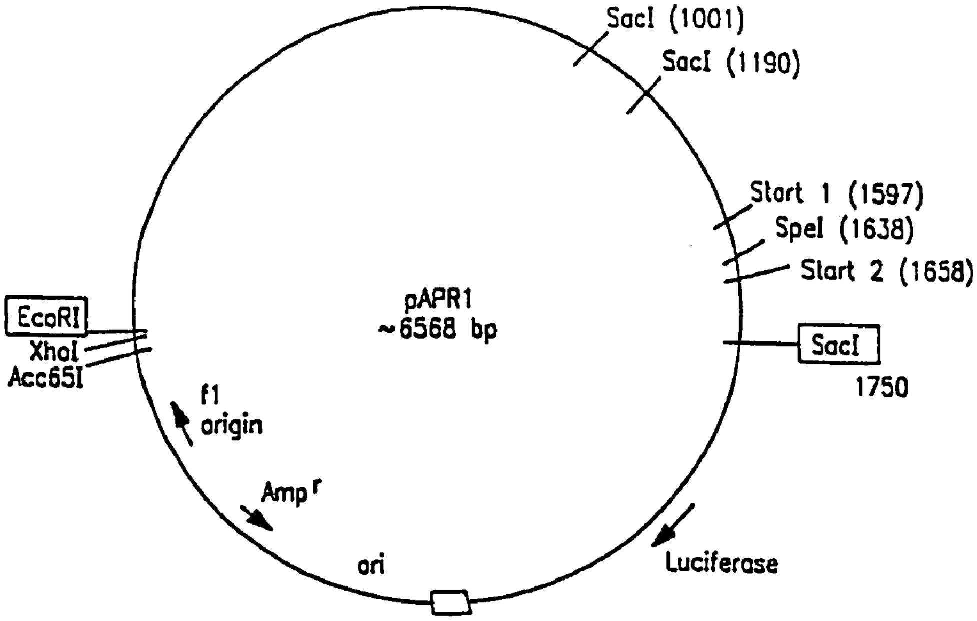
Figure 12:
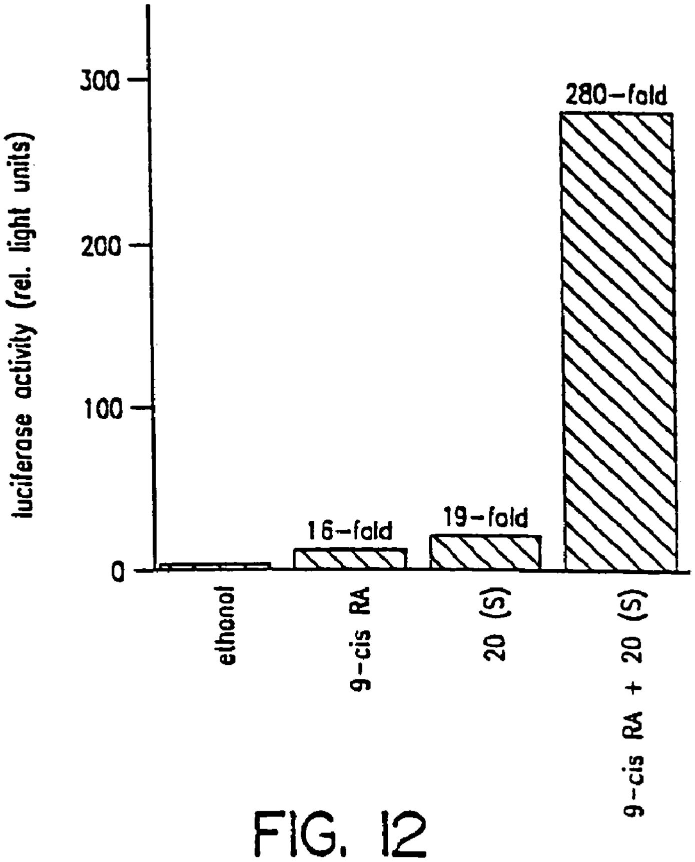

FIG. 10 shows the results of immunoprecipitation analyses indicating the level of cell-surface ABC1 protein found in normal fibroblasts (NL1, 10A) and fibroblasts from a Tangier's disease patient (TD1, 10B) in the presence of either no additives (control), 8-Br-cAMP (1 mM), cholesterol (30 μg/ml), or cholesterol and 8-Br-cAMP (30 μg/ml and 1 mM, respectively);

FIG. 11 is a schematic diagram showing a restriction map of the recombinant expression vector pAPR1, which contains the 5' flanking region of the ABC1 gene positioned upstream of the open reading frame of the luciferase reporter gene;

FIG. 12 is a graphical representation showing the level of luciferase reporter gene expression induced in RAW 264.7 cells transfected with pAPR1 in the presence of either EtOH (control), 20(S)—OH (10 μM), 9-cis RA (10 μM), or both 20(S)—OH and 9-cis RA (10 μM each);

FIG. 13 is a schematic diagram of the 5' flanking region of the ABC1 gene.

DETAILED DESCRIPTION OF THE PREFERRED EMBODIMENTS

In accordance with the present invention, novel polypeptides that increase the cholesterol efflux from cells are provided. In particular, the present invention provides novel ATP-Binding Cassette 1 (ABC1) polypeptides that have been shown to increase cholesterol efflux.

ABC1 is a member of the family of ATP-binding cassette proteins that reside in cell membranes and utilize ATP hydrolysis to transport a wide variety of substrates across the plasma membrane. It should be noted that the terms "ABC1" and "ABCA1" both refer to the same ATP-binding cassette protein. The term "ABCA1" was introduced in 1999 by a nomenclature committee and has received limited acceptance in the field. To date, more than 30 members of this family have been identified in the human genome. These homologous proteins contain channel-like structures through which molecules are transported through the cell membrane and one or two domains which bind to ATP to couple energy generating ATP-hydrolysis to transport. Family members include the multidrug resistance factors (MDR/P-glycoproteins; Chen et al., *Cell,* 47: 381-389 (1986); Stride et al., *Mol. Pharmacol.,* 49:962-971 (1996)), transporters associated with antigen presentation (Neefjes et al., *Science,* 261:769-771 (1993); Shepherd et al., *Cell,* 74:577-584 (1993)), and the cystic fibrosis transmembrane conductance regulator (Chang et al., *J. Biol. Chem.,* 269:18572-18575 (1994); Rommens et al., *Science,* 245: 1059-1065 (1989)). Members of the ABC transporter family are generally composed of 4 domains found within two symmetric halves that are linked by a long charged region and a highly hydrophobic segment. Each half contains a hydrophobic domain, containing 6 transmembrane segments and a hydrophilic nucleotide binding domain containing highly conserved Walker A and B sequence motifs typical of many ATPases (Hyde et al., *Nature,* 346:362-365 (1990); Luciani et al., *Genomics,* 21: 150-159 (1994)). The transporter activity is dependent on the interaction with ATP at the nucleotide binding domains and by regulation via phosphorylation of residues in the region linking the two symmetric halves (Becq et al., *J. Biol. Chem.,* 272: 2695-2699 (1997)).

Several lines of evidence described herein identified ABC1 as a pivotal protein in the apolipoprotein-mediated mobilization of intracellular cholesterol stores. First, the studies presented herein showed that ABC1 is defective in Tangier disease, a genetic disorder characterized by abnormal HDL-cholesterol metabolism. As shown previously, and herein at Example 1, the genetic defect in Tangier disease causes a defect in the pathway of apolipoprotein mediated efflux of cholesterol from within cells, resulting in significantly decreased cholesterol efflux activity and low HDL-cholesterol levels (Oram et al., *J. Lipid Res.,* 37:2743-2491 (1996); Francis et al., *J. Clin. Invest.,* 96: 78-87 (1995)). Genetic linkage analysis of families with Tangier disease assigned the defective gene to an interval on chromosome 9q31 (Rust et al., *Nature Genetics,* 20: 96-98 (1998)). A search of public databases revealed that the ABC1 gene was localized to chromosome 9q22-9q31, which is broader than, but includes the interval revealed in Rust et al. (Luciani et al., supra (1994)). Based on that data, radiation hybrid mapping of the human ABC1 gene was performed, which placed the gene between two markers squarely within the 7-cM region of human chromosome 9q31 reported by Rust et al. In addition, as shown in Example 2, microarray analysis revealed that the ABC1 gene is 2.5-fold underexpressed in Tangier patient cells as compared with normal cells. These studies identified the defective gene in Tangier disease as ABC1. In addition, further studies presented herein linked ABC1 activity to cholesterol efflux activity. First, studies showed that inhibitors of ABC1 transport activity, such as 4,4-diisothiocyanostilbene-2,2'-disulfonic acid (DIDS) and sulphobromophtaleine (BSP), also inhibited apoAI-mediated cholesterol efflux from fibroblast cells (see Example 6). Also, inhibition of ABC1 gene expression, using an antisense ABC1 oligonucleotide, was shown to inhibit apoAI-mediated cholesterol efflux from fibroblast cells (Example 7). In contrast, transfection studies, in which the ABC1 gene was transfected into mouse monocyte cells, showed that overexpression of ABC1 results in an increase in apoAI-mediated efflux (Example 8). Finally, RT-PCR performed using wildtype and Tangier patient mRNA revealed that ABC1 mRNA expression is regulated by cellular conditions related to cholesterol efflux in normal skin fibroblast cells, but not in Tangier patient fibroblasts (Example 9). Based on these findings, it was determined that ABC1 plays a major role in cholesterol efflux.

It is postulated that ABC1 plays a role in the translocation of intracellular cholesterol to the outer leaflet of the plasma membrane. Deficient transport of intracellular cholesterol due to a lack of ABC1 or defective ABC1 results in a lack of cholesterol in specific membrane domains with which apoAI and other apolipoproteins specifically interact (Stangl et al., *J. Biol. Chem.,* 273: 31002-31008 (1998); Babitt et al., *J. Biol. Chem.,* 272: 13242-13249 (1997))). The failed delivery of cholesterol to apoAI leads to the formation of cholesterol-deficient HDL particles that are rapidly removed from the plasma. (Bojanovski et al., *J. Clin. Invest.,* 80: 1742-1747 (1987)).

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

As used herein, the term "polynucleotide(s)" is defined to encompass DNA and RNA of both synthetic and natural origin. The polynucleotide may exist as single- or double-stranded DNA or RNA, or an RNA/DNA heteroduplex. Thus, the polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, or single, double-, and triple-stranded regions, single- and double-stranded RNA, and RNA that is mixture of single- and double-stranded regions, hybrid molecules comprising DNA and RNA that may be single-stranded or, more typically, double-stranded or triple-stranded, or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms of polynucleotides. The term "polynucleotide(s)" also embraces short polynucleotides often referred to as oligonucleotide(s).

The term "polypeptide(s)" refers to any peptide or protein comprising two or more amino acids joined to each other by peptide bonds or modified peptide bonds. "Polypeptide" refers to both short amino acid sequences, commonly referred to as peptides, as well as longer amino acid sequences, generally referred to as proteins. The polypeptide may contain amino acids other than the 20 gene encoded amino acids. Moreover, the polypeptide may be modified either by natural processes, such as processing and other post-translational modifications, or by chemical modification techniques, which are well-known in the art. A given polypeptide may contain many types of modifications. Also, the same type of modification may be present in the same or varying degree at one or more sites in the polypeptide. Modifications may occur anywhere in the polypeptide, including the peptide backbone, the amino acid side-chains, and the amino or carboxyl termini. Modifications include, but are not limited to, acetylation, acylation, ADP-ribosylation, amidation, formylation, gamma-carboxylation, glycosylation, hydroxylation, iodination, methylation, myristoylation, oxidation, phosphorylation, prenylation, sulfation, and selenoylation, as well as the covalent attachment of a nucleotide or nucleotide derivative, a lipid or lipid derivative, or a phosphotidylinositol. Other modifications include cross-linking, cyclization, formation of pyroglutamate, GPI anchor formation, proteolytic processing, racemization, and t-RNA-mediated addition of amino acids, such as arginylation and ubiquitination. See, for example, Proteins—Structure and Molecular Properties, $2^{nd}$ Ed., T. E. Creighton, W. H. Freedman and Co., New York (1993); Wold, F., Post-translational Protein Modification: Perspectives and Prospects, in Posttranslational Covalent Modification of Proteins, B. C. Johnson, Ed., Academic Press, New York (1983); Seifter et al., Meth. Enzymol., 182: 626-646 (1990); and Rattan et al., Protein Synthesis: Posttranslational Modifications and Aging, Ann. N.Y. Acad. Sci., 663: 48-62 (1992)). The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

A "polynucleotide" of the present invention also includes those polynucleotides capable of hybridizing, under stringent hybridization conditions, to SEQ ID NO:3 or nucleotides 1-1532, 1080-1643, 1181-1643, 1292-1643, 1394-1643, or 1394-1532 of SEQ ID NO: 3, or the complements thereof. A polynucleotide of the present invention also includes those polynucleotides capable of hybridizing, under stringent hybridization conditions, to SEQ ID NO:4, SEQ ID NO: 5, or SEQ ID NO: 6 or the complements thereof.

"Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

As used herein, the term "complementary" refers to the hybridization or base pairing between nucleotides, such as, for example, between the two strands of a double-stranded polynucleotide or between an oligonucleotide primer and a primer binding site on a single-stranded polynucleotide to be amplified or sequenced. Two single-stranded nucleotide molecules are said to be complementary when the nucleotides of one strand, optimally aligned with appropriate nucleotide insertions, deletions or substitutions, pair with at least about 80% of the nucleotides of the other strand.

"Identity", as known in the art, is a relationship between two or more polypeptide sequences or two or more polynucleotide sequences, as determined by comparing the sequences. "Identity" or "similarity" also has an art-recognized meaning that refers to the degree of sequence relatedness between polypeptide or polynucleotide sequences, as determined by the match between strings of such sequences. "Identity" and "similarity" can be calculated using a number of well known methods, including those published in Computational Molecular Biology, Lesk, A. M., ed., Oxford University Press, New York, (1988); Biocomputing: Informatics and Genome Projects, Smith, D. W., ed., Academic Press, New York, (1993); Computer Analysis of Sequence Data, Part I, Griffin, A. M., and Griffin, H. G., eds., Humana Press, New Jersey, (1994); Sequence Analysis in Molecular Biology, von Heinje, G., Academic Press, (1987); and Sequence Analysis Primer, Gribskov, M. and Devereux, J., eds., M Stockton Press, New York, (1991); and Carillo, H., and Lipton, D., SIAM J Applied Math 48:1073 (1988)). Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., SIAM J Applied Math 48:1073 (1988). Preferred methods to determine identity are designed to give the largest match between the sequences tested. Methods for aligning polynucleotides or polypeptides are codified in computer programs, including the GCG program package (Devereux, J., et al., Nucleic Acids Research (1984) 12(1):387 (1984)), BLASTP, BLASTN, FASTA (Atschul, S. F. et al., J. Molec. Biol. 215:403 (1990), Bestfit program (Wisconsin Sequence Analysis Package, Version 8 for Unix, Genetics Computer Group, University Research Park, 575 Science Drive, Madison, Wisc. 53711

(using the local homology algorithm of Smith and Waterman, Advances in Applied Mathematics 2:482-489 (1981)).

When using any of the sequence alignment programs to determine whether a particular sequence is, for instance, 90% identical to a reference sequence, the parameters are set so that the percentage of identity is calculated over the full length of the reference polypeptide or polynucleotide and that gaps in identity of up to 10% of the total number of nucleotides in the reference polynucleotide are allowed.

A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). The term "sequence" includes nucleotide and amino acid sequences. In a sequence alignment the query and subject sequences are either both nucleotide sequences or both amino acid sequences. The result of said global sequence alignment is in percent identity. Preferred parameters used in a FASTDB search of a DNA sequence to calculate percent identity are: Matrix=Unitary, k-tuple=4, Mismatch Penalty=1, Joining Penalty=30, Randomization Group Length=0, and Cutoff Score=1, Gap Penalty=5, Gap Size Penalty 0.05, and Window Size=500 or query sequence length in nucleotide bases, whichever is shorter. Preferred parameters employed to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in amino acid residues, whichever is shorter.

As an illustration, a polynucleotide having a nucleotide sequence of at least 90% "identity" to a sequence contained in SEQ ID NO: 1 means that the nucleotide sequence of the polynucleotide is identical to a sequence contained in SEQ ID NO: 1 except that the polynucleotide sequence may include up to ten point mutations per each 100 nucleotides of the total length of SEQ ID NO: 1. In other words, to obtain a polynucleotide comprising a nucleotide sequence that has at least 90% identity to SEQ ID NO: 1, up to 10% of the nucleotides in the sequence contained in SEQ ID NO: 1 can be deleted, inserted, or substituted with other nucleotides. These changes may occur anywhere throughout the polynucleotide, and may be interspersed either individually among nucleotides or in one or more contiguous groups within SEQ ID NO: 1.

Similarly, a polypeptide having an amino acid sequence of at least 98% "identity" to a sequence contained in SEQ ID NO: 2 means that the amino acid sequence of the polypeptide is identical to a sequence contained in SEQ ID NO: 2 except that the polypeptide sequence may include up to 2 amino acid alterations per each 100 amino acids of the total length of SEQ ID NO: 2. In other words, to obtain a polypeptide having an amino acid sequence at least 98% identical to SEQ ID NO: 2, up to 2% of the amino acid residues in the sequence contained in SEQ ID NO: 2 can be deleted, inserted, or substituted with other amino acid residues. These changes may occur anywhere throughout the polypeptide, and may be interspersed either individually among residues or in one or more contiguous groups within SEQ ID NO: 2.

"A polypeptide having biological activity" refers to a polypeptide exhibiting activity similar, but not necessarily identical, to an activity of a polypeptide of the present invention (e.g. cholesterol transport activity), as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.).

"Polypeptide variant" refers to a polypeptide differing from the ABC1 polypeptide of the present invention, but retaining essential properties thereof. Generally, variants are overall closely similar, and, in many regions, identical to the polypeptide comprising SEQ ID NO: 2. Preferably, the polypeptide variant retains its biological activity, i.e., cholesterol transport activity. Variants include, but are not limited to, splice variants and allelic variants, as well as addition, deletion, and substitution variants.

Likewise, "polynucleotide variant" refers to a polynucleotide differing from the polynucleotide of the present invention, but retaining essential properties thereof. The variants may contain alterations in the coding regions, non-coding regions, or both. Thus, for example, an ABC1 polynucleotide variant has a nucleotide sequence that differs from that of SEQ ID NO: 1, but encodes a polypeptide that has cholesterol transport activity. Also, for example, a polynucleotide variant has a nucleotide sequence that differs from that of SEQ ID NO: 3, but retains promoter activity. Especially preferred are polynucleotide variants containing alterations that produce silent substitutions, additions, or deletions, but do not alter the properties or activities of the encoded polypeptide. Nucleotide variants produced by silent substitutions due to the degeneracy of the genetic code are preferred. Moreover, variants in which 10-20, 5-10, 1-5, or 1-2 amino acids are substituted, deleted, or added in any combination are also preferred. Polynucleotide variants can be produced for a variety of reasons, e.g., to optimize codon expression for a particular host (e.g. changing codons in the human mRNA to those preferred by a bacterial host such as *E. coli*).

"Allelic variants" are naturally-occurring variants that refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

The term "conservative amino acid substitution" refers to a substitution of a native amino acid residue with a nonnative residue such that there is little or no effect on the polarity or charge of the amino acid residue at that position. For example, a conservative substitution results from the replacement of a non-polar residue in a polypeptide with any other non-polar residue. Another example of a conservative substitution is the replacement of an acidic residue with another acidic residue. Conservative substitutions are expected to produce ABC1 polypeptides having functional and chemical characteristics similar to those of the naturally-occurring ABC1 polypeptide.

The term "ortholog" refers to a polypeptide that corresponds to a polypeptide identified from a different species. For example, mouse and human ABC1 polypeptides are considered orthologs.

The term "vector" is used to refer to any molecule (e.g. nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

As used herein, the term "transcriptional regulatory region" or "expression modulating portion" refers to any region of the gene, including, but not limited to, promoters, enhancers, and repressors.

As used herein, the term "promoter" refers to an untranscribed sequence located upstream (i.e., 5') to the start codon of a structural gene (generally within about 100 to 1000 bp) that controls the transcription of the structural gene.

As used herein the term "enhancers" refers to cis-acting elements of DNA, usually about 10-300 bp in length, that act on the promoter to increase transcription. Enhancers are relatively orientation and position independent. They have been found 5' and 3' to the transcription unit.

"Host cell" is a cell that has been transformed or transfected, or is capable of transformation or transfection by an exogenous polynucleotide sequence. The term includes the progeny of the parent cell, whether or not the progeny is identical in morphology or in genetic make-up to the original parent, so long as the selected gene is present.

The term "operatively linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

ABC1 Polypeptodes

The present invention relates to novel human ABC1 polypeptides. In one embodiment, the ABC1 polypeptide comprises the amino acid sequence shown in SEQ ID NO: 2. In contrast to the human ABC1 protein reported by others, the ABC1 polypeptide shown in SEQ ID NO: 2 has an additional 60 amino acids at the amino terminus, revealing an ABC1 protein of 2261 amino acids rather than 2201 amino acids (see Langmann et al. in *Biochem. Biophys. Res. Comm.*, 257, 29-33 (1999)). In addition, the ABC1 polypeptide shown in SEQ ID NO: 2 differs from other reported sequences at several amino acid residues. Specifically, the present ABC1 polypeptide shown in SEQ ID NO: 2 has a K for R at residue 159, I for V at 765, M for I at 823, I for T at 1495, L for P at 1588, K for R at 1914, and L for P at 2108. To remain consistent with published notation, the above amino acid numbers are those of Lawn et al., *J. Clin. Invest.*, 104: R25-31 (1999), rather than those of SEQ ID NO: 2. As discussed in further detail below, the sequence difference likely arises from the fact that the first ABC1 cDNA was cloned from mouse using a PCR-based strategy and the subsequently reported human ABC1 cDNA sequences were predicted from the sequence of the mouse protein. The ABC1 protein has an approximate molecular weight of 240 kD as determined by SDS-PAGE.

The present invention also relates to ABC1 polypeptides comprising amino acid sequences which preferably have at least 98% identity over their entire length to the amino acid sequence of SEQ ID NO: 2. More preferably, the polypeptide has at least 99% identity over its entire length to the amino acid sequence of SEQ ID NO: 2. Most preferably, the polypeptide has 100% identity over its entire length to the amino acid sequence of SEQ ID NO: 2. As defined previously, the term "identity" refers to the degree of sequence relatedness between polypeptide sequences, which is further defined below.

Such related ABC1 polypeptides include substitution, deletion, and insertion variants, as well as allelic variants, splice variants, fragments, derivatives, and orthologs. Preferred polypeptides and polypeptides fragments include those polypeptides and fragments that possess the biological activity of ABC1. In particular, those polypeptides and fragments that mediate reverse cholesterol transport are preferred. Also preferred are polypeptides and fragments that have improved reverse cholesterol transport activity.

Substitution, deletion, and insertion variants refer to ABC1 polypeptides comprising amino acid sequences that contain one or more amino acid sequence substitutions, deletions, and/or additions as compared to the ABC1 amino acid sequence set forth in SEQ ID NO: 2. In preferred embodiments, the variants have from about 1 to 5, or from about 1 to 10, or from about 1 to 20, or from about 1 to 40, or from about 1 to 65 amino acid substitutions, additions, and/or deletions. For example, the variants can have an addition of one or more amino acid residues anywhere in the polypeptide as well as at the carboxyl terminus and/or at the amino terminus, as long as the variant retains biological function. Also, for example, one or more amino acids can be deleted from any region of the polypeptide, including the carboxyl terminus and/or amino terminus, without substantial loss of biological function (Ron et al., *J. Biol. Chem.*, 268: 2984-2988 (1993); Dobeli et al., *J. Biotechnology*, 7: 199-216 (1988)). The amino acid substitution(s) can be conservative, non-conservative, or any combination thereof, as long as the ABC1 variant retains its biological activity. In addition, the substitution(s) can be with non-conserved amino acid residues, where the substituted residues may or may not be encoded by the genetic code, and with amino acid residues having a substituent group.

Suitable variants of ABC1 polypeptides can be determined using well-known techniques. For example, suitable ABC1 variants can be determined by identifying regions of the ABC1 molecule that may be changed without destroying biological activity. Also, as realized in the art, even regions that may be important for biological activity or for structure may be subject to conservative amino acid substitutions without destroying the biological activity or without adversely affecting the polypeptide structure. Amino acid residues that can be changed without destroying biological activity can be determined by identifying regions of the ABC1 polypeptide that are not important for activity (Bowie et al., *Science,* 247: 1306-1310 (1990)). For example, ABC1 polypeptides from various species can be compared to determine the amino acid residues and regions of ABC1 molecules that are conserved across species. The conserved amino acid residues are likely important for biological function and/or structure. In contrast, changes in regions of the ABC1 molecule that are not conserved across species and are thus tolerated by natural selection would be less likely to adversely affect biological activity and/or structure. Accordingly, ABC1 polypeptides with additions, deletions, or substitutions in the non-conserved regions are likely suitable variants. Even in relatively conserved regions, chemically similar amino acids may be substituted for the naturally occurring residues while retaining activity.

In addition, suitable ABC1 variants can be identified using structure-function studies to determine residues in other members of the ATP-binding cassette protein family, such as ABCR and ABC-C, that are important for activity or structure. Such studies allow the prediction of important amino acid residues in an ABC1 variant that correspond to amino acid residues that are important for activity or structure in other ATP-binding cassette proteins. For example, based on structure-function studies of other ATP-binding cassette proteins, important amino acid residues in ABC1 are likely found in regions associated with nucleotide binding and sterol transport. Suitable variants include, for example, polypeptides having chemically similar amino acid substitutions for such predicted important amino acid residues of the ABC1 polypeptide.

Suitable ABC1 variants can also be determined using genetic engineering techniques to introduce amino acid changes at specific positions in order to identify regions critical for polypeptide function. Amino acid changes can be made using, for example, site-directed mutagenesis or alanine-scanning mutagenesis (Cunningham et al., *Science,* 244: 1081-1085 (1989)). The resultant ABC1 variants can then be tested for biological activity using, for example, any one of the cholesterol efflux assays described herein. Variants having a particular amino acid residue substitution that results in destroyed cholesterol efflux activity would not be considered a suitable ABC1 variant.

Additional methods for identifying suitable variants are known in the art. Furthermore, one skilled in the art would realize amino acid changes that are likely to be permissive at certain amino acid positions in the protein (Bowie et al., supra (1990)). For example, it is generally known that the most buried or interior (within the tertiary structure of the protein) amino acid residues require nonpolar side chains, whereas fewer features of surface or exterior side chains are generally conserved. Moreover, it is known that tolerated conservative amino acid substitutions involve replacement of the aliphatic or hydrophobic amino acids Ala, Val, Leu and Ile, replacement of the hydroxyl residues Ser and Thr, replacement of the acidic residues Asp and Glu, replacement of the amide residues Asn and Gln, replacement of the basic residues Lys, Arg, and His, replacement of the aromatic residues Phe, Tyr, and Trp, and replacement of the small-sized amino acids Ala, Ser, Thr, Met, and Gly.

The ABC1 variants can be naturally-occurring or artificially constructed. Examples of naturally-occurring variants are allelic variants and splice variants. Allelic variants refer to one of several alternate forms of a gene occupying a given locus on a chromosome of an organism or population of organisms (Lewin, B., ed., *Genes II*, John Wiley & Sons, New York (1985)). Allelic variants can vary at either the polynucleotide and/or polypeptide level. Splice variants refer to a nucleic acid molecule, usually RNA, which is generated by alternative processing of intron sequences in an RNA transcript, and the corresponding polypeptide. Alternatively, the ABC1 variants can be artificially constructed. For example, ABC1 variants can be constructed using the technique of site-directed mutagenesis. Also, for example, ABC1 variants can be prepared from the corresponding nucleic acid molecules encoding said variants, which have a DNA sequence that varies as described from the wild-type DNA sequence as set forth in SEQ ID NO: 1.

Polypeptide fragments refer to polypeptides which comprise less than the full length amino acid sequence of ABC1 set forth in SEQ ID NO: 2. Preferred polypeptides fragments include those fragments that possess the biological activity of ABC1. In particular, those fragments that mediate reverse cholesterol transport or have improved reverse cholesterol transport activity are preferred. ABC1 fragments can have one or more amino acids deleted from any region of the polypeptide, including the carboxyl terminus and/or amino terminus, as long as biological function is maintained. The ABC1 polypeptide fragments can occur naturally, such through alternative splicing or in vivo protease activity, or can be artificially constructed using well-known methods.

The invention also relates to ABC1 polypeptide derivatives, which refer to ABC1 polypeptides, variants, or fragments, as defined herein, that have been chemically modified. The derivatives are modified in a manner that is different from naturally-occurring ABC1 polypeptides, either in type or location of the molecules attached to the polypeptide. Derivatives may further include polypeptides formed by the deletion of one or more chemical groups which are naturally attached to the ABC1 polypeptides. In addition, the ABC1 polypeptide comprising the amino acid sequence of SEQ ID NO: 2, as well as the above-described ABC1 variants and fragments, may be fused to a homologous polypeptide to form a homodimer or to a heterologous polypeptide to form a heterodimer.

Another aspect of the present invention relates to mutant ABC1 polypeptides and fragments thereof, corresponding to polypeptides isolated from Tangier patients. In one preferred embodiment, the ABC1 polypeptide comprises SEQ ID NO: 8. The protein was isolated from a Tangier patient (TD1) and sequenced as decribed in Examples 1 and 5. The amino acid sequence set forth in SEQ ID NO: 8 is similar to the wild-type sequence with the exception of a glutamine to arginine residue substitution at position 537 (the residue number is that of Lawn et al., *J. Clin. Invest.,* 104: r25-31 (1999), corresponding to position 597 of SEQ ID NO: 8). The location of this residue is within the amino-terminal hydrophilic domain, near the first predicted transmembrane domain. The substitution alters the charge of the amino acid in this region of the protein, resulting in an ABC1 protein that has significantly decreased cholesterol efflux activity, as shown in FIG. 1.

In another preferred embodiment, the mutant ABC1 polypeptide comprises SEQ ID NO: 10. The protein corresponds to a polypeptide isolated from a Tangier patient (TD2) and sequenced as decribed in Examples 1 and 5. The amino acid sequence set forth in SEQ ID NO: 10 is similar to the wild-type sequence with the exception of an arginine to tryptophan substitution at residue 527 (the residue number is that of Lawn et al., supra (1999), corresponding to position 587 of SEQ ID NO: 10). Like the TD1 polypeptide, this substitution alters the charge of the amino acid residue in the amino-terminal hydrophilic domain of the ABC1 protein. The resultant mutant ABC1 protein also has significantly decreased cholesterol efflux activity, as shown in FIG. 1.

ABC1 Polynucleotides

Another aspect of the present invention relates to isolated polynucleotides that encode the novel ABC1 polypeptides and variants thereof. The present invention provides, for example, isolated polynucleotides encoding the full-length ABC1 polypeptide, polynucleotides containing the full-lenth cDNA of wild-type ABC1, polynucleotides containing the entire length of the coding sequence of wild-type ABC1, and polynucleotides containing non-coding 5'and 3'sequences of ABC1, as well as polynucleotides of related ABC1 variants. The present invention also provides isolated polynucleotides that encode mutant ABC1 polypeptides, such as those of Tangier patients.

Figure 4:
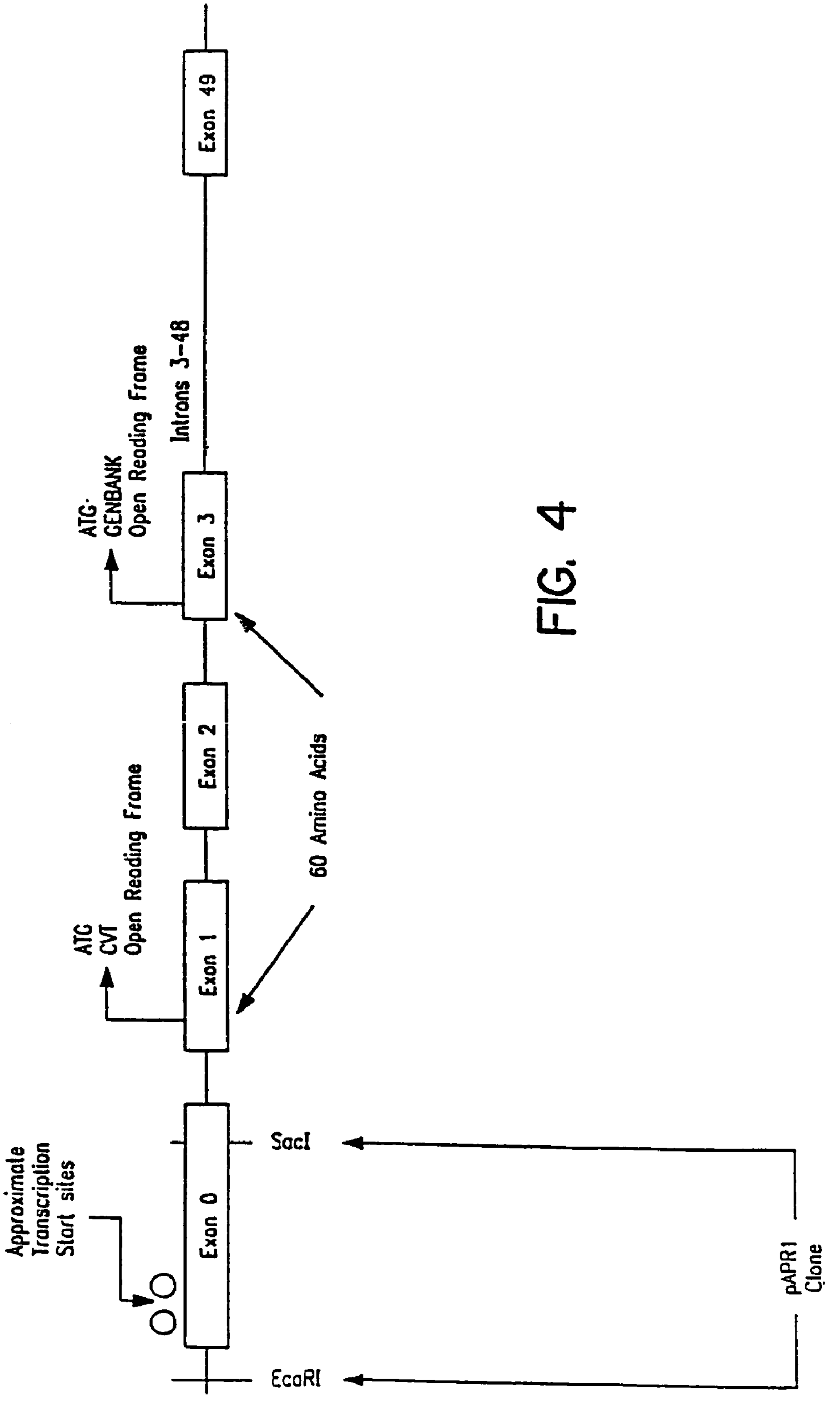
FIG. 4 is a schematic diagram of the gene structure of human ABC1, showing a comparison between the published human ABC1 amino acid sequence (GenBank, Accession #AJ012376) and the presently disclosed and claimed human ABC1 amino acid sequence ("CVT") which has sixty additional amino acids at the N-terminal end.

In one preferred embodiment, the isolated polynucleotide comprises a nucleotide sequence encoding the polypeptide comprising SEQ ID NO: 2. Importantly, in contrast to the published sequence of Langmann et al. which codes for a protein of 2201 amino acids based on a predicted start methionine found in exon 3 (Langmann et al., *Biochem. Biophys. Res. Comm.,* 257: 29-33 (1999) (GenBank Accession No. AJO12376), the presently claimed nucleotide sequence contains 50 exons and codes for a protein of 2261 amino acids (see FIG. 4). The corresponding nucleotide sequence of the present invention contains a coding sequence that includes an additional 180 nucleotides at the 5' end corresponding to the following 60 amino-terminal amino acids: MACWPQLRLLLWKNLTFRRRQTCQLLL-EVAWPLFIFLILISVRLSYPPYEQHECHFPNKA (SEQ ID NO: 58). Given that there is an in-frame stop codon 6 to 9 nucleotides upstream from this location, the newly predicted start site is the first methionine codon that could produce a continuous open reading frame. Alignment of this new ABC1 cDNA sequence with related ABC transporter sequences ABCR and ABC-C (also known as ABC3) which also contain open reading frames for the 60 additional amino acids, indicates a high degree of similarity, implying that the homologous ABC transporter proteins begin with sequences related to the amino terminal extension sequence proposed for human ABC1. It is likely that the earlier published start site of the human ABC1 was predicted from the published mouse ABC1 cDNA sequence (Luciani et al., *Genomics,* 21150-159 (1994); GenBank Accession no.: X75926) which contains an extra nucleotide "n" in the extension region such that the newly disclosed methionine is not in-frame. However, if the "n" nucleotide in the mouse sequence is ignored, the mouse and human sequences of the extension region are identical. In light of these results, it is likely that the full length human ABC1 protein contains 2261 amino acids rather than 2201 amino acids, as previously suggested by Langmann et al. and others. Accordingly, Langmann et al. do not present the full open reading frame of human ABC1.

In another preferred embodiment, the isolated polynucleotide comprises the full-lenth ABC1 cDNA, including at least a portion of either non-coding 5' and 3' sequences. Preferably, the polynucleotide comprises the nucleotide sequence shown in SEQ ID NO: 1. The 10.4 kb human ABC1 cDNA sequence shown in SEQ ID NO: 1 contains an open reading frame of 6783 nucleotides plus 5' and 3' untranslated regions. There is a start codon at position 291 and a stop codon at position 7074. The present ABC1 cDNA shown in SEQ ID NO: 1 differs from the published ABC1 cDNA (GenBank Accession No. AJO12376) in several respects. First, the present ABC1 cDNA includes an additional 350 nucleotides at the 5' end and an additional 3136 nucleotides at the 3' end (not including the poly(A) tail). The present ABC1 sequence also differs from the published ABC1 cDNA by the substitution of 10 nucleotides in the coding region. Of the ten differences, seven nucleotide differences predict amino acid changes. To remain consistent with published notation, the following nucleotide and amino acid numbers are those of Lawn et al., *J. Clin. Invest.,* 104: R25-31 (1999) and GenBank Accession No. AJO12376, rather than those of SEQ ID NO: 1. The nucleotide and amino acid changes are as follows: (1) A for G at nucleotide 414; (2) A for G at nucleotide 596 (K for R at amino acid 159); (3) T for C at nucleotide 705; (4) A for C at nucleotide 1980; (5) A for G at 2413 (I for V at amino acid 765); (6) G for A at 2589 (M for I at amino acid 823); (7) T for C at 4604 (I for T at anino acid 1495); (8) T for C at 4883 (L for P at amino acid 1588); (9) A for G at 5861 (K for R at amino acid 1914); and (10) T for C at 6443 (L for P at amino acid 2108). Five of the amino acid changes are conservative amino acid changes and may represent polymorphisms or sequence errors. In two instances, the present sequence predicts important amino acid differences from the GenBank sequence. The differences result in a leucine rather than a proline at residue 1588 and at residue 2108. Interestingly, at both positions, the predicted leucine was also found in each of the three TD samples analyzed as well as the highly conserved mouse ABC1 protein sequence.

The present invention also relates to ABC1 polynucleotides comprising nucleotide sequences that preferably have at least 80% identity over their entire length to the polynucleotide comprising SEQ ID NO: 1. More preferably, the polynucleotide has at least 90% identity over its entire length to the polynucleotide comprising SEQ ID NO: 1. Even more preferably, the polynucleotide has at least 95% identity over its entire length to the polynucleotide comprising SEQ ID NO: 1. Most preferably the polynucleotide has 100% identity over its entire length to the polynucleotide comprising SEQ ID NO: 1. Such related ABC1 polynucleotides include substitution, deletion, and insertion variants, as well as allelic variants, splice variants, fragments, derivatives, and orthologs, wherein one or more nucleotides have been substituted, deleted, inserted, or derivatized. Preferred polynucleotides include those polynucleotides that encode ABC1 polypeptides possessing biological activity, such as cholesterol efflux activity.

In another preferred embodiment, the isolated polynucleotide comprises the entire coding sequence of ABC1. In a particularly preferred embodiment, the polynucleotide comprises the sequence shown as nucleotides 291-7074 of SEQ ID NO: 1. This isolated polynucleotide contains an ABC1 open reading frame of 6783 nucleotides and encodes a polypeptide of 2261 amino acids, as described above.

In yet another preferred embodiment, the isolated polynucleotide comprises a nucleotide sequence that encodes an ABC1 variant polypeptide. In particular, the isolated polynucleotide comprises a nucleotide sequence that encodes a polypeptide comprising an amino acid sequence which is at least 98% identical to the amino acid sequence of SEQ ID NO: 2. Also preferred is an isolated polynucleotide comprising a nucleotide sequence that encodes a polypeptide comprising an amino acid sequence which is at least 99% identical to the amino acid sequence of SEQ ID NO: 2. Accordingly, the invention includes those polynucleotides that encode the above-described ABC1 polypeptides, including the described substitution, deletion, and insertion variants, as well as ABC1 allelic variants, splice variants, fragments, derivatives, fusion polypeptides, and orthologs. Preferred polynucleotides are those polynucleotides that encode polypeptides that possess the biological activity of ABC1. In particular, those polynucleotides that encode polypeptides that mediate reverse cholesterol transport are preferred. Also preferred are polynucleotides that enocode polypeptides that have improved reverse cholesterol transport activity.

Yet another aspect of the invention relates to isolated polynucleotides that encode mutant ABC1 polypeptides from Tangier patients. In one preferred embodiment, the polynucleotide encodes the polypeptide of SEQ ID NO: 8, which polypeptide is isolated from patient TD1 and is described above. In another preferred embodiment, the polynucleotide comprises the nucleotide sequence set forth in SEQ ID NO: 7. The nucleotide sequence set forth in SEQ ID NO: 7 contains the full open reading frame, as well as 5' and 3' flanking sequences. The open reading frame encodes a polypeptide of 2261 amino acids, containing, among other substitutions, a nucleotide substitution that results in an A to G substitution at position 537 (using the numbering of Lawn et al., supra (1999)).

In another preferred embodiment relating to polynucleotides that encode mutant ABC1 polypeptides, the polynucleotide encodes the polypeptide of SEQ ID NO: 10, which polypeptide is isolated from Tangier patient TD2 and is also described above. In yet another preferred embodiment, the polynucleotide comprises the nucleotide sequence set forth in SEQ ID NO: 9. The nucleotide sequence set forth in SEQ ID NO: 9 contains the full open reading frame, as well as 5' and 3' flanking sequences. The open reading frame encodes a polypeptide of 2261 amino acids, containing, among other substitutions, a polynucleotide substitution that results in an Arg to Tryp substitution at residue 527 (using the numbering of Lawn et al., supra (1999)).

Another aspect of the present invention relates to isolated polynucleotides that comprise the non-coding 5' flanking and 3' flanking regions of ABC1. In one embodiment, the isolated polynucleotide comprises the non-coding 5' flanking region of ABC1. Preferably, the 5' flanking region contains, but is not limited to, the ABC1 promoter region. Thus, in a preferred embodiment, the polynucleotide comprises the sequence shown in SEQ ID NO: 3. As demonstrated by heterologous reporter assays, discussed in Example 15, the polynucleotide set forth in SEQ ID NO: 3 contains the transcriptional regulatory region of the ABC1 gene. As shown in FIG. 13, the polynucleotide set forth in SEQ ID NO: 3 is a 1643 b.p. non-coding sequence that contains several transcription regulatory elements, including a TATA box at positions 1522, 1435, and 1383, as well as transcription factor binding sites, including several putative SPI sites, and several nuclear receptor half sites. In addition, an identified sterol response element is found at position 1483-1500. Further heterologous reporter assays described in Example 18 revealed that several discrete portions of SEQ ID NO: 3 retained promoter activity. Accordingly, in another preferred embodiment, the polynucleotide comprises nucleotides 1-1532, 1080-1643, 1181-1643, 1292-1643, or 1394-1643 of SEQ ID NO: 3. In an especially preferred embodiment, the polynucleotide comprises nucleotides 1394-1532 of SEQ ID NO: 3, which sequence has been shown to have ABC1 promoter activity (see Example 18). In yet another preferred embodiment, the polynucleotide comprises nucleotides 1480-1510 of SEQ ID NO: 3, which is shown to regulate the ABC1 transcriptional response to LXR ligands.

The 5' flanking polynucleotide also comprises a nucleotide sequence that hybridizes, under stringent conditions, to the nucleotide sequence set forth in SEQ ID NO: 3, wherein the nucleotide sequence has ABC1 promoter activity. In yet another embodiment, the polynucleotide comprises a nucleotide sequence that hybridizes, under stringent conditions, to the nucleotide sequence comprising nucleotides 1-1532, 1080-1643, 1181-1643, 1292-1643, or 1394-1643 of SEQ ID NO: 3, wherein the nucleotide sequence has ABC1 promoter activity.

In another embodiment, the isolated polynucleotide comprises the 3' flanking region of ABC1. Several 3' untranslated regions have been identified which may represent alternate sites of polyadenylation of the ABC1 transcript. Preferably, the 3' flanking region contains regulatory sequences. For example, the full length 3' UTR (SEQ ID NO: 6) contains 46 sequences (AA)nCU/UC(AA)n (SEQ ID NO: 59) which have been shown to be necessary for binding of Vigilin. Vigilin, a ubiquitous protein with 14K homology domains, is the estrogen-inducible vitellogenin mRNA 3' -untranslated region binding protein (*J. Biol. Chem.,* 272: 12249-12252 (1997)). In addition to binding HDL, Vigilin has been shown to bind to the 3' flanking region of mRNAs and to increase the half-life of the mRNA transcript (*Mol. Cell. Biol.,* 18:3991-4003 (1998)). Thus, the 3' flanking region could be altered, for example, to increase the binding of Vigilin, thereby increasing the half-life of the ABC1 mRNA. Preferably, the isolated polynucleotide comprises the sequence shown in SEQ ID NO: 4. Also preferably, the isolated polynucleotide comprises the sequence shown in SEQ ID NO: 5. In another preferred embodiment, the isolated polynucleotide comprises the sequence shown in SEQ ID NO: 6. In other preferred embodiments, the polynucleotide comprises a sequence that hybridizes, under stringent conditions, to the nucleotide sequence set forth in SEQ ID NO: 4, SEQ ID NO: 5, or SEQ ID NO: 6.

The present invention also includes related ABC1 5' and 3' flanking polynucleotides. Accordingly, the invention relates to polynucleotides comprising nucleotide sequences that have at least 80% identity over their entire length to the polynucleotide comprising SEQ ID NO: 3, the polynucleotide comprising SEQ ID NO: 4, the polynucleotide comprising SEQ ID NO: 5, the polynucleotide comprising SEQ ID NO: 6, or the polynucleotide comprising nucleotides 1-1532, 1080-1643, 1181-1643, 1292-1643, or 1394-1643 of SEQ ID NO: 3. Preferably, the polynucleotide has at least 80%, more preferably at least 90%, even more preferably at least 95%, and most preferably 100% identity over its entire length to any one of the aforementioned flanking polynucleotides. Preferred polynucleotides include those polynucleotides that possess biological activity, such as transcriptional regulatory activity.

It is understood that the present invention further relates to isolated polynucleotides that are complementary to any one of the above-described polynucleotide sequences. As used herein, the term "complementary" refers to the hybridization or base pairing between nucleotides, such as, for example, between the two strands of a double-stranded polynucleotide. Two single-stranded nucleotide molecules are said to be complementary when the nucleotides of one strand, optimally aligned with appropriate nucleotide insertions, deletions or substitutions, pair with at least about 80% of the nucleotides of the other strand.

Another aspect of the present invention relates to compositions comprising the novel ABC1 polynucleotides described above and a suitable carrier. In one embodiment, the composition comprises a polynucleotide encoding the polypeptide comprising SEQ ID NO: 2, a polynucleotide comprising SEQ ID NO: 1, a polynucleotide comprising nucleotides 291-7074 of SEQ ID NO: 1, or a polynucleotide encoding a polypeptide comprising an amino acid sequence which is at least 98% identical to the amino acid sequence of SEQ ID NO: 2 and a suitable carrier. In another embodiment, the composition comprises a polynucleotide having at least 80%, preferably 90%, or more preferably 95% identity over its entire length to the polynucleotide comprising SEQ ID NO: 1 and a suitable carrier.

In another embodiment, the composition comprises a polynucleotide comprising an ABC1 5' flanking sequence and a suitable carrier. Preferably, the composition comprises a polynucleotide comprising SEQ ID NO: 3 or a polynucleotide comprising nucleotide fragments 1-1532, 1080-1643, 1181-1643, 1292-1643, or 1394-1643 of SEQ ID NO: 3 and a suitable carrier. Also preferably, the composition comprises a polynucleotide having at least 80%, 90%, or 95% identity over its entire length to the polynucleotide comprising any one of the described 5' flanking sequences and a suitable carrier. In yet another embodiment, the composition comprises a polynucleotide comprising an ABC1 3' flanking sequence and a suitable carrier. Preferred compositions comprise a polynucleotide comprising SEQ ID NO: 4, a polynucleotide comprising SEQ ID NO: 5, or a polynucleotide comprising SEQ ID NO: 6, as well as a polynucleotide having at least 80%, preferably 90%, or more preferably 95% identity over its entire length to any of these polynucleotides, and a suitable carrier. Still other compositions of the invention comprise mutant ABC1 polynucleotides. Preferably, the composition comprises a polynucleotide comprising SEQ ID NO: 7 or a polynucleotide comprising SEQ ID NO: 9 and a suitable carrier.

In addition, a composition of the present invention may comprise, in any combination, two or more of the above-described ABC1 polynucleotides and a suitable carrier. Any suitable aqueous carrier can be used in the composition. Preferably, the carrier renders the composition stable at a desired temperature, such as room temperature or storage temperature (i.e. 4° C. to −20° C.), and is of approximately neutral pH. Examples of suitable carriers are known to those of skill in the art and include Tris-EDTA buffer and DEPC-$H_2O$.

ABC1 Vectors and Host Cells

The present invention also relates to recombinant vectors that comprise one or more of the above-described ABC1 polynucleotides, host cells that are genetically engineered with the vectors comprising ABC1 polynucleotides, and the production of ABC1 polypeptides by recombinant techniques. As mentioned, the invention provides recombinant vectors that comprise one or more of the above-described wild-type ABC1 polynucleotides. In preferred embodiments, the recombinant vector comprises the polynucleotide encoding the polypeptide comprising SEQ ID NO: 2, the polynucleotide comprising SEQ ID NO: 1, and the polynucleotide comprising nucleotides 291-7074 of SEQ ID NO: 1. In another preferred embodiment, the recombinant vector comprises the variant polynucleotide encoding a polypeptide comprising an amino acid sequence which is at least 98% identical to the amino acid sequence of SEQ ID NO: 2. Also, in another preferred embodiment, the recombinant vector comprises a variant polynucleotide that is at least 80% identical to a polynucleotide comprising SEQ ID NO: 1. In still another preferred embodiment, the recombinant vector comprises a polynucleotide that is complementary to any of these polynucleotides.

In another embodiment, the recombinant vector comprises a polynucleotide comprising a mutant ABC1 polynucleotide isolated from a Tangier disease patient. In a preferred embodiment, the recombinant vector comprises the polynucleotide comprising SEQ ID NO: 8. In another preferred embodiment, the recombinant vector comprises the polynucleotide comprising SEQ ID NO: 10. The recombinant vectors may also comprise a polynucleotide sequence that is complementary to these sequences.

It is also understood that the recombinant vector may also comprise, in any combination, two or more of the above-described wild-type, variant, or mutant ABC1 polynulceotides.

An isolated ABC1 polynucleotide, such as any of the above-described wild-type, variant, or mutant polynucleotides, is inserted into a vector using well-known ligation and cloning techniques. Cloning techniques have been described in several standard laboratory manuals, including Davis et al., *Basic Methods in Molecular Biology* (1986); Sambrook et al., *Molecular Cloning: A Laboratory Manual*, $2^{nd}$ Ed., (Cold Spring Harbor Press, Cold Spring Harbor, N.Y. (1989)); Ausubel et al. eds., *Current Protocols in Molecular Biology*, (Wiley and Sons (1994)); Goeddel, ed., *Gene Expression Technology* (Methods in Enzymology (1991)); Murray, ed., *Gene Transfer and Expression Protocols* (Human Press, Clifton, N.J.).

Any vector suitable for ABC1 polynucleotide insertion can be used. The vector is typically selected to be functional in the particular host cell employed (i.e., the vector is compatible with the host cell machinery such that amplification and/or expression of the gene can occur). Preferably, the vector is compatible with bacterial, insect, or mammalian host cells. Also preferably, the vector is an expression vector (for a review of expression vectors, see Goeddel, D. V. ed., *Methods Enzymol*., Academic Press Inc., San Diego, Calif. (1990)). The vector may be, for example, a phage, plasmid, viral, or retroviral vector. Retroviral vectors may be replication competent or replication defective. In the latter case, viral propagation generally will occur only in complementing host cells.

Typically, expression vectors used in any of the host cells will contain sequences for plasmid maintenance and for cloning and expression of exogenous nucleotide sequences. Such sequences, collectively referred to as “flanking sequences” should preferably include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

The flanking sequences may be homologous (i.e., from the same species and/or strain as the host cell), heterologous (i.e., from a species other than the host cell species or strain), hybrid (i.e., a combination of flanking sequences from more than one source), or synthetic. Also, the flanking sequences may be native sequences which normally function to regulate ABC1 polypeptide expression. The source of a flanking sequence may be any prokaryotic or eukaryotic organism, any vertebrate or invertebrate organism, or any plant, provided that the flanking sequence is functional in, and can be activated by, the host cell machinery.

The vector should also preferably include at least one selectable marker for propagation in a host. A selectable marker is a gene element that encodes a protein necessary for the survival and growth of a host cell grown in a selective culture medium. Suitable selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers include zeocin, G418, hygromycin, or neomycin resistence for eukaryotic cell culture and tetracycline, kanamycin, or ampicillin resistance for culturing in *E. coli* and other bacteria.

Other suitable selection genes include those that are used to amplify the expressed gene. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the ABC1 gene. As a result, increased quantities of ABC1 polypeptide are synthesized from the amplified DNA.

The vector should also preferably contain a transcription termination sequence, which is typically located 3' of the end of a polypeptide coding region and serves to terminate transcription. Usually, the transcription termination sequence in prokaryote cells is a G-C rich fragment followed by a poly T sequence. The sequence can be purchased as part of a commercial vector or synthesized using well-known methods for nucleic acid synthesis.

The vector should also preferably contain a ribosome binding site, which is usually necessary for translation initiation of mRNA and is characterized by a Shine-Dalgarno sequence (prokaryotes) or a Kozak sequence (eukaryotes). The element is typically located 3' to the promoter and 5' to the coding sequence of the ABC1 polypeptide to be expressed. The Shine-Dalgarno sequence is varied but is typically a polypurine (i.e., having a high A-G content). Many Shine-Dalgarno sequences have been identified, each of which can be readily synthesized using well-known methods.

The vector should also preferably contain a promoter that is recognized by the host organism and operably linked to the encoded polynucleotide. The promoter can be an inducible promoter or a constitutive promoter. Inducible promoters initiate increased levels of transcription from DNA under their control in response to some change in culture conditions, such as the presence or absence of a nutrient or a change in temperature. In contrast, constitutive promoters initiate continual gene product production; consequently there is little or no control over gene expression. A suitable promoter is operably linked to a polynucleotide, by removing the promoter from the source DNA by restriction enzyme digestion and inserting the desired promoter sequence into the vector. As mentioned, a native promoter can be used to direct amplification and/or expression of the polynucleotide. Thus, the recombinant vector can comprise any one of the above-described wild-type, variant, or mutant ABC1 polynulceotides and an ABC1 promoter, such as that found in SEQ ID NO: 3. The recombinant vector can also comprise, in any combination, two or more of the above-described wild-type, variant, or mutant ABC1 polynulceotides and an ABC1 promoter.

Preferably, a heterologous promoter is used if it permits greater transcription and higher yields of ABC1 protein as compared to the native ABC1 promoter, and if it is compatible with the host cell system that has been selected for use. The heterologous promoter can be used alone or in conjunction with the native ABC1 promoter. Thus, in one preferred embodiment, the recombinant vector comprises any one of the above-described wild-type ABC1 polynucleotides and a heterologous promoter. In another preferred embodiment, the recombinant vector comprises any one of the above-described variant ABC1 polynucleotides and a heterologous promoter. In yet another preferred embodiment, the recombinant vector comprises any one of the above-described mutant ABC1 polynucleotides and a heterologous promoter. Preferred embodiments also include recombinant vectors that contain any combination of two or more of the above-described wild-type, variant, and mutant ABC1 polynucleotides and a heterologous promoter.

Heterologous promoters suitable for use with prokaryotic hosts include, but are not limited to, the beta-lactamase and lactose promoter systems (Villa-Kamaroff et al., 1978, *Proc. Natl. Acad. Sci. U.S.A.,* 75:3727-31), alkaline phosphatase, a tryptophan (trp) promoter system, and hybrid promoters such as the tac promoter (Villa-Kamaroff et al., 1978, *Proc. Natl. Acad. Sci. U.S.A.,* 75:3727-31). Their sequences have been published, thereby enabling one skilled in the art to ligate them to the desired DNA sequence, using linkers or adapters as needed to supply any useful restriction sites. Other suitable heterologous promoters will be known to those skilled in the art.

Suitable heterologous promoters for use with mammalian host cells are also well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and Simian Virus 40 (SV40). Other suitable mammalian promoters include heterologous mammalian promoters, for example, heat-shock promoters and the actin promoter. Additional suitable promoters include, but are not limited to: the SV40 early promoter and late promoter region (Bernoist and Chambon, 1981, *Nature* 290:304-10); the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); and the regulatory sequences of the metallothionine gene (Brinster et al., 1982, *Nature* 296:39-42). Preferably, the promoter is a cytomegalovirus or SV40 promoter. Thus, in especially preferred embodiments, the recombinant vector comprises one of the above-described wild-type ABC1 polynucleotides, one of the above-described variant ABC1 polynucleotides, or one of the above-described mutant ABC1 polynucleotides and a cytomegalovirus promoter. In another especially preferred embodiment, the recombinant vector comprises, in any combination, two or more of the above-described wild-type, variant, or mutant ABC1 polynulceotides and a cytomegalovirus promoter.

The vector also preferably contains an enhancer sequence to increase the transcription of a polynucleotide, such as ABC1. Suitable enhancers for the activation of eukaryotic promoters include viral enhancers, such as the SV40, cytomegalovirus early promoter, polyoma, and adenovirus enhancers.

Expression vectors of the invention may be constructed from a starting vector, such as a commercially available vector, which may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors are those which are compatible with bacterial, insect, and mammalian host cells. Vectors preferred for use in bacteria include, for example, pQE70, pQE60, and pQE-9 (Quiagen, Inc.), pBluescript vectors, Phagescript vectors, pNH16A, pNH18A, pNH46A (Stratagene Cloning Systems, Inc.), ptrc99a, pKK223-3, pDR540, pRIT5 (Pharmacia Biotech, Inc.), and pCEP4 (Invitrogen Corp., Carlsbad, Calif.). Preferred eukaryotic vectors include, but are not limited to, pWLNEO, pSV2CAT, pOG44, pXTI and pSG (Stratagene), pSVK3, pBPV, pMSG, and pSVL (Pharmacia), and pGL3 (Promega, Madison, Wisc.). Other suitable vectors will be readily apparent to the skilled artisan.

Figure 3:
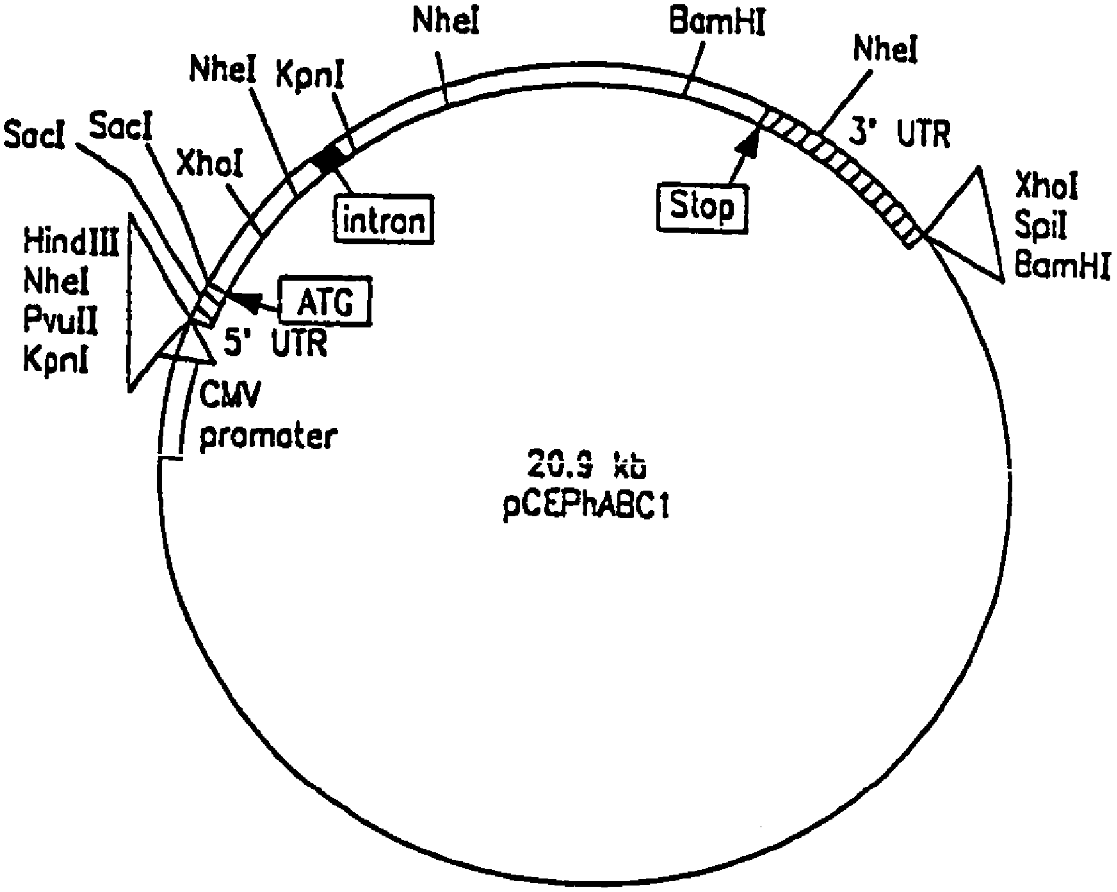
FIG. 3 is a schematic diagram showing a restriction map of the recombinant expression vector pCEPhABC1, which contains the open reading frame of the human ABC1 gene.

In an especially preferred embodiment, the recombinant vector comprises pCEPhABC1, which is described in Example 4 and shown in FIG. 3. The recombinant vector pCEPhABC1 comprises the plasmid pCEP4 (Invitrogen), an expression vector containing the cytomegalovirus promoter and enhancer. The vector pCEPhABC1 further comprises an ABC1 polynucleotide operatively linked to the heterologous cytomegalovirus promoter. The ABC1 polynucleotide comprises SEQ ID NO: 1, which contains the full-lenth ABC1 cDNA, including non-coding 5' flanking (i.e., native ABC1 promoter) and 3' flanking sequences.

In addition, the present invention provides recombinant vectors comprising ABC1 flanking sequence polynucleotides. In one embodiment, the recombinant vector comprises a polynucleotide comprising a ABC1 5' flanking sequence that preferably contains promoter activity. Thus, in a preferred embodiment, the recombinant vector comprises the polynucleotide comprising SEQ ID NO: 3. In another preferred embodiment, the recombinant vector comprises the polynucleotide comprising nucleotides 1-1532, 1080-1643, 1181-1643, 1292-1643, or 1394-1643 of SEQ ID NO: 3. In an especially preferred embodiment, the polynucleotide comprises nucleotides 1394-1532 of SEQ ID NO: 3. Also, in another embodiment, the recombinant vector comprises a polynucleotide that hybridizes, under stringent conditions, to the polynucleotide set forth in SEQ ID NO: 3 or the polynucleotide comprising nucleotides 1-1532, 1080-1643, 1181-1643, 1292-1643, or 1394-1643 of SEQ ID NO: 3. In yet another embodiment, the polynucleotide comprises a nucleotide sequence that has at least 80%, more preferably at least 90%, and even more preferably at least 95% identity over its entire length to the polynucleotide comprising SEQ ID NO: 3 or the polynucleotide comprising nucleotides 1-1532, 1080-1643, 1181-1643, 1292-1643, or 1394-1643 of SEQ ID NO: 3. The recombinant vector also comprises a polynucleotide that is complementary to any of the above-described 5' flanking sequences.

In another embodiment, the recombinant vector comprises a polynucleotide comprising a 3' flanking sequence of ABC1. In a preferred embodiment, the recombinant vector comprises the polynucleotide comprising SEQ ID NO: 4. In another preferred embodiment, the recombinant vector comprises the polynucleotide comprising SEQ ID NO: 5. In an equally preferred embodiment, the recombinant vector comprises the polynucleotide comprising SEQ ID NO: 6. Also, in another embodiment, the recombinant vector comprises a polynucleotide that hybridizes, under stringent conditions, to the polynucleotide set forth in SEQ ID NO: 4, SEQ ID NO: 5, or SEQ ID NO: 6. In yet another embodiment, the polynucleotide comprises a nucleotide sequence that has at least 80%, more preferably at least 90%, and even more preferably at least 95% identity over its entire length to the polynucleotide comprising SEQ ID NO: 4, SEQ ID NO: 5, or SEQ ID NO: 6. The recombinant vector also comprises a polynucleotide that is complementary to any of the above-described 3' flanking sequences.

An isolated ABC1 flanking sequence polynucleotide, such as any of the above-described 5' or 3' flanking sequence polynucleotides, is inserted into a vector using well-known ligation and cloning techniques. Any of the previously described vectors can be used. Preferably, the vector is compatible with bacterial, insect, or mammalian host cells. Also preferably, the vector is an expression vector. The vector may be, for example, a phage, plasmid, viral, or retroviral vector.

In addition to the ABC1 flanking sequence, the vector may contain one or more of the following flanking nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Any of the previously described flanking nucleotide sequences are suitable. The flanking sequences may be homologous, heterologous, hybrid, or synthetic. Also, the flanking sequences may be native sequences which normally function to regulate ABC1 polypeptide expression. The source of a flanking sequence may be any prokaryotic or eukaryotic organism, any vertebrate or invertebrate organism, or any plant, provided that the flanking sequence is functional in, and can be activated by, the host cell machinery.

Preferred vectors are those which are compatible with bacterial, insect, and mammalian host cells. Suitable vectors have been previously described and include pQE70, pQE60, pQE9, pBluescript vectors, Phagescript vectors, pNH16A, pNH18A, pNH46A, ptrc99a, pKK223-3, pDR540, pRIT5, and pCEP4 for use in bacteria and pWLNEO, pSV2CAT, pOG44, pXTI, pSG, pSVK3, pBPV, pMSG, pSVL, and pGL3 for use in eukaryotic cells.

In one particularly preferred embodiment, the recombinant vector comprises a polynucleotide comprising the 5' flanking region of the ABC1 gene and further comprises at least one polynucleotide encoding a heterologous polypeptide. The heterologous polynucleotide is operatively linked to the ABC1 5' flanking sequence. The ABC1 5' flanking sequence preferably contains the ABC1 promoter. Thus, preferably, the 5' flanking sequence comprises the sequence set forth in SEQ ID NO: 3. Equally preferably, the 5' flanking sequence comprises nucleotides 1-1532, 1080-1643, 1181-1643, 1292-1643, or 1394-1643 of SEQ ID NO: 3. The heterologous polynucleotide preferably encodes a polypeptide that is a complete protein or a biologically active fragment of a protein. The vector may also contain more than one heterologous polynucleotide. More preferably, the heterologous polynucleotide encodes a reporter protein. In such case, the recombinant vector preferably does not contain any additional promoter sequences. Examples of suitable reporter proteins include luciferase, β-galactosidase, chloramphenicol acetyl transferase transferase, and green fluorescent protein. Preferably, the reporter polypeptide is luciferase. Thus, in one especially preferred embodiment, the recombinant vector comprises the 5' flanking sequence set forth in SEQ ID NO: 3 and a luciferase reporter polynucleotide. In other equally preferred embodiments, the recombinant vector comprises a polynucleotide comprising nucleotides 1-1532, 1080-1643, 1181-1643, 1292-1643, or 1394-1643 of SEQ ID NO: 3 and a luciferase reporter polynucleotide.

Expression vectors comprising the ABC1 5' flanking sequence can be constructed from a starting vector, such as a commercially available vector, which contains a reporter polynucleotide. Examples of suitable expression vectors include pGL3-Basic, which contains a luciferase reporter gene (Promega, Madison, Wisc.) and pβGal-Basic (Clontech, Palo Alto, Calif.). A preferred vector is the pGL3-Basic luciferase reporter vector, which is promoterless. A 5' flanking sequence containing the ABC1 promoter, for example SEQ ID NO: 3, can be ligated into one of the above expression vectors using well-known methods, including the methods described herein (see Example 15). Thus, in an especially preferred embodiment, the recombinant vector is pAPR1, a reporter gene construct comprising SEQ ID NO: 3 and a luciferase reporter gene in a pGL3 vector (see FIG. 11).

The present invention also relates to host cells comprising any one of the above-described recombinant vectors. After the vector has been constructed, the completed vector can be inserted into a suitable host cell for amplification and/or polypeptide expression. Host cells may be prokaryotic host cells (such as *E. coli*) or eukaryotic host cells (such as a yeast cell, an insect cell, or a vertebrate cell). The host cell, when cultured under appropriate conditions, synthesizes an ABC1 polypeptide or, alternatively, a reporter polypeptide, which can be subsequently measured. The host cell can be a mammalian host cell, such as a primate cell line or a rodent cell line, including transformed cell lines. Normal diploid cells, cell strains derived from in vitro culture of primary tissue, as well as primary explants, are also suitable. Candidate host cells may be genotypically deficient in the selection gene, or may contain a dominantly acting selection gene.

A number of suitable host cells are known in the art and many are available from the American Type Culture Collection (ATCC), Manassas, Va. Suitable mammalian host cells include, but are not limited to, chinese hamster ovary cells (CHO), CO DHFR-cells (Urlaub et al., 1980, *Proc. Natl. Acad. Sci.,* 97:4216-20), human embryonic kidney (HEK) 293 or 293T cells, or 3T3 cells, monkey COS-1 and COS-7 cell lines, and the CV-1 cell line. Other suitable mammalian cell lines include but are not limited to, mouse neuroblastoma N2A cells, HeLa cells, mouse 1-929 cells, 3T3 lines derived from Swiss, Balb-c or NIH mice, BHK or HAK hamster cell lines, Thp-1, HepG2, and mouse RAW cell lines. Each of these cell lines is known by and available to those skilled in the art of protein expression. A preferred host cell is the mouse monocytic cell line RAW 264.7, which use is described in Example 8.

Suitable bacterial host cells include various strains of *E. coli* (e.g., HB101, DH50, DH10, and MC1061), which are well-known as host cells in the field of biotechnology. Various strains of *B. subtilis, Pseudomonas* spp., other *Bacillus* spp., *Streptomyces* spp., and the like may also be employed in this method. Also, many strains of yeast cells are also available as host cells for the expression of ABC1 polypeptides. Preferred yeast cells include, for example, *Saccharomyces cerivisae* and *Pichia pastoris*. Additionally, insect cell systems may be suitable host cells. Insect cell systems are described, for example, in Kitts et al., 1993, *Biotechniques,* 14:810-17; Lucklow, 1993, *Curr. Opin. Biotechnol.* 4:564-72; and Lucklow et al., 1993, *J. Virol.,* 67:4566-79. Preferred insect cells are Sf-9 and Hi5 (Invitrogen).

The present invention also provides a method for expressing an ABC1 protein in a mammalian host cell comprising the steps of: (a) transfecting the mammalian host cell with a recombinant expression vector comprising a polynucleotide encoding ABC1 in an amount sufficient to produce a detectable level of ABC1 protein; and (b) purifying the produced ABC1 protein. In one preferred embodiment, the recombinant expression vector comprises a polynucleotide encoding the polypeptide comprising SEQ ID NO: 2. In another preferred embodiment, the polynucleotide comprising SEQ ID NO: 1. In yet another preferred embodiment, the polynucleotide comprising nucleotides 291-7074 of SEQ ID NO: 1. In still another preferred embodiment, the polynucleotide encoding a polypeptide that is at least 98% identical to the polypeptide comprising SEQ ID NO: 2.

Introduction of the recombinant ABC1 vector into a mammalian host cell can be effected by methods well-known in the art and described in standard laboratory manuals, such as Sambrook, supra. Preferably, the recombinant vector is introduced into a host cell in a precipitate or in a complex with a charged lipid. Suitable methods for introduction of the ABC1 vector include calcium phosphate transfection, DEAE-dextran mediated transfection, cationic lipid-mediated transfection, electroporation, transduction, infection, or other methods known in the art. These methods are described, for example, in Davis et al., *Basic Methods in Molecular Biology* (1986). If the recombinant ABC1 vector is a viral vector, it may be packaged in vitro using an appropriate packaging cell line and then transduced into host cells.

The ABC1 polypeptide can be recovered and purified from recombinant cell cultures using well-known methods, including ammonium sulfate or ethanol precipitation, acid, extraction, anion or cation exchange chromatography, phosphocellulose chromatography, hydrophobic interaction chromatography, affinity chromatography, hydroxylapatite chromatoraphy, and lectin chromatography (see, e.g., Smith and Johnson, *Gene* 67:31-40 (1988)). Preferably, affinity chromotography using anti-ABC1 antibodies is employed for purification.

In addition, the present invention provides a method for expressing ABC1 protein in a mammalian subject comprising the step of administering to a mammalian subject a recombinant expression vector comprising a polynucleotide encoding ABC1 in an amount sufficient to express ABC1 protein in said mammalian subject. Preferably, the recombinant expression vector comprises a polynucleotide encoding the polypeptide comprising SEQ ID NO: 2, the polynucleotide comprising SEQ ID NO: 1, the polynucleotide comprising nucleotides 291-7074 of SEQ ID NO: 1, or the polynucleotide encoding a polypeptide that is at least 98% identical to the polypeptide comprising SEQ ID NO: 2. Introduction of the recombinant ABC1 vector into a mammalian subject can be effected by methods well-known in the art and are described in detail herein below. Expression of ABC1 can be measured by obtaining a blood sample from the subject to whom the recombinant ABC1 vector was administered, separating the monocyte population, and measuring the ABC1 gene expression in macrophage cells. The ABC1 gene expression can be measured using methods well-known in the art, such as RT-PCR, and methods described herein (see Examples 9 and 10). The level of ABC1 protein can be measured by obtaining a blood sample from the subject, separating the monocyte population and measuring the ABC1 protein in macrophage cells using well-known methods, such as immunoprecipitation, described herein at Example 11.

Methods and Compounds for Increasing Cholesterol Efflux

In another aspect of the present invention, a method suitable for increasing cholesterol efflux from cells in a mammalian subject is provided. Such method comprises administering to the mammalian subject a recombinant expression vector comprising an ABC1 polynucleotide in an amount sufficient to increase cholesterol efflux from said cells. The recombinant vector can be any of the above-described vectors containing any of the previously described wild-type or variant ABC1 polynucleotides, as long as the encoded ABC1 polypeptide has biological activity (i.e., cholesterol transport activity). Preferably, the recombinant vector comprises the polynucleotide encoding the polypeptide comprising SEQ ID NO: 2, the polynucleotide comprising SEQ ID NO: 1, the polynucleotide comprising nucleotides 291-7074 of SEQ ID NO: 1, or the polynucleotide encoding a polypeptide comprising an amino acid sequence which is at least 98% identical to the amino acid sequence of SEQ ID NO: 2. Also, preferably, the recombinant vector comprises a variant polynucleotide that is at least 80%, 90%, or 95% identical to the polynucleotide comprising SEQ ID NO: 1, as long as the encoded ABC1 polypeptide has cholesterol transport activity.

The administration of a recombinant ABC1 expression vector to a mammalian subject can be used to express the ABC1 gene in said subject for the treatment of cardiovascular disease. Specifically, this method would achieve its therapeutic effect by the introduction of the ABC1 gene into macrophage cells and other cholesterol-accumulating cells found in the arterial lesions of mammals with cardiovascular disease. Expression of the ABC1 polynucleotide in target cells would effect greater production of the ABC1 protein. The subsequently produced ABC1 protein would ameliorate the disease by increasing the efflux of cholesterol from macrophage and other cholesterol-laden cells found in arterial lesions onto nascent HDL particles. The cellular efflux would lead to the overall removal of cholesterol from peripheral sites, such as the cholesterol-rich core of arterial plaques. A concurrent reduction in the size of these pathological lesions reduces the risk of arterial blockage that leads to heart attacks and angina. This method could also be used prophylactically to prevent the accumulation of cholesterol in arterial walls.

A sufficient amount of ABC1 expression vector is the amount of ABC1 vector that increases cholesterol efflux from the cells of a mammalian subject. Such amount can be determined by measuring the cholesterol efflux in the cells of a subject before (control level) and after administration of the recombinant ABC1 expression vector at various dosages and determining the dose that effects an increase in cholesterol efflux compared to control level. The cholesterol efflux can be measured by obtaining a blood sample from the subject, separating the monocyte population, and measuring the amount of cholesterol efflux in a subject's macrophage cells. Any of the assays described herein can be used to measure cholesterol efflux.

In addition, cholesterol efflux can be measured by determining the level of plasma HDL-cholesterol in a subject before (control) and after administration of a recombinant ABC1 expression vector. An observed increase in HDL-cholesterol in the serum of a subject following administration of a recombinant ABC1 expression vector indicates an increase in cholesterol efflux. HDL-cholesterol levels in serum can be determined using methods well-known in the art.

In addition, cholesterol efflux can be measured by measuring the size of atherosclerotic lesions found in the arterial wall of a subject before (control level) and after administration of the recombinant ABC1 expression vector. A reduction in the size of the arterial lesion indicates an increase in cholesterol efflux. Assays for measuring arterial lesions are well known in the art. For example, increased cholesterol efflux from arterial lesions can be measured using the mouse model of atherosclerosis described in Lawn et al., *Nature,* 360: 670-672 (1992)), as well as any of the other known models. Using the LDL receptor knockout mouse described in Lawn et al., cholesterol efflux can be measured before and after administration of the ABC1 vector. Fatty streak lesion size in groups of animals fed an atherogenic diet can be measured by oil-red O staining of aortic sections as described in Lawn et al. A reduction in size of fatty streak lesions in the group receiving the ABC1 expression vector compared to a group receiving a control vector indicates an increase in cholesterol efflux from the lesions. In humans, the size of atherosclerotic lesions found in arterial walls can be measured using, for example, angiography and non-invasive ultrasound methods.

Alternatively, cholesterol efflux can be measured by obtaining a blood sample and measuring the level of ABC1 mRNA or ABC1 protein in the macrophage cells of a subject before and after administration of a recombinant ABC1 expression vector. Routine assays can be performed to determine the correlation between increasing ABC1 mRNA concentrations and cholesterol efflux. Likewise, assays can be performed to correlate the amount of ABC1 protein with the amount of cholesterol efflux. Using such correlation data, an observed increase in ABC1 mRNA or ABC1 protein in the cells of a subject following administration of a recombinant ABC1 expression vector can be used to indicate an increase in cholesterol efflux. ABC1 mRNA and ABC1 protein levels can be measured using the assays described herein and other well-known techniques for mRNA and protein quantitation. Therapeutic dosages and formulations are discussed in further detail below.

There are available to one skilled in the art multiple viral and non-viral methods suitable for introduction of a nucleic acid molecule into a target cell. For example, viral delivery vectors suitable for gene therapy include, but are not limited to, adenovirus, herpes simplex virus, pox virus (i.e., vaccinia), hepatitis virus, parvovirus, papovavirus, alphavirus, coronavirus, rhabdovirus, papilloma virus, adeno-associated virus (AAV), polio virus, and RNA viruses, such as a retroviruses and Sindbis virus. The ABC1 polynucleotide can also be delivered using a non-viral delivery system, such as naked DNA delivery (direct injection), receptor-mediated transfer (DNA-ligand complexes), electroporation, adenovirus-ligand-DNA complexes, calcium phosphate ($CaPO_4$) precipitation, microparticle bombardment (gene gun techniques), liposome-mediated transfer, and lipofection.

Genetic modification of a cell may be accomplished using one or more techniques well known in the gene therapy field (Mulligan, R., 1993, *Science,* 260 (5110): 926-32). Gene therapy materials and methods can include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Examples of methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

Adenoviral vectors have proven especially useful for gene transfer into eukaryotic cells (Rosenfeld, M., et al., *Science,* 252: 431-4 (1991); U.S. Pat. No. 5,631,236). The first trial of Ad-mediated gene therapy in human was the transfer of the cystic fibrosis transmembrane conductance regulator (CFTR) gene to lung (Crystal, R., et al., 1994, *Nat. Genet.,* 8 (1): 42-51). Experimental routes for administrating recombinant Ad to different tissues in vivo have included intratracheal instillation (Rosenfeld, M., et al., 1992, *Cell,* 68 (1): 143-55) injection into muscle (Quantin, B., et al., 1992, *Proc. Natl. Acad. Sci. U.S.A.,* 89 (7): 2581-4), peripheral intravenous injection (Herz, J., and Gerard, R., 1993, *Proc. Natl. Acad. Sci. U.S.A.,* 90 (7): 2812-6) and stereotactic inoculation to brain (Le Gal La Salle, G., et al., 1993, *Science,* 259 (5097): 988-90). The adenoviral vector, then, is widely available to one skilled in the art and is suitable for use in the present invention.

Adeno-associated virus (AAV) has recently been introduced as a gene transfer system with potential applications in gene therapy. Wild-type AAV demonstrates high-level infectivity, broad host range and specificity in integrating into the host cell genome (Hermonat, P., and Muzyczka, N., 1984, *Proc. Natl. Acad. Sci. U.S.A.,* 81 (20): 6466-70). Herpes simplex virus type-1 (HSV-1) is a preferred vector system (Geller, A., et al., 1991, *Trends Neurosci.,* 14 (10): 428-32; Glorioso, J., et al., 1995, *Mol. Biotechnol.,* 4 (1): 87-99; Glorioso, J., et al., *Annu. Rev. Microbiol.,* 49: 675-710). Vaccinia virus, of the poxvirus family, has also been developed as an expression vector (Smith, G., and Moss, B., 1983, *Gene,* 25 (1): 21-8; Moss, B., 1992, *Biotechnology,* 20: 345-62; Moss, B., 1992, *Curr. Top. Microbiol. Immunol.,* 158: 25-38). Each of the above-described vectors is widely available to one skilled in the art and would be suitable for use in the present invention.

Preferably, the viral delivery system utilizes a retroviral vector. Retroviral vectors are capable of infecting a large percentage of the target cells and integrating into the cell genome (Miller, A., and Rosman, G., *Biotechniques,* 7(9): 980-2, 984-6, 989-90 (1989); U.S. Pat. No. 5,672,510). Retroviruses were developed as gene transfer vectors relatively earlier than other viruses, and were first used successfully for gene marking and transducing the cDNA of adenosine deaminase (ADA) into human lymphocytes. Preferably, the retroviral vector is a derivative of a murine or avian retrovirus, or is a lentiviral vector. An especially preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. The helper plasmids are missing a nucleotide sequence that enables the packaging mechanism to recognize an RNA transcript for encapsitation. Thus, helper cell lines produce empty virions, since no genome is packaged. Suitable helper cell lines include, but are not limited to Ψ2, PA317 and PA12. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991, Academic Press, San Diego, Calif.), and *PCR Protocols: A Guide to Methods and Applications* (Innis, et al. 1990, Academic Press, San Diego, Calif.).

In order to obtain transcription of the ABC1 polynucleotide within a target cell, a transcriptional regulatory region capable of driving gene expression in the target cell must be utilized. The transcriptional regulatory region preferably comprises a promoter and/or enhancer, which is operatively linked to the ABC1 polynulceotide. The promoter can be homologous or heterologous to the ABC1 gene, provided that it is active in the cell or tissue-type into which the construct will be inserted. The transcriptional regulatory region chosen should drive high level gene expression in the target cell. Preferably, a macrophage-specific promoter, such as a scavenger receptor type A, matrix metalloproteinase promoter (MMP-12), or macrophage-tropic lentivirus promoter (Fabunmi et al., *Atherosclerosis,* 148: 375-386 (1999)), is used. A particularly preferred promoter is the 5' region of the scavenger receptor type A gene, which contains a strong macrophage promoter that can be used to drive the transcription of the ABC1 gene. In addition, a means to increase endogenous ABC1 polypeptide expression in a cell is to insert one or more enhancer elements into the promoter region, where the enhancer elements can serve to increase transcriptional activity of the ABC1 gene. Similarly, the enhancer element(s) used is selected based on the tissue in which one desires to activate the gene. Thus, for example, enhancer elements known to confer promoter activation in cells found in arterial tissue, especially macrophage cells, will be selected. Other transcriptional regulatory regions suitable for use in the present invention include but are not limited to the human cytomegalovirus (CMV) immediate-early enhancer/promoter, the SV40 early enhancer/promoter, the JC polyomavirus promoter, the albumin promoter, PGK and the α-actin promoter coupled to the CMV enhancer (Doll, R., et al., 1996, *Gene Ther.,* 3 (5): 437-47).

Other components of the vector construct may optionally include DNA molecules designed for site-specific integration (e.g., endogenous sequences useful for homologous recombination), tissue-specific promoters, DNA molecules capable of providing a selective advantage over the parent cell, DNA molecules useful as labels to identify transformed cells, negative selection systems, cell specific binding agents (e.g., for cell targeting), cell-specific internalization factors, transcription factors enhancing expression from a vector, and factors enabling vector production.

In one embodiment, the vector can include targeting DNA for site-specific integration. The targeting DNA is a nucleotide sequence that is complementary (homologous) to a region of the gene of interest, for example, the ABC1 gene. Through homologous recombination, the DNA sequence to be inserted into the genome can be directed to the ABC1 gene by attaching it to the targeting DNA. DNA sequences for insertion include, for example, regions of DNA that may interact with or control the expression of an ABC1 polypeptide, e.g., flanking sequences. Thus, the expression of the desired ABC1 polypeptide is achieved not by transfection of DNA that encodes the ABC1 gene itself, but rather by the use of targeting DNA coupled with DNA regulatory segments that provide the endogenous gene sequence with recognizable signals for transcription of an ABC1 polypeptide (Sauer, *Curr. Opin. Biotechnol.,* 5:521-27 (1994); Sauer, *Methods Enzymol.,* 225:890-900 (1993)).

In yet other embodiments, regulatory elements can be included for the controlled expression of the ABC1 gene in the target cell. Such elements are turned on in response to an appropriate effector. In this way, a therapeutic ABC1 polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene. Another suitable control means or gene switches includes the use of mifepristone (RU486), which is a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337. Yet another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168. Additional expression control systems and nucleic acid constructs are described in U.S. Pat. Nos. 5,741,679 and 5,834,186.

Viral delivery vectors containing an ABC1 polynucleotide can be made target specific by altering the viral coat such that it contains a ligand that is specific for another molecule found on the target cell. This will allow the vector to bind specifically to the desired cell-type. The ligand can be any compound of interest that will bind specifically to a molecule found on the target cell, such as a cell-surface receptor. Preferably, the receptor is found exclusively on target cells and not on other cells. For example, ligands for scavenger receptor A can be used to direct viral delivery vectors to macrophage cells. Alternatively, the viral coat can be altered such that it contains an antibody or antibody fragment, such as Fab, or $F(ab')_2$, that recognizes and binds to an antigenic epitope on the target cells. The viral coat can be altered by inserting an additional polynucleotide that encodes the ligand into the viral genome. Those of skill in the art will know of other specific polynucleotide sequences which can be inserted into the viral genome to allow target specific delivery of the vector containing the ABC1 polynucleotide.

In addition, a naked ABC1 polynucleotide can be administered. ABC1 polynucleotides and recombinant ABC1 expression vectors, such as those described above, can be administered as a pharmaceutical composition. Such a composition comprises an effective amount of an ABC1 polynucleotide or recombinant ABC1 expression vector, as previously defined herein, and a pharmaceutically acceptable formulation agent selected for suitability with the mode of administration. Suitable formulation materials preferably are non-toxic to recipients at the concentrations employed and are described herein below.

The pharmaceutical composition comprising an ABC1 polynucleotide or an ABC1 recombinant expression vector may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences (*$18^{th}$ Ed., A. R. Gennaro, ed., Mack Publishing Company 1990).

The pharmaceutically active compounds (i.e. ABC1 polynucleotide or ABC1 vector) can be processed in accordance with conventional methods of pharmacy to produce medicinal agents for administration to patients, including humans and other mammals. Thus, the pharmaceutical composition comprising an ABC1 polynucleotide or an ABC1 recombinant expression vector may be made up in a solid form (including granules, powders or suppositories) or in a liquid form (e.g., solutions, suspensions, or emulsions). Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral or parenteral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents. For example, a suitable carrier for injection may be water, physiological saline solution, or artificial cerebrospinal fluid, possibly supplemented with other materials common in compositions for parenteral administration. Neutral buffered saline or saline mixed with serum albumin are further exemplary carriers. Other exemplary pharmaceutical compositions comprise Tris buffer of about pH 7.0-8.5, or acetate buffer of about pH 4.0-5.5, which may further include sorbitol or a suitable substitute.

The dosage regimen for treating a cardiovascular disease with a composition comprising an ABC1 polynucleotide or ABC1 expression vector is based on a variety of factors, including the type of cardiovascular disease, the age, weight, sex, medical condition of the patient, the severity of the condition, the route of administration, and the particular compound employed. Thus, the dosage regimen may vary widely, but can be determined routinely using standard methods. For example, the amount of ABC1 polynucleotide or ABC1 expression vector to be administered is an amount sufficient to increase cholesterol efflux from the cells of a mammalian subject. Such amount can be determined, for example, by measuring the plasma HDL-cholesterol level of a subject before and after administration of the ABC1 polynucleotide or ABC1 expression vector. A sufficient amount of ABC1 polynucleotide or ABC1 expression vector is an amount that increases the plasma HDL-cholesterol level of a subject. Accordingly, the clinician can titer the dosage and modify the route of administration to obtain the optimal therapeutic effect. A typical dosage may range from about 0.1 g/kg to about 100 mg/kg or more, depending on the factors mentioned above.

The frequency of dosing will depend upon the pharmacokinetic parameters of the ABC1 polynucleotide or vector in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data.

The cells of a mammalian subject may be transfected in vivo, ex vivo, or in vitro. Administration of an ABC1 polynucleotide or a recombinant vector containing an ABC1 polynucleotide to a target cell in vivo may be accomplished using any of a variety of techniques well known to those skilled in the art. For example, U.S. Pat. No. 5,672,344 describes an in vivo viral-mediated gene transfer system involving a recombinant neurotrophic HSV-1 vector. The above-described compositions of ABC1 polynucleotides and recombinant ABC1 vectors can be transfected in vivo by oral, buccal, parenteral, rectal, or topical administration as well as by inhalation spray. The term "parenteral" as used herein includes, subcutaneous, intravenous, intramuscular, intrasternal, infusion techniques or intraperitoneally.

For oral administration, the pharmaceutical composition containing the ABC1 polynucleotide or recombinant ABC1 vector may be in the form of, for example, a capsule, a tablet, a suspension, or liquid. The pharmaceutical composition is preferably made in the form of a dosage unit containing a given amount of DNA or viral vector particles. For example, these may contain an amount from about $10^3$-$10^{15}$ viral particles, preferably from about $10^6$-$10^{12}$ viral particles. A suitable daily dose for a human or other mammal may vary widely depending on the condition of the patient and other factors, but, once again, can be determined using routine methods.

The pharmaceutical composition containing the ABC1 DNA or recombinant ABC1 vector can also be administered rectally. Suitable suppositories for rectal administration of the vector can be prepared by mixing the vector with a suitable non-irritating excipient such as cocoa butter and polyethylene glycols that are solid at ordinary temperatures but liquid at the rectal temperature and will therefore melt in the rectum and release the vector.

A pharmaceutical composition also can be formulated for inhalation. For example, an ABC1 polynucleotide or vector may be formulated as a dry powder for inhalation. Also, ABC1 polynucleotide or vector inhalation solutions can be formulated with a propellant for aerosol delivery. In yet another embodiment, solutions may be nebulized.

The pharmaceutical composition containing the ABC1 DNA or recombinant ABC1 vector can also be injected. Injectable preparations, such as sterile injectable aqueous or oleaginous suspensions, may be formulated according to the known methods using suitable dispersing or wetting agents and suspending agents. The sterile injectable preparation may also be a sterile injectable solution or suspension in a non-toxic parenterally acceptable diluent or solvent, for example as a solution in 1,3-butanediol. A particularly suitable carrier for parenteral injection is sterile distilled water in which an ABC1 polynucleotide or vector is formulated as a sterile, isotonic solution, properly preserved. Among the other acceptable carriers and solvents that may be employed are Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables. Yet another preparation can involve the formulation of the desired ABC1 molecule with an agent, such as injectable microsperes, bio-erodible particles, polymeric compounds, beads or liposomes, that provides for the controlled or sustained release of the ABC1 product (see, e.g. PCT/US93/00829; Eppstein et al., *Proc. Natl. Acad. Sci.,* 82: 3688-3692 (1985)).

Also, the pharmaceutical composition containing the ABC1 DNA or recombinant ABC1 vector can administered topically. For topical administration, the vector may comprise from 0.001% to 10% w/w, e.g., from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a vector of the present invention is administered one to four, preferably two or three times daily.

While the nucleic acids and/or vectors of the invention can be administered as the sole active pharmaceutical agent, they can also be used in combination with one or more vectors of the invention or other agents. When administered as a combination, the therapeutic agents can be formulated as separate compositions that are given at the same time or different times, or the therapeutic agents can be given as a single composition.

In another embodiment of the present invention, a target cell is transfected in vivo by implantation of a "producer cell line" in proximity to the target cell population (Culver, K., et al., 1994, *Hum. Gene Ther.,* 5 (3): 343-79; Culver, K., et al., *Cold Spring Harb. Symp. Quant. Biol.,* 59: 685-90; Oldfield, E., 1993, *Hum. Gene Ther.,* 4 (1): 39-69). The producer cell line is engineered to produce a viral vector containing the ABC1 polynucleotide and to release its viral particles in the vicinity of the target cells, i.e. preferably macrophage cells found in atherosclerotic lesions. A portion of the released viral particles contact the target macrophage cells and infect those cells, thus delivering an ABC1 polynucleotide to the target macrophage cell. Following infection of the target cell, expression of the ABC1 polynucleotide occurs, providing the macrophage cell with functional ABC1 protein.

In another embodiment, the invention provides a method of treating a cardiovascular disease by the ex vivo introduction of an ABC1 polynucleotide or recombinant ABC1 expression vector. In such instances, cells, tissues, or organs that have been removed from the patient are exposed to ABC1 compositions after which the cells, tissues, or organs are subsequently implanted back into the patient. For example, one method includes the removal of a blood sample from a subject with cardiovascular disease, enriching the sample for monocytes, and contacting the isolated monocytes with a recombinant expression vector containing the ABC1 polynucleotide and, optionally, a target specific gene. Optionally, the monocyte cells can be treated with a growth factor, such as GM-CSF, to stimulate cell growth, before reintroducing the cells into the subject. When reintroduced, the cells will specifically target the cell population from which they were originally isolated. In this way, the transport activity of the ABC1 polypeptide may be used to promote cholesterol efflux in a subject.

Another method of ex vivo administration involves introducing the ABC1 polynucleotide or recombinant ABC1 vector into the mammalian subject by means of skin transplants of cells containing the virus. Preferably, a retrovius used for this method of administration. Long term expression of foreign genes in implants, using cells of fibroblast origin, may be achieved if a strong housekeeping gene promoter is used to drive transcription. For example, the dihydrofolate reductase (DHFR) gene promoter may be used. Cells such as fibroblasts, can be infected with virions containing a retroviral construct containing the ABC1 polynucleotide together with a gene which allows for specific targeting, such as scavenger receptor A, and a strong promoter. The infected cells can be embedded in a collagen matrix that can be grafted into the connective tissue of the dermis in the recipient subject. As the retrovirus proliferates and escapes the matrix it will specifically infect the target cell population. In this way the transplantation results in increased amounts of cholesterol efflux activity in cells manifesting the transport disorder.

In another embodiment, the recombinant expression vector comprising the ABC1 polynucleotide can be administered using in vitro techniques, such as described in U.S. Pat. No. 5,399,346. For example, an ABC1 polypeptide can be delivered by implanting certain cells that have been genetically engineered, using methods such as those described herein, to express the ABC1 polypeptide. In order to minimize a potential immunological reaction in patients being administered an ABC1 polypeptide, as may occur with the administration of a polypeptide of a foreign species, it is preferred that the natural cells producing ABC1 polypeptide be of human origin and produce human ABC1 polypeptide. Thus, it is preferred that the recombinant cells producing ABC1 polypeptide be transformed with an expression vector containing a gene encoding a human ABC1 polypeptide. The cells can be autologous or heterologous. Optionally, the cells can be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues. The transfected cells can be administered to a patient using the above-described methods.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

Another delivery system for polynucleotides encoding ABC1 is a "non-viral" delivery system. Techniques that have been used or proposed for gene therapy include DNA-ligand complexes, adenovirus-ligand-DNA complexes, direct injection of DNA, $CaPO_4$ precipitation, gene gun techniques, electroporation, lipofection, and colloidal dispersion (Mulligan, R., 1993, *Science,* 260 (5110): 926-32). Any of these methods are widely available to one skilled in the art and would be suitable for use in the present invention. Other suitable methods are available to one skilled in the art, and it is to be understood that the present invention may be accomplished using any of the available methods of transfection. Several such methodologies have been utilized by those skilled in the art with varying success (Mulligan, R., 1993, *Science,* 260 (5110): 926-32).

Preferably, the non-viral delivery system is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which is an artificial membrane vesicle useful as delivery vehicles in vitro and in vivo. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule. For example, it has been shown that large unilamellar vesicles (LUV), which range in size from 0.2-4.0 μm can encapsulate a substantial percentage of an aqueous buffer containing large macromolecules, such as RNA, DNA and intact virions. Once encapsulated within the aqueous interior, these macromolecules can be delivered to mammalian cells in a biologically active form (Fraley, R. and Papahadjopoulos, D. 1981, *Trends Biochem. Sci.,* 6: 77-80). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, R., et al., 1988, *Biotechniques,* 6 (7): 682-90).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidyletha-nolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand, such as a polyclonal or monoclonal antibody, sugar, glycolipid, or protein, or by changing the composition or size of the liposome in order to achieve targeting to organs and cell types other than the naturally occurring sites of localization. Preferably, the ligand is a polyclonal or monoclonal antibody which can be used to target liposomes to specific cell-surface ligands. The ligand can also be an antibody fragment, such as Fab, or $F(ab')_2$, as long as it binds efficiently to an the antigenic epitope on the target cells. Preferably, the antibody or antibody fragment recognizes an antigen that is found exclusively on the target cell. For example, certain antigens expressed specifically on macrophage cells, such as scavenger receptor A, may be exploited for the purpose of targeting antibody-ABC1 liposomes directly to a macrophage cell.

A number of procedures can be used to covalently attach either polyclonal or monoclonal antibodies to a liposome bilayer. Also, lipid groups can be incorporated into the lipid bilayer of the liposome in order to maintain the targeting ligand in stable association with the liposomal bilayer. In addition, various linking groups can be used for joining the lipid chains to the targeting ligand.

Studies presented herein showed that ligands for nuclear receptors were able to effect an increase in cholesterol efflux. Accordingly, in another embodiment, the present invention provides a method suitable for increasing cholesterol efflux from cells in a mammalian subject comprising the step of administering to the mammalian subject at least one ligand for a nuclear receptor in an amount sufficient to increase cholesterol efflux from said cells. A pharmaceutical composition comprising a ligand for a nuclear receptor can prepared and administered using the above-described methods for formulating and administering pharmaceutical compositions. A sufficient amount of a nuclear receptor ligand is the amount of ligand that increases cholesterol efflux. Such amount can be determined by measuring the cholesterol efflux before and after administration of the ligand at various dosages and determining the dose that effects an increase in cholesterol efflux. The cholesterol efflux can be measured using assays previously described.

Nuclear receptors are ligand-activated transcription factors that play a critical role in vertebrate development and adult physiology by transducing the effects of small, lipophilic hormones into transcriptional responses. Several families of nuclear receptors exist, including peroxisome proliferator-activated receptors (PPARs), liver X receptors (LXR), retinoid X receptor (RXR), the farnesoid X receptor (FXR), and the steroid and xenobiotic receptor (SXR). The PPAR family comprises the three closely related gene products PPARα, PPARγ, and PPARβ/δ. PPARα has been implicated as a key regulator of intra- and extracellular lipid metabolism. When bound to fatty acids, PPARα stimulates the proliferation of peroxisomes and induces the synthesis of several enzymes involved in the β-oxidation of fatty acids. The PPARα receptor is also the molecular target for the fibrates, drugs that are prescribed for the reduction of high triglyceride levels (Isseman et al., *Nature,* 347, 645 (1990)). Fibrates act as PPAR ligands to regulate the transcription of a large number of genes that affect lipoprotein and fatty acid metabolism. In addition, PPARγ ligands, such as compounds belonging to the class of thiazolidinediones compounds, have been shown to increase HDL and reduce triglyceride levels in humans.

LXR is an oxysterol receptor that regulates the catabolism of excess cholesterol. LXRα has been shown to bind as a heterodimer with RXR to a DNA response element in the CYP7a gene, which encodes the enzyme responsible for the rate-limiting step in the conversion of cholesterol to bile acids. Studies have shown that mice lacking LXRα accumulate enormous amounts of cholesterol esters in their livers when fed a cholesterol-rich diet, due to their inability to increase CYP7a gene transcription in response to dietary cholesterol (Peet et al., *Cell,* 93: 693 (1998)). Further studies with LXRα null mice show that LXRα is also involved in the regulation of several other genes that particpate in cholesterol and fatty acid homeostasis. The biological role of a closely related nuclear receptor, LXRβ, which is expressed in several tissues and is activated by the same oxysterols as LXRα, remains unclear (Song et al., *Proc. Natl. Acad. Sci.,* 91: 10809 (1994); Seol, *Mol. Endocrinol.,* 9: 72 (1995)).

FXR, which is evolutionarily related to LXRα, is also involved in cholesterol homeostasis. Like LXRα, FXR functions as a heterodimer with the RXR receptor (Schwartz et al., *Curr. Opin. Lipidol.,* 9: 113 (1998); Vlahcevic et al., *Gastroenterology,* 113: 1949 (1997)). FXR is activated by the synthetic retinoid TTNPB and superphysiological concentrations of all-trans retinoic acid (Zavacki et al., *Proc. Natl. Acad. Sci.,* 94: 7909 (1997)). Recent studies indicate that FXR is a nuclear bile acid receptor. First, FXR is abundantly expressed in tissues through which bile acids circulate, including the liver, intestine, and kidney (Seol et al., *Mol. Endocrinol.,* 9: 72 (1995); Forman et al., *Cell,* 81: 687 (1995)). Also, FXR has recently been shown to serve as a receptor for physiological concentrations of several bile salts, among which chenodeoxycholic acid (CDCA) is the most potent (Kliewer et al., *Science,* 284: 757-284 (1999); Makishima et al., *Science,* 284: 1362-1363 (1999)). CDCA is known to regulate the expression of several genes that participate in bile salt homeostasis, including those encoding CYP7a and the intestinal bile acid-binding protein.

As described in detail in Example 13, ligands for LXR, RXR, and PPAR nuclear receptors were shown to increase apoAI-induced cholesterol efflux in cholesterol-loaded mouse macrophage cells. For example, administration of 9 cis-retinoic acid (30 ng/ml) produced approximately a 3-fold increase in apoAI-induced cholesterol efflux in these cells. Similarly, administration of 22(R)-hydroxycholesterol (5 μg/ml) produced approximately a 3-fold increase in apoAI-induced cholesterol efflux. Cells that received fenfibrate (3 μg/ml) produced an approximate 2-fold increase in cholesterol efflux. These results indicate that nuclear receptors may be modulated to increase the rate of apolipoprotein-mediated cholesterol efflux from macrophages. Furthermore, as described in Example 13, 9-cis-RA mediated cholesterol efflux from macrophage cells in a dose-dependent manner. Other nuclear receptor activators, such as bezafibrate, were shown to increase cholesterol efflux (data not shown).

Accordingly, in the method for increasing cholesterol efflux by administering a nuclear receptor ligand, the ligand is preferably selected from the group consisting of LXR, RXR, PPAR, FXR, and SXR nuclear receptor ligands. In the preferred embodiment wherein a LXR ligand is used to increase cholesterol efflux, the ligand is more preferably selected from the group consisting of 20(S) hydroxycholesterol, 22(R) hydroxycholesterol, 24-hydroxycholesterol, 25-hydroxycholesterol, and 24(S), 25 epoxycholesterol LXR ligands. Most preferably, the LXR ligand is 20(S) hydroxycholesterol. In the preferred embodiment wherein a RXR ligand is used to increase cholesterol efflux, the ligand is more preferably selected from the group consisting of 9-cis retinoic acid, retinol, retinal, all-trans retinoic acid, 13-cis retinoic acid, acitretin, fenretinide, etretinate, CD 495, CD564, TTNN, TTNNPB, TTAB, LGD 1069. Most preferably, the RXR ligand is 9-cis retinoic acid. In another preferred embodiment wherein a PPAR ligand is used to increase cholesterol efflux, the ligand is preferably selected from the class of thiazolidinedione compounds.

In another preferred embodiment, more than one nuclear receptor ligand is administered to the mammalian subject to increase cholesterol efflux. Preferably, when two or more nuclear receptor ligands are administered to a subject, the ligands are an LXR and an RXR ligand. More preferably, the nuclear receptor ligands are 20(S) hydroxycholesterol and 9-cis retinoic acid.

In still another embodiment, the present invention provides a method suitable for increasing cholesterol efflux from cells in a mammalian subject comprising the step of administering to the mammalian subject an eicosanoid in an amount sufficient to increase cholesterol efflux. A pharmaceutical composition comprising an eicosanoid can be prepared and administered using the above-described methods for formulating and administering pharmaceutical compositions. A sufficient amount of eicosanoid is the amount that increases cholesterol efflux. Such amount can be determined by measuring the cholesterol efflux before and after administration of the eicosanoid at various dosages and determining the dose that effects an increase in cholesterol efflux. The cholesterol efflux can be measured using assays and methods previously described.

As described in Example 14, eicosanoids were shown to increase apoAI-induced cholesterol efflux in cholesterol-loaded mouse macrophage cells. For example, administration of PGI2 (25 nm) produced approximately a 2-fold increase in apoAI-induced cholesterol efflux in these cells. Likewise, administration of PGE1 (25 nM) produced approximately a 3-fold increase in apoAI-induced cholesterol efflux. These results demonstrate that eicoasnoids can increase the rate of apolipoprotein-mediated cholesterol efflux from macrophages. Accordingly, in a preferred embodiment, the eicosanoid is selected from the group consisting of prostaglandin E2, prostacyclin (prostaglandin I2), and prostaglandin J2 eicosanoids.

Methods and Compounds for Increasing ABC1 Expression/Activity

Given that ABC1 functions to promote cholesterol efflux, one way to increase cholesterol efflux is to increase the cellular expression of ABC1. Accordingly, the present invention also provides methods suitable for increasing cholesterol efflux from cells in a mammalian subject by administering to the mammalian subject a therapeutic amount of a compound that increases the expression of ABC1 in said cells. A therapeutic amount of compound is the amount of compound that increases ABC1 expression. Such amount can be determined by measuring the gene expression of ABC1 before and after administration of the compound at various dosages and determining the dose that effects an increase in ABC1 gene expression. The ABC1 gene expression can be measured by obtaining a blood sample from the subject, separating the monocyte population, and determining the concentration of ABC1 mRNA using methods known in the art and described herein, such as RT-PCR.

Figure 8:
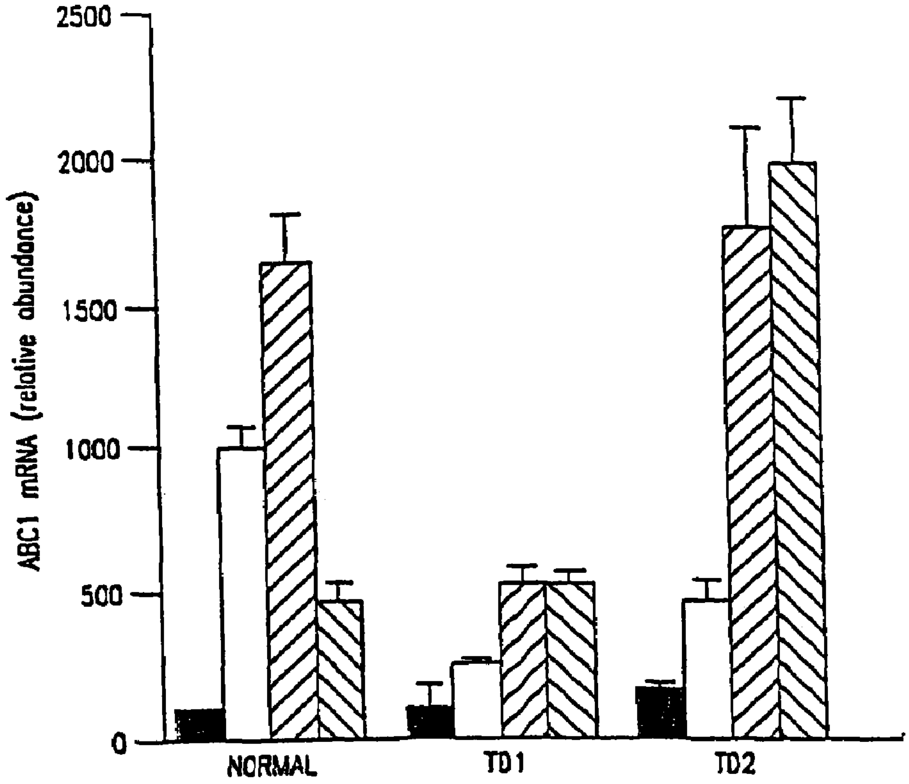
FIG. 8 is a graphical representation of reverse transcription polymerase chain reaction (RT-PCR) analyses showing the level of ABC1 gene expression in normal cells and cells from Tangier's disease patients (TD1 and TD2) that have been either exposed to albumin (closed bars), exposed to 8-Br-cAMP (open bars), cholesterol-loaded (shaded bars), or cholesterol-loaded and subsequently exposed to apo A-I (hatched bars)

In one preferred embodiment, the method comprises administering a cAMP analogue to increase the gene expression of ABC1. As shown in FIG. 8, cAMP increases the expression of ABC1 mRNA in normal fibroblast cells approximately 10-fold. Preferably, the cAMP analogue is selected from the group consisting of 8-bromo cAMP, N6-benzoyl cAMP, and 8-thiomethyl cAMP. In another preferred embodiment, the method comprises administering a compound that increases the synthesis of cAMP to increase the gene expression of ABC1. Preferably, the compound is forskolin. In yet another preferred embodiment, the method comprises administering a compound that inhibits the breakdown of cAMP to increase the gene expression of ABC1. An example of such a compound is a phosphodiesterase inhibitor. Preferably, the phosphodiesterase inhibitor is selected from the group consisting of rolipram, theophylline, 3-isobutyl-1-methylxanthine, R020-1724, vinpocetine, zaprinast, dipyridamole, milrinone, amrinone, pimobendan, cilostamide, enoximone, peroximone, and vesnarinone phosphodiesterase inhibitors.

In another preferred embodiment, the method comprises administering to the mammalian subject a ligand for a nuclear receptor in an amount sufficient to increase the gene expression of ABC1. As described in Example 17 and shown in FIG. 12, ligands for nuclear receptors can up-regulate the gene expression of ABC1. Transfection studies using pAPR1, which contains a luciferase reporter gene under the control of the ABC1 promoter, showed that the ABC1 promoter was activated in the presence of ligands for LXR and RXR nuclear receptors. Specifically, macrophage cells transfected with pAPR1 produced a 19-fold increase in luciferase reporter activity in the presence of 20 OH-chol, a 16-fold increase in luciferase activity in the presence of 9-cis RA, and a 280-fold increase in luciferase activity in the presence of both ligands compared with EtOH control. The results indicate that both sterols and retinoids elicit a strong transcription response from the ABC1 promoter. Further, there is an apparent synergistic effect between the two classes of compounds, as can be seen by the dramatic increase in luciferase activity found in cells treated with both ligands. In accordance with the inventive method, preferably, the ligand is selected from the group consisting of LXR, RXR, PPAR, FXR, and SXR ligands.

In addition to increasing cellular levels of ABC1 protein, reverse cholesterol transport can be promoted by enhancing the activity of ABC1 protein. Thus, in another embodiment, the present invention provides a method suitable for increasing cholesterol efflux from cells in a mammalian subject comprising the step of administering to the mammalian subject a therapeutic amount of a compound that increases ABC1 activity in an amount sufficient to increase cholesterol efflux. A pharmaceutical composition comprising such a compound can prepared and administered using the above-described methods for formulating and administering pharmaceutical compositions. A therapeutic amount of compound is the amount of compound that increases cholesterol efflux. Such amount can be determined by measuring the cholesterol efflux before and after administration of the compound at various dosages and determining the dose that effects an increase in cholesterol efflux using methods previously described. To determine whether an increase in cholesterol efflux is due to an increase in ABC1 activity, the amount of ABC1 protein present in a cell sample before and after administration of the compound is determined, using methods described herein (see Example 11). For both measurements (i.e. pre- and post-administration of the compound), the amount of cholesterol efflux activity is divided by the concentration of ABC1 protein to determine the amount of cholesterol activity found in a standard concentration of ABC1 protein. An observed increase in cholesterol activity standardized to protein concentration indicates that the increase is due to an increase in ABC1 activity.

Methods for Identifying Therapeutic Compounds

Another aspect of the present invention relates to methods for screening a compound to determine whether the compound modulates (i.e., up-regulates or down-regulates) the gene expression of ABC1. Such compounds may be useful in the development of therapeutic compounds that increase ABC1 expression and thereby promote cholesterol efflux and raise blood levels of HDL-cholesterol. Accordingly, methods for identifying compounds that may be useful in the treatment of cardiovascular disease are provided. In one embodiment, the present invention provides a method for screening a test compound for ABC1 expression modulating activity comprising the steps of: (a) operatively linking a reporter cDNA with an expression modulating portion of the mammalian ABC1 gene to produce a recombinant reporter construct; (b) transfecting the recombinant reporter construct into a population of host cells; (c) assaying the level of reporter gene expression in a sample of the transfected host cells; (d) contacting the transfected host cells with the test compound being screened; (e) assaying the level of reporter gene expression in a sample of the transfected host cells after contact with the test compound; and (f) comparing the relative change in the level of reporter gene expression caused by exposure to the test compound, thereby determining the ABC1 expression modulating activity.

First, a recombinant reporter construct comprising a heterologous reporter gene operatively linked to an expression modulating portion of the ABC1 gene is constructed. The ABC1 expression modulating polynucleotide and reporter gene can be inserted into a vector using well-known ligation and cloning techniques, such as those described herein and in standard laboratory manuals, including Davis et al., *Basic Methods in Molecular Biology* (1986); Sambrook et al., *Molecular Cloning: A Laboratory Manual,* 2$^{nd}$ Ed., (Cold Spring Harbor Press, Cold Spring Harbor, N.Y. (1989)); and Ausubel et al. eds., *Current Protocols in Molecular Biology*, (Wiley and Sons (1994)). Alternatively, the ABC1 expression modulating polynucleotide can be inserted into a commercially available reporter construct, such as those previously described. Any vector suitable for ABC1 polynucleotide and reporter gene insertion can be used. The chosen vector should be functional in the particular host cell employed. Preferably, the vector is compatible with mammalian host cells.

Preferably, the expression modulating portion of the ABC1 gene is the 5' flanking region of ABC1, containing ABC1 promoter activity. In one preferred embodiment, the expression modulating portion of the ABC1 gene comprises SEQ ID NO: 3. In another preferred embodiment, the expression modulating portion of the ABC1 gene comprises nucleotides 1-1532, 1080-1643, 1181-1643, 1292-1643, 1394-1643, or 1394-1532 of SEQ ID NO: 3. Also, preferably the heterologous reporter is selected from the group consisting of polynucleotides that encode the luciferase, β-galactosidase, chloramphenicol acetyl transferase, and green fluorescent proteins. More preferably, the heterologous reporter is a polynucleotide that encodes the luciferase protein. In a particularly preferred embodiment, the recombinant reporter construct is pAPR1, shown in FIG. 11.

Next, the recombinant reporter construct is transfected into a population of host cells. The recombinant reporter construct can be introduced into the host cells using any of the previously described transfection methods, as well as the methods described in Examples 8 and 15. For example, the reporter construct can be transfected using calcium phosphate transfection, DEAE-dextran mediated transfection, cationic lipid-mediated transfection, electroporation, transduction, infection, or any of the other known and described methods (see, e.g., Davis et al., *Basic Methods in Molecular Biology* (1986)). The host cell can be any cell that, when cultured under appropriate conditions, synthesizes a reporter polypeptide, which can be subsequently measured. Preferably, the host cell is a mammalian host cell. More preferably, the mammalian host cell is a macrophage, fibroblast, hepatic, or intestinal cell. Most preferably, the host cell is selected from the group consisting of RAW 264.7 cells, Thp-1 cells, and HepG2 cells. The concentration of reporter construct and duration of the transfection can vary, depending on the transfection method and the type and concentration of host cell used. Determination of the appropriate concentration of reporter construct and transfection time is well within the skill of the ordinary artisan.

Following transfection, a sample of transfected host cells that was not exposed to the test compound is assayed to determine the level of reporter gene expression. The level of reporter gene expression found in the sample of unexposed transfected host cells provides a control measurement. The transfected host cells are lysed and the level of reporter gene expression is assayed using any of the methods well-known in the art. The assays used to measure the level of reporter gene expression differ, depending on the reporter construct used in the transfections. For example, if a luciferase reporter construct is used, the luciferase activity of the cell lysate is measured as light units using a luminometer, as described in Example 15.

A different sample of the transfected host cells is contacted with the test compound being screened and the level of reporter gene expression found in these cells is subsequently measured. Preferably, the transfected host cells are contacted with the test compound for about 4-48 hours. More preferably, the transfected host cells are contacted with the test compound for about 8-36 hours. Even more preferably, the transfected host cells are contacted with the test compound for about 24 hours. The same assay used to measure the level of reporter gene expression in unexposed (control) cells should be used to measure the level of reporter gene expression in the cells exposed to the test compound.

Finally, the level of reporter gene expression found in unexposed control cells is compared with the level of reporter gene expression found in cells exposed to the test compound to determine whether the test compound has ABC1 expression modulating activity. If the level of gene expression in both cell samples are the same or about the same, the test compound does not modulate ABC1 gene expression. A higher level of reporter gene expression in cells exposed to the test compound relative to the level of reporter gene expression found in control cells, indicates that the test compound up-regulates the gene expression of ABC1. A lower level of reporter gene expression in cells exposed to the test compound relative to the level of reporter gene expression found in control cells, indicates that the test compound down-regulates the gene expression of ABC1.

Another aspect of the present invention relates to methods for screening a test compound to determine whether the compound promotes ABC1-mediated cholesterol efflux. Such method comprises: (a) assaying the level of cholesterol efflux in a sample of mammalian cells maintained in culture to determine a control level of cholesterol efflux, (b) contacting the mammalian cells with the test compound being screened; (c) assaying the level of cholesterol efflux in a sample of cells after contact with the test compound; and (d) assaying the level of ABC1-dependent cholesterol efflux in a sample of cells after contact with the test compound, thereby determining whether the test compound promotes ABC1-mediated cholesterol efflux from cells in culture.

The level of cholesterol efflux in a sample of cultured cells can be determined using methods known in the art and described herein (see Example 1). Any mammalian cells that can be maintained in culture can be used to measure cholesterol efflux. The cells can be derived from primary cultures or from immortalized cell lines. For convenience, cells can be immortalized by transfecting them with amphotropic retroviruses containing vectors with inserts of human papillomavirus 16, oncogenes E6 and E7, and a selectable marker gene, as described in Example 1. Preferably, the cultured cells are fibroblast, macrophage, hepatic, or intestinal cells. More preferably, the cultured cells are RAW 264.7 cells.

The level of cholesterol efflux in a sample of cells that has not been contacted with the test compound is measured to obtain a control level of cholesterol efflux. In addition, the level of cholesterol efflux in a sample of mammalian cells that has been contacted with the test compound is measured to determine the amount of cholesterol efflux affected by the test compound. Also, the level of ABC1-mediated cholesterol efflux in a sample of mammalian cells that has been contacted with the test compound is measured to determine the amount of ABC1-mediated cholesterol efflux affected by the test compound. Preferably, the cells are contacted with the test compound for about 8-24 hours before cholesterol efflux or ABC1-mediated cholesterol efflux is assayed. The level of ABC1-mediated cholesterol efflux can be assayed using an anti-ABC1 antibody that, upon binding, inhibits the activity of ABC1. Alternatively, the level of ABC1-mediated cholesterol efflux can be assayed using an anti-sense ABC1 polynucleotide that inhibits the expression of ABC1. For example, the level of ABC1-mediated cholesterol efflux can be assayed using the anti-sense ABC1 polynucleotide comprising SEQ ID NO: 57 (see Example 7). The cells should be contacted with the anti-ABC1 antibody or anti-sense ABC1 polynucleotide at the same time and for the same duration that it is contacted with the test compound.

If the level of control cholesterol efflux is the same or about the same as the level of cholesterol efflux found in cells contacted with the test compound, the compound does not promote cholesterol efflux. An increase in the level of cholesterol efflux found in cells contacted with test compound over the control level of cholesterol efflux indicates the amount of cholesterol efflux promoted by the test compound. The difference between the cholesterol efflux found in cells contacted with test compound alone and the cholesterol efflux found in cells contacted with test compound and anti-ABC1 antibody or anti-sense ABC1 polynucleotide indicates the amount of cholesterol efflux mediated through ABC1. For example, if control level of cholesterol efflux is 1.0 and the level of cholesterol efflux found in cells contacted with test compound is 1.1, the test compound promotes cholesterol efflux by 10%. If the cholesterol efflux found in cells contacted with test compound and anti-ABC1 antibody or anti-sense ABC1 polynucleotide is 1.0, the increase in cholesterol efflux caused by the test compound is entirely ABC1-mediated.

Methods for Detecting Susceptibility to Coronary Heart Disease

The present invention also relates to methods for detecting the comparative level of ABC1 gene or protein expression in a mammalian subject, including a human subject. Given the role of ABC1 in cholesterol efflux, the determination of a decreased level of ABC1 gene or protein expression in a mammalian subject relative to a pre-determined standard level of ABC1 gene or protein expression can be used to indicate a susceptibility to coronary heart disease in the subject. Accordingly, the present invention provides a method for detecting the comparative level of ABC1 gene expression in a mammalian subject comprising the steps of:

(a) obtaining a test cell sample from the mammalian subject; (b) assaying the level of ABC1 mRNA expression in the test cell sample; and (c) comparing the level of ABC1 mRNA expression in the test cell sample with a pre-determined standard level of ABC1 mRNA expression, thereby detecting the comparative level of ABC1 gene expression in the mammalian subject.

A test cell sample is first obtained from a mammalian subject, including a human subject. The test cell sample can be a blood sample, wherein the monocyte population has been enriched. Monocytes can be enriched using well-known cell separation procedures based on, for example, cell size, cell density or cell affinity. Next, the level of ABC1 mRNA expression in the test cell sample is assayed. The level of ABC1 mRNA expression can be assayed using any of the well-known methods for mRNA preparation and detection, including the methods described herein at Examples 2 and 9. For example, the concentration of ABC1 mRNA can be determined by reverse transcription polymerase chain reaction, northern blot analysis, or RNAse protection assay. The ABC1 mRNA concentration should be standardized to the concentration of total mRNA found in the test cell sample. Finally, the ABC1 expression in the test cell sample is compared with a pre-determined standard level of ABC1 mRNA expression. A pre-determined standard level of ABC1 mRNA expression can be obtained by determining the average concentrations and distribution of ABC1 mRNA found in cell samples taken from a representative population of mammalian subjects, wherein the mammalian subjects are the same species as the subject from which the test cell sample was obtained, and wherein the mammalian subjects do not have coronary heart disease, Tangier disease, or other disease associated with low HDL-cholesterol and are considered to have cholesterol efflux activity within a normal range (i.e., as indicated by an HDL-cholesterol level within a normal range). The determination of a decreased level of ABC1 mRNA expression in the test cell sample of a mammalian subject relative to the pre-determined standard level of ABC1 mRNA expression can be used to indicate a susceptibility to coronary heart disease in the mammalian subject.

Likewise, the detection of a decreased level of ABC1 protein can be used to indicate decreased capacity for cholesterol efflux and a susceptibility to coronary heart disease. Accordingly, another embodiment of the present invention provides a method for detecting the comparative level of ABC1 protein in a mammalian subject. Such method comprises the steps of: (a) obtaining a test cell sample from the mammalian subject; (b) assaying the amount of ABC1 protein in the test cell sample; and (c) comparing the amount of ABC1 protein in the test cell sample with a pre-determined standard amount of ABC1 protein, thereby detecting the comparative level of ABC1 protein in the mammalian subject.

The amount of ABC1 protein can be assayed using any of the well-known methods of measuring protein. Preferably, the amount of ABC1 protein is measured using an immunoassay. In one embodiment, the amount of ABC1 protein is determined by (a) contacting the cell sample with a population of anti-ABC1 antibodies and (b) detecting the anti-ABC1 antibodies associated with the cell sample. For example, the ABC1 protein can be contacted with an antiserum raised against a synthetic peptide corresponding to KNQTVVDAVLTSFLQDEKVKES (SEQ ID NO: 60) located at the C-terminus, as described in Example 11. The anti-ABC1 antibodies can be detected using several methods known in the art, including, for example, western blotting, immunoprecipitation, and FACS, wherein the detection can be accomplished using radioactive, colorometric, or fluorescent labeling. One preferred method for measuring the amount of ABC1 protein in a cell sample is immunoprecipitation, wherein biotinylated ABC1 proteins are contacted with anti-ABC1 antibody and the bound anti-ABC1 antibody is detected using streptavidin horse radish peroxidase.

The amount ABC1 protein in the test cell sample is compared with a pre-determined standard amount of ABC1 protein. A pre-determined standard amount of ABC1 protein can be obtained by determining the average concentration of ABC1 protein found in cell samples taken from a population of mammalian subjects, wherein the mammalian subjects are the same species as the subject from which the test cell sample was obtained, and wherein the mammalian subjects do not have coronary heart disease, Tangier disease, or other disease associated with low HDL-cholesterol and are considered to have cholesterol efflux activity within a normal range (i.e., as indicated by an HDL-cholesterol level within a normal range).

ABC1 Antibodies

As used herein, the term “antibody” (Ab) or “monoclonal antibody” (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody (Wahl et al., *J. Nucl. Med.,* 24:316-325 (1983)). Thus, these fragments are preferred, as well as the products of a FAB or other immunoglobulin expression library. Moreover, antibodies of the present invention include chimeric, single chain, and humanized antibodies.

Additional embodiments include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

One method for producing an antibody comprises immunizing a non-human animal, such as a transgenic mouse, with a polypeptide translated from a polynucleotide comprising SEQ ID NO: 1, a polynucleotide comprising nucleotides 291-7074 of SEQ ID NO: 1, or a polynucleotide comprising a nucleotide sequence that has at least 90% identity with a polynucleotide comprising SEQ ID NO: 1, whereby antibodies directed against the polypeptide translated from the described polynucleotides are generated in said animal. Procedures have been developed for generating human antibodies in non-human animals. The antibodies may be partially human, or preferably completely human. Non-human animals (such as transgenic mice) into which genetic material encoding one or more human immunoglobulin chains has been introduced may be employed. Such transgenic mice may be genetically altered in a variety of ways. The genetic manipulation may result in human immunoglobulin polypeptide chains replacing endogenous immunoglobulin chains in at least some (preferably virtually all) antibodies produced by the animal upon immunization. Antibodies produced by immunizing transgenic animals with a polypeptide translated from any of the described polynucleotides are provided herein.

Mice in which one or more endogenous immunoglobulin genes are inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

Monoclonal antibodies may be produced by conventional procedures, e.g., by immortalizing spleen cells harvested from the transgenic animal after completion of the immunization schedule. The spleen cells may be fused with myeloma cells to produce hybridomas, by conventional procedures.

A method for producing a hybridoma cell line comprises immunizing such a transgenic animal with a immunogen comprising at least seven contiguous amino acid residues of a polypeptide translated from one of the described polynucleotides; harvesting spleen cells from the immunized animal; fusing the harvested spleen cells to a myeloma cell line, thereby generating hybridoma cells; and identifying a hybridoma cell line that produces a monoclonal antibody that binds a polypeptide translated from one of the described polynucleotides. Such hybridoma cell lines, and monoclonal antibodies produced therefrom, are encompassed by the present invention. Monoclonal antibodies secreted by the hybridoma cell line are purified by conventional techniques.

The antibodies, upon specific binding to an ABC1 polypeptide, may inhibit the activity of the ABC1 polypeptide. Preferably, the antibody, upon binding, inhibits the cholesterol transport activity of the ABC1 polypeptide. Such antibodies can be made by immunizing a non-human animal with a polypeptide corresponding to the region essential for cholesterol transport. The antibody can be tested to determine whether it inhibits cholesterol efflux using any of the described cholesterol efflux assays. Such inactivating antibodies can be employed in an in vitro assay, such as any of the cholesterol efflux assays described herein, to determine whether a test compound promotes ABC1-mediated cholesterol efflux. The inactivating antibodies can also be used in in vitro assays to detect the comparative level of ABC1 protein in the cells of a mammalian subject. The inactivating antibodies are also useful in kits suitable for screening a compound to determine whether the compound modulates ABC1-dependent cholesterol efflux.

Kits for Identifying Therapeutic Compounds

The present invention also includes a kit suitable for screening a compound to determine the ABC1 expression modulating activity of a compound. The kit includes, in an amount sufficient to perform at least one assay, a recombinant reporter construct comprising a reporter cDNA operatively linked to an expression modulating portion of the mammalian ABC1 gene, as a separately packaged reagent. Instructions for use of the packaged reagent(s) are also typically included. The expression modulating portion of the mammalian ABC1 gene comprises the 5' flanking sequence. In one preferred embodiment, the expression modulating portion of the mammalian ABC1 gene comprises SEQ ID NO: 3. In other preferred embodiments, the expression modulating portion of the mammalian ABC1 gene comprises nucleotides 1-1532, 1080-1643, 1181-1643, 1292-1643, 1394-1643, or 1394-1532 of SEQ ID NO: 3. The reporter cDNA can be any suitable reporter gene, including In a particularly preferred embodiment, the recombinant reporter construct is pAPR1. In another embodiment, the kit further comprises means for detecting the reporter protein. Thus, the kit comprises reagents, such as buffers and substrates, used for reporter protein detection.

As used herein, the term "package" refers to a solid matrix or material such as glass, plastic (e.g., polyethylene, polypropylene or polycarbonate), paper, foil and the like capable of holding within fixed limits a recombinant vector of the present invention. Thus, for example, a package can be a glass vial used to contain milligram quantities of a contemplated vector.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In addition, the present invention also includes a kit suitable for screening a compound to determine whether the compound modulates ABC1-dependent cholesterol efflux. In one embodiment, the kit includes, in an amount sufficient to perform at least one assay, an inactivating anti-ABC1 antibody, as a separately packaged reagent. Instructions for use of the packaged reagent(s) are also typically included.

In another embodiment, the kit includes an antisense ABC1 oligonucleotide in an amount sufficient for at least one assay and instructions for use. Preferably, the antisense ABC1 oligonucleotide comprises SEQ ID NO: 53.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the ABC1 molecules of the invention, including, but not limited to: the identification and validation of ABC1 disease-related genes as targets for therapeutics; molecular toxicology of related ABC1 molecules and inhibitors thereof; stratification of populations and generation of surrogate markers for clinical trials; and enhancing related ABC1 polypeptide small molecule drug discovery by aiding in the identification of selective compounds in high throughput screens.

As discussed herein at Example 2, a method has been developed that uses samples of RNA derived from cells of an individual with a genetic abnormality and compares them to the RNA from a normal individual. Historically, identification of the cause of inherited diseases resulted from years of biochemical analysis or, more recently, from years of gene mapping and positional cloning to identify the suspect gene within an interval of millions of base pairs which had been shown to be closely linked to the defect in inheritance studies (linkage analysis). The use of multigene expression analysis, most notably via "gene chips" can revolutionize the pace of such discovery. Comparing the expression of samples of RNA derived from cells from an abnormal individual with a genetic disease versus RNA from an normal individual can quickly reveal genes whose corresponding mRNA is missing, severely underrepresented or severely overrepresented in the abnormal diseased cell.

The term "individual" and used herein refers to any living organism that has RNA such as, for example, mammals, plants. This method is preferably used to identify the source of human genetic abnormalities. More preferably, the method is useful for detecting genetic sources of human cardiac and cardiovascular disorders such as identifying ABC1 as the genetic defect in Tangier's disease.

The term "abnormality" as it is used herein refers to genetic differences that cause a physiological deviation in small number of individuals in a species in comparison to the majority of individuals of the species. The abnormality may be a positive abnormality or a negative abnormality. For example, a positive plant abnormality would be a genetic difference that causes some individual plants to be drought resistant in comparison to the other individuals in the species. A negative abnormality would be one that causes an individual in the same species of plant to me more prone to drought damage than a normal plant.

The method can best be described by reference to our investigation into the genetic cause of Tangier's disease. We began our investigation by using RNA from cells cultured from an individual with Tangier disease to probe microarrays containing nearly 60,000 normal human genes, and we were able to use the probe results to identify ABC1 as the defective gene in this monogenic disease in which patients have near zero levels of circulating high density lipoprotein (HDL) and an increased risk of heart disease. It is not necessary that the defective gene results in a zero level of detectable mRNA signal in such an experiment. In this successful example, roughly 175 out of the 58,800 probes on the micro-array were more than 2.5 fold underexpressed in the Tangier disease RNA versus normal. Several additional steps may be taken to confirm the identity of the culprit gene. They include repeating such a micro-array probe with an unrelated individual with Tangier disease, determining the chromosome map location of each gene to compare with a reported large genetic interval that was linked to the disease, consideration of the likely function of the candidate proteins and their homologs, biochemical tests, and sequencing the best candidate gene in patients to find mutations. In these ways, gene expression micro-array analysis can lead to the identification of inherited genetic defects such as the identification of ABC1 as the defect in Tangier disease A further utility in this method is that other genes that are either under- or over-expressed in the disease sample vs. normal should include those that are differentially regulated in consequence of the genetic defect in the patient, either as compensatory responses or as contributors to the disease pathology. This could provide identification of other proteins in the relevant biological pathways that may be amenable to drug development and help elucidate the pathology of the disease, with implications for treatment and diagnosis. In the cases where a gene deletion or other mutation causes complete absence of mRNA, as observed in many examples of thalassemia (globin gene defects) and other genetic diseases, gene expression analysis of disease versus normal samples can lead to the identification of the missing gene in a more straightforward manner.

Although in these examples, the gene expression array that was probed with RNA samples was of the type in which probe samples were cDNAs arrayed on microscope slides, alternative array technologies would suffice. These would include, but not limited to those which array DNA samples on filter membranes or use oligonucleotide probes synthesized on "gene chips" by photolithography.

Generally, the term microarray refers to an array of distinct oligonucleotides synthesized on a substrate, such as paper, nylon or other type of membrane, filter, chip, glass slide, or any other suitable solid support. Microarrays may be prepared, used, and analyzed using methods known in the art. (See, e.g., Brennan, T. M. et al. (1995) U.S. Pat. No. 5,474,796; PCT application WO95/251116; Shalon, D. et al. (1995) PCT application WO95/35505; and U.S. Pat. No. 5,605,662 the specifications of each of which are incorporated herein by reference)

A chemical coupling procedure and an ink jet device can be used to synthesize array elements on the surface of the substrate. An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complimentrity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to the nucleotide sequences of an abnormal individual and a normal individual are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467-470; Shalon, D. et al. (1996) Genome Res. 6:639-645.) Probes, such as fluorescent probes are prepared and used for hybridization to the elements on the substrate.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

Once the genetic causes of the inherited abnormality are narrowed or identified, the potentially or actual defective portions of the genes can be used as targets in a microarray. The microarray can be used to monitor the expression level of a large number of genes to develop and monitor the activities of potential therapies and therapeutic agents.

The following examples further illustrate the present invention but should not be construed to limit the present invention in any way.

EXAMPLE 1

This example demonstrates that patients with Tangier Disease (TD) have an absence of apo A-I-mediated lipid efflux.

Cell Cultures: Human fibroblasts were obtained from skin explants from two normal subjects (NL1) and three unrelated patients with Tangier disease (TD). TD1 cells were obtained from a 53 year-old female with extremely low plasma HDL cholesterol and apo A-I levels and clinical symptoms typical of Tangier disease. TD2 cells were obtained from a 56 year-old male with clinical, morphological, and biochemical features of Tangier disease, including very low levels of plasma HDL cholesterol and apoA-I (Francis, et al., *J. Clin. Invest.,* 96, 78-87 (1995)). TD3 cells were obtained from an 18 year-old male with Tangier disease who presented with orange tonsil remnants, asymmetrical motor neuropathy, plasma HDL cholesterol of 5 mg/dL, and LDL cholesterol of 16 mg/dL (Lawn et al., *J. Clin. Invest.,* 104, R25-R31 (1999)). The normal cells and TD subject cells were immortalized as described in Oram et al., *J. Lipid Res.,* 40: 1769-1781 (1999). Briefly, the cells were transfected with amphotropic retroviruses containing vectors with inserts of human papillomavirus 16 oncogenes E6 and E7 and a neomycin resistance selectable marker. Control cells were infected with vector alone (mock-infected). Pooled cell populations were selected in the presence of G418 for two passages, after which G418 was excluded from the medium. Fibroblasts were used between the fifth and sixteenth passage (primary) or sixth and fourteenth passage (immortalized). The immortalized normal and TD cells were seeded into 16-mm wells or 35-mm dishes and grown to confluence in Dulbecco's modified Eagle's medium (DMEM) plus 10% fetal bovine serum (FBS) before experimental use. RAW 264.7 mouse monocytic cells (American Type Culture Collection, Rockville, Md.) were also maintained in DMEM containing 10% FBS.

Assay to Measure Lipid Efflux: Apo AI-mediated efflux of cholesterol and phospholipid was assayed according to the method described in Francis, et al., *J. Clin. Invest.,* 96: 78-87 (1995). The cultured skin fibroblasts from normal and TD subjects were labeled by growth to confluence in the presence of 0.2-0.5 μCi/ml [$^3$H]cholesterol (40-60 Ci/mmol, Amersham Corp., Arlington Heights, Ill.). The radioactive cholesterol was added to serum-containing growth medium when the cells were 60-80% confluent. After 3 days, the cells were washed twice with PBS/BSA and simultaneously growth-arrested and cholesterol-loaded to maximize apolipoprotein-mediated lipid efflux. This was achieved by incubating the cells for 48 hours in serum-free DMEM plus 2 mg/ml fatty acid-free bovine serum albumin (DMEM/BSA) (Sigma Chemical Co., St. Louis, Mo.) and 30 μg/ml nonradioactive cholesterol. RAW 264.7 cells were cholesterol-loaded through the scavenger receptor by 24-hour incubation with acetylated LDL as described in Smith et al., *J. Biol. Chem.,* 271:30647-30655 (1996). Briefly, RAW 264.7 cells in 24-well dishes were cholesterol-loaded and labeled overnight in 0.5 ml of DMEM supplemented with 50 μl/ml 1M glucose, 10 μl/ml 200 mM glutamine and 2% BSA and with 50 μg/ml acetylated low density lipoprotein (AcLDL) and [$^3$H]-cholesterol which had been pre-incubated for 30 minutes at 37° C. with AcLDL to yield a final concentration of 0.33 μCi/ml [$^3$H]-cholesterol. Cells were subsequently washed five times with PBS containing 1% BSA and incubated overnight (16-18 hours) in DMEM/BSA to allow for equilibrium of cholesterol pools.

After equilibrium of cholesterol pools, cells were rinsed four times with PBS/BSA and incubated for one hour at 37° C. with DMEM/BSA before the efflux incubations. Efflux medium (DMEM/BSA) containing either albumin alone (control), albumin plus HDL (40 μg protein/ml), or albumin plus apo A-I (10 μg/ml, Biodesign International, Kennebunk, Me.) was added and the cells were incubated for 4, 24, or 48 hours. Phospholipids were labeled by including 10 μCi/ml [$^3$H]choline (75-85 Ci/mmol, Amersham Corp.) in the DMEM/BSA overnight equilibrium medium. The radioactivity found in the culture medium was measured by scintillation counting after a 15-minute centrifugation at 12,000 g. The radioactivity in the cells was measured by scintillation counting after solubilization in 0.5 ml of 0.2M NaOH (Smith et al., *J. Biol. Chem.,* 271:30647-30655 (1996)) or extraction in hexane:isopropanol (3:2 v/v) as described in Francis, et al., *J. Clin. Invest.,* 96, 78-87 (1995). Cells containing labeled phospholipids were extracted with 1 ml of isopropanol for 1 hour and then with hexane: isopropanol as described above. The efflux of cholesterol or phospholipid was expressed as the percentage of tritiated lipid counts in the medium over the total tritiated lipid counts recovered from the cells and medium (cpm medium/cpm (medium+lysate)×100).

Figure 1A:
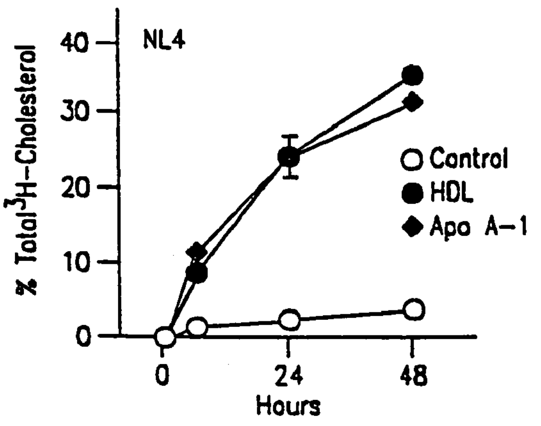
FIGS. 1A-D is a graphical representation showing the results of control cholesterol efflux and cholesterol efflux in the presence of HDL and apo A-I from normal fibroblast cells (1A, C) and fibroblast cells from Tangier disease patients (1B, D). The open circles represent the cholesterol efflux from cells that were not exposed to HDL or apo A-I, the closed circles represent the cholesterol efflux from cells exposed to HDL, and the closed diamonds represent the cholesterol efflux from cells exposed to apo A-I.
Figure 1B:
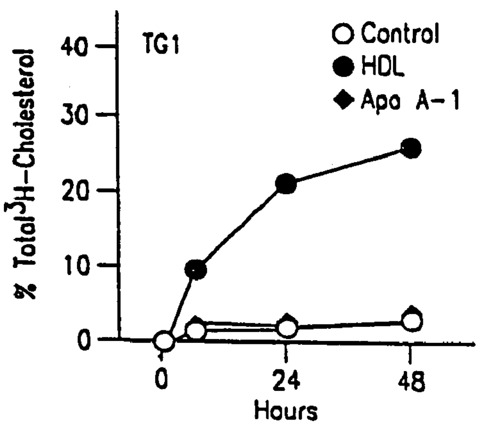
Figure 1C:
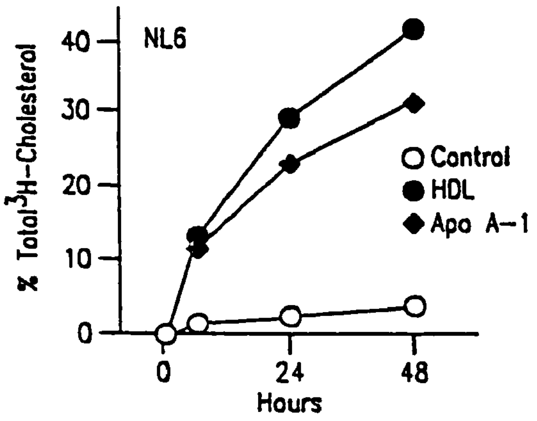
Figure 1D:
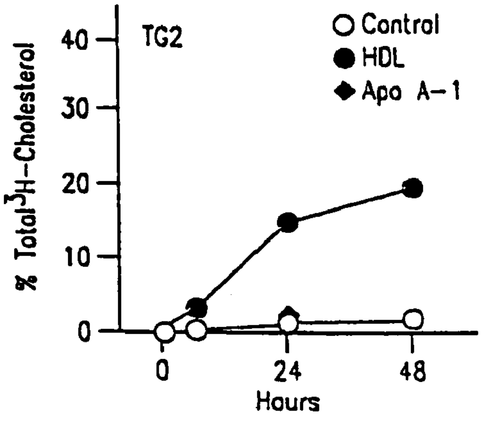

As shown in FIGS. 1A and C, the addition of HDL or apo A-I results in the removal of cholesterol from cholesterol-laden fibroblasts obtained from normal subjects. However, in TD cells, the ability of HDL to remove cholesterol is slightly diminished and the ability of apo A-I to remove cholesterol is completely absent. FIG. 1 shows that normal and TD fibroblast cells release about 3-4% of the cellular [$^3$H]-cholesterol into the medium during 48-hour incubation with albumin. Addition of HDL to the albumin medium increased the efflux of [3H]-cholesterol from both normal and TD fibroblasts, although to a lesser extent with TD cells (FIGS. 1B, D). Addition of apo A-I promoted the efflux of [$^3$H]-cholesterol from normal fibroblasts (FIGS. 1A, C), but had little or no effect on [$^3$H]-cholesterol efflux from TD fibroblasts (FIGS. 1B, D).

EXAMPLE 2

This example demonstrates that 175 genes show at least 2.5-fold decreased expression and 375 genes show at least 2.5-fold increased expression in TD cells compared with normal cells. The differential gene expression was determined using gene-expression microarray (GEM) analysis of cDNAs from normal individuals (non-TD) and from patients with TD.

Cell Cultures: The immortalized cell cultures obtained from normal individuals and TD patients described in Example 1 were used. Confluent cultures were maintained in DMEM/BSA and supplemented for 24 hours with 1 mM 8-Bromo cyclic adenosine monophosphate (8-Br-cAMP, Sigma Chemical Co., St. Louis, Mo.).

mRNA Extraction and cDNA Synthesis: mRNA from both normal and TD fibroblast cells was prepared from total RNA extracted from cells with Trizol (Life Technologies Inc., Bethesda, Md., Cat. #15596-026). The mRNA was isolated using the Oligotex mRNA kit (Qiagen Inc., Valencia, Calif., Cat. #70022) according to vendor's protocols. The mRNA was reverse transcribed using Cy3 or Cy5 fluorescent dye to create fluorescently labeled cDNA according to the method described in DeRisi et al., *Science,* 24:680-686 (1997). The resultant cDNA from TD cells was labeled with Cy3 fluorescent dye and cDNA from normal cells was labeled with Cy5 fluorescent dye (Incyte Genomics, Palo Alto, Calif.).

Microarray Analysis: To analyze differential gene expression in cells from individuals with TD and normal individuals, Cy3 and Cy5 fluorescent labeled cDNA samples prepared as described above were hybridized to a set of Gene Album microarrays (GEMs) on microscope slides (Incyte Genomics, Palo Alto, Calif.). Each of six slides contained about 9,800 human cDNA samples plus 200 control samples, resulting in a microarray of 58,800 partial cDNAs. Therefore, allowing for estimates of redundancy, approximately 30-50% of expressed human genes were represented. The hybridization of Cy3-labeled cDNA prepared from TD1 cells and Cy5-labled cDNA from normal cells allowed comparison of the relative RNA content of TD cells versus normal cells for the expressed genes. In addition, Cy3-labeled cDNA prepared from TD2 cells and Cy5-labled cDNA from normal cells were hybridized to the same set of microarrays to examine the variation of gene expression between different TD patients.

Figure 2:
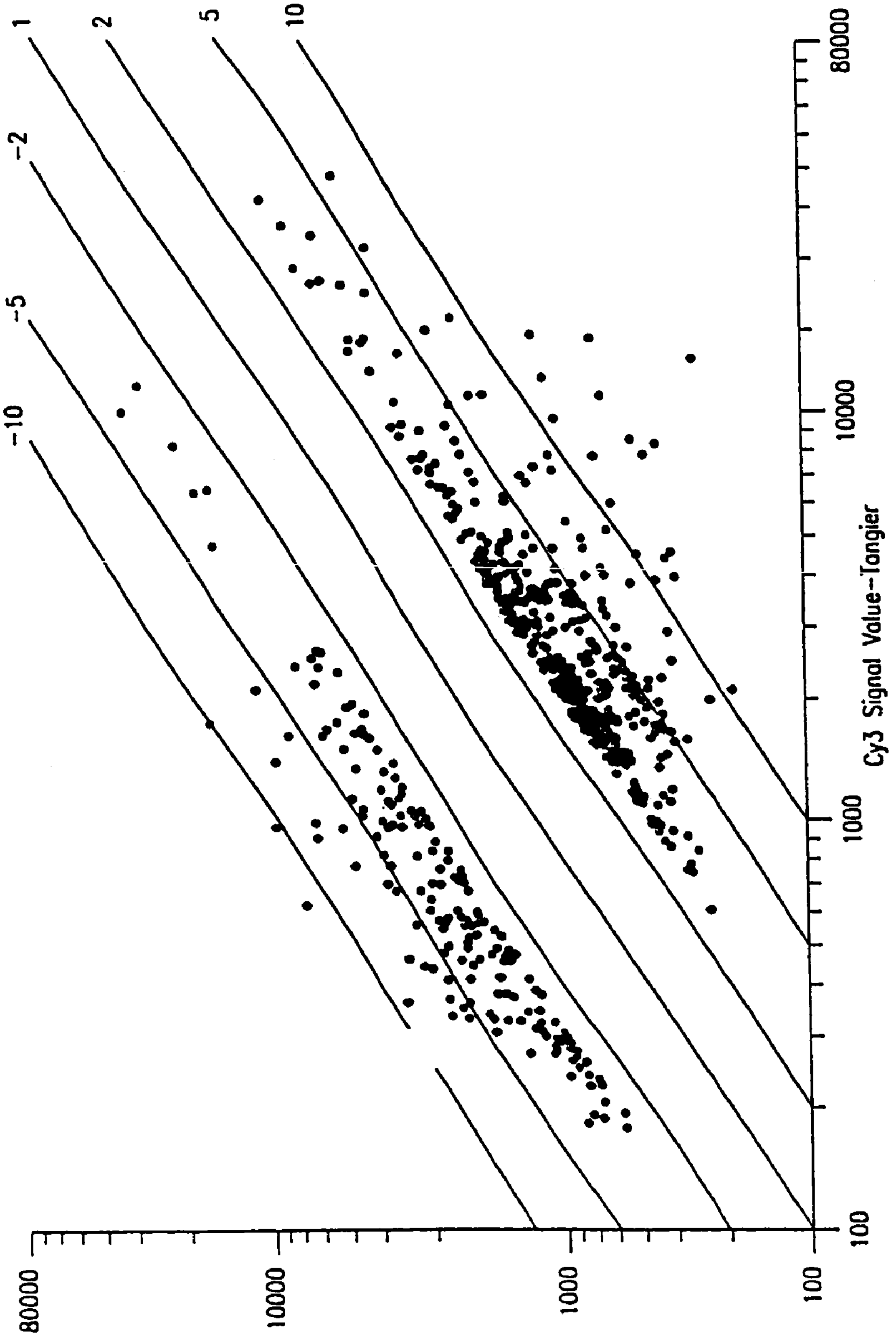
FIG. 2 is a graphical representation of a gene expression microarray analysis showing a comparison of the gene expression found in cells from a Tangier patient (TD1) and that found in normal cells, whereby a total of 58,800 human cDNAs were hybridized with cDNA prepared from mRNA of cAMP-treated TD1 cells cDNA (labeled with Cy3 dye) and with cDNA prepared from mRNA of cAMP-treated normal cells (labeled with Cy5 dye)

Results: Data were analyzed using GemTools software (Incyte Genomics, Palo Alto, Calif.) and expressed as ratios of TD cell to normal cell mRNA. The results indicated that the majority of genes are comparably expressed in TD1 and normal cells. As shown in FIG. 2 (in the section above and to the left of the diagonal) only 175 genes were more than 2.5-fold underexpressed in TD1 cells compared with normal cells, whereas 375 genes were more than 2.5-fold overexpressed in TD1 cells compared with normal cells (below and to the right of the diagonal). Genes more highly expressed in the TD cells could include those that are differentially regulated as a consequence of the Tangier mutation, either as a compensatory response or as a contributor to the disease pathology. Among the genes that could contribute to the observed phenotype of TD and are more highly expressed in TD cells include interferon-β, (IFN-β), macrophage inflammatory protein-2α, granulocyte chemotactic protein-2, IL-11, prostaglandin endoperoxide synthase-2 (COX-2), thrombospondin, and monocyte chemotactic proteins 1, 3, and 4 (Lawn et al., *J. Clin. Invest.,* 104:R25-R31 (1999).

No single RNA that was expressed in the normal fibroblasts was found completely absent in either the TD1 or TD2 cells. Also, comparison of the differentially expressed genes in TD1 and TD2 revealed very little variation between the individual TD patients. For instance, of the most highly down-regulated genes in TD2 cells, 92% were also under-expressed in TD1 cells compared with normal cells. One of the genes more than 2.5-fold under-expressed in TD1 or TD2 versus normal cells was the gene for ABC1 protein. The ABC1 gene was pursued due to the ascribed functions of some of its homologues and also because the gene was localized to the approximate chromosome region reported as the TD gene region.

EXAMPLE 3

This example demonstrates that the ABC1 gene is localized to the human chromosome 9q31.

Previous genetic linkage analysis mapped the TD gene to the 7-cM region of human chromosome 9q31 (Rust et al., *Nat. Genet.,* 20, 96-98 (1998)). In addition, in situ hybridization analyses revealed that the ABC1 gene was localized to the broader chromosomal interval 9q22-9q31 (Luciani et al., *Genomics,* 21, 150-159 (1994)). Using PCR methods with the GeneBridge 4 panel of human/hampster radiation hybrids (Research Genetics, Inc., Huntsville, Ala.), human ABC1 was determined to be located between the markers WI-14706 and WI-4062, corresponding to the 7-cM region of human chromosome 9q31. DNA from 93 human/hampster hybrid cell lines was amplified by PCR using human ABC1-specific primers LF: CCTCTCATTACA-CAAAAACCAGAC (SEQ ID NO: 11) and LR: GCTTTCTTTCACTTCTCATCCTG (SEQ ID NO: 12). Each line was scored as positive or negative for the human ABC1 amplification product and the mapping of ABC1 derived from analysis of this data was accomplished using the Whitehead Institute/MIT Center for Genome Research software, accessed via the internet. These results were further confirmed by southern blot hybridization to human genomic/yeast artificial chromosome clones (Research Genetics, Inc.) from the equivalent interval. In addition, public database searching (GeneMap '98; National Center for Biotechnology Information) and radiation hybrid mapping eliminated the other significantly underexpressed genes in the microarray data from the location in the reported genetic interval. These complementary data demonstrate that the ABC1 gene is located on human chromosome 9q31 and further indicate that the ABC1 gene is associated with Tangier disease.

EXAMPLE 4

This example shows the determination of the nucleotide sequence of the wildtype ABC1 gene, including the flanking regions and the entire coding region.

DNA sequencing was performed using an ABI Prism 310 Genetic Analyzer or by Davis Sequencing (Davis, Calif.). Both strands were sequenced throughout. The sequence of the open reading frame of the ABC1 gene from a normal subject was determined from a full-length cDNA clone obtained from an expression plasmid library constructed from normal fibroblast RNA. To construct the plasmid library, cDNA was synthesized according to the Stratagene kit protocol (Stratagene, La Jolla, Calif.). Briefly, first strand cDNA was synthesized from mRNA using an oligo-dT primer with an XhoI site and MMLV reverse transcriptase in the presence of 5-methyl dCTP. The second strand was synthesized using RNase H and DNA polymerase I in the presence of unmodified dNTPs. After the cDNA was blunt-ended with pfu DNA polymerase, an EcoRI linker was ligated to the cDNA. The cDNA was then digested with XhoI, creating XhoI ends at the 3' end of the cDNA. The internal XhoI sites were protected from this digestion due to the semi-methylation during the first strand synthesis. The synthesized cDNA was cloned into the HindIII and XhoI sites of the plasmid pCEP4 (Invitrogen Corp., Carlsbad, Calif. #VO44-50), an expression vector containing the cytomegalovirus promoter/enhancer. A 585 bp ABC1 probe was generated by reverse transcriptase polymerase chain reaction (RT-PCR) using primers based on known ABC1 sequence, which were 5'-TCCTTGGGTTCAGGGGATTATC (SEQ ID NO: 13) and 5'-CAATGTTTTTGTGGCTTCGGC (SEQ ID NO: 14). Using this ABC1 probe, a clone containing a 10.5 kb insert of human ABC1 cDNA was recovered from the library using the CloneCapture selection kit according to the manufacturer's protocol (CLONTECH Laboratories, Inc., Palo Alto, Calif.). This clone is shown in FIG. 3 as pCEPhABC1. The 10.5 kb ABC1 cDNA insert sequence is shown in SEQ ID NO: 1. Sequence determination confirmed that pCEPhABC1 contains the human ABC1 open reading frame of 6783 nucleotides plus 5' and 3' untranslated regions, having a larger open reading frame than the cDNA sequence reported by Langmann et al. in *Biochem. Biophys. Res. Comm.,* 257, 29-33 (1999) (GenBank Accession No. AJO12376).

EXAMPLE 5

This example demonstrates the sequence differences between the wildtype ABC1 gene and the TD1, TD2, and TD3 gene sequences.

cDNA Synthesis of TD1, TD2, and TD3: cDNA was prepared from TD1, TD2, and TD3 cells by reverse transciption polymerase chain reaction (RT-PCR) using the Superscript Choice cDNA system and the Advantage cDNA polymerase mix following the manufacturer's protocol (CLONTECH, Palo Alto, Calif.; Cat. #8417-1) using two sets of primer pairs designed from the normal human ABC1 gene sequence, designated: (1) saclhabcf, 5'-AGTCGAGCTCCAAACATGTCAGCTGTTACTGGAAGTGGCC (SEQ ID NO: 15); habcr3851, 5'-TCTCTGGATTCTGGGTCTATGTCAG (SEQ ID NO: 16) and (2) habcf3585, 5'-GGGAGCCTTTGTGGAACTCTTTC (SEQ ID NO: 17); habcrsalI, 5'-ACTGGTCGACCATTGAATTGCATTGCATTGAATAGTATCAG (SEQ ID NO: 18). Amplification of 0.2-0.5 μg polyA+RNA with these primers at a final concentration of 0.4 μm generated two overlapping templates of approximately 3.5 kb. The templates were gel-purified using the QIAEX II system (QIAGEN, Inc., Valencia, Calif.; Cat. #20021) and adjusted to a concentration of 100 ng/μl.

Sequencing of TD1, TD2, and TD3 cDNA: Eight μl of each template generated as described above was sequenced in a reaction with individual sequencing primers designed on the basis of wildtype ABC1 sequence at a final concentration of 0.5 μM. The primers were as follows: 1F: 5'-TTTCCTGGTGGACAATGAA (SEQ ID NO: 19), 2F: 5'-AGTGACATGCGACAGGAG (SEQ ID NO: 20); 3F: 5'-GATCTGGAAGGCATGTGG (SEQ ID NO: 21); 4F: 5'-CCAGGCAGCATTGAGCTG (SEQ ID NO: 22); SF: 5'-GGCCTGGACAACAGCATA (SEQ ID NO: 23); 6F: 5'-GGACAACCTGTTTGAGAGT (SEQ ID NO: 24); 7F: 5'-AAGACGACCACCATGTCA (SEQ ID NO: 25); 8F: 5'-ATATGGGAGCTGCTGCTG (SEQ ID NO: 26); 9F: 5'-GGGCATGAGCTGACCTATGTGCTG (SEQ ID NO: 27); 10F: 5'-AAGAGACTGCTAATTGCC (SEQ ID NO: 28); 11F: 5'-AGCGACAAAATCAAGAAG (SEQ ID NO: 29); 12F: 5'-TGGCATGCAATCAGCTCT (SEQ ID NO: 30); 13F: 5'-TCCTCCACCAATCTGCCT (SEQ ID NO: 31); 14F: 5'-TTCTTCCTCATTACTGTT (SEQ ID NO: 32); 15F: 5'-GATGCCATCACAGAGCTG (SEQ ID NO: 33); 16F: 5'-AGTGTCCAGCATCTAAA (SEQ ID NO: 34); 1R: 5'-CAAAGTTCACAAATACTT (SEQ ID NO: 35); 2R: 5'-CTTAGGGCACAATTCCACA (SEQ ID NO: 36); 3R: 5'-TGAAAGTTGATGATTTTC (SEQ ID NO: 37); 4R: 5'-TTTTTCACCATGTCGATGA SEQ ID NO: 38); 5R: 5'-CTCCACTGATGAACTGC (SEQ ID NO: 39); 6R: 5'-GTTTCTTCATTTGTTTGA (SEQ ID NO: 40); 7R: 5'-AGGGCGTGTCTGGGATTG (SEQ ID NO: 41); 8R: 5'-CAGAATCATTTGGATCAG (SEQ ID NO: 42); 9R: 5'-CATCAGAACTGCTCTGAG (SEQ ID NO: 43); 10R: 5'-AGCTGGCTTGTTTTGCTTT SEQ ID NO: 44), 11R: 5'-TGGACACGCCCAGCTTCA (SEQ ID NO: 45), 12R: 5'-CCTGCCATGCCACACACA (SEQ ID NO: 46), 13R: 5'-CTCATCACCCGCAGAAAG (SEQ ID NO: 47), 14R: 5'-CACACTCCATGAAGCGAG (SEQ ID NO: 48), 15R: 5'-TCCAGATAATGCGGGAAA (SEQ ID NO: 49), 16R: 5'-TCAGGATTGGCTTCAGGA (SEQ ID NO: 50), UTR1R: 5'-AAGTTTGAGCTGGATTTCTTG (SEQ ID NO: 51).

Results: The nucleotide numbering follows the numbering found in Lawn et al. (1999). Patient TD1 retained the full open reading frame, with 2 substantial differences from the wild-type sequence (SEQ ID NO: 8). One of these is an A to G substitution, resulting in a change from a glutamine to arginine residue at position 537 of the 2201 amino acid sequence, as published by Lawn et al. (1999). The location of this residue is within the NH2-terminal hydrophilic domain, near the first predicted transmembrane domain. Patient TD2 also retained the open reading frame with an arginine to tryptophan substitution at residue 527 (SEQ ID NO: 10). Thus, both TD1 and TD2 contain a substitution altering the charge of an amino acid in the same region of the protein. TD3 DNA contains a 14 nucleotide insertion in its ABC1 cDNA following nucleotide 5697 in one allele and a 138 bp insertion after nucleotide 5062 in the other allele.

Genomic sequencing of the TD1, TD2, and TD3 DNAs confirmed the changes found in the respective cDNAs. The genomic sequence was generated by PCR amplification of a 156 bp region of genomic DNA isolated from fibroblasts that contained the mutations found in the cDNA from TD1 and TD2. The genomic sequencing also indicated that patient TD1 was homozygous for the glutamine to arginine substitution. Genomic DNA analysis showed that TD2 was a compound heterozygote with one allele containing the detected substitution and the second allele (which failed to produce detectable mRNA) containing an undetermined defect. Neither of the substitution mutations was found in more than 80 alleles of geneomic DNA of non-TD individuals. TD3 insertions were identified by sequence analysis and confirmed by RT-PCR using primers surrounding the insertion points. The 14-bp insertion following nucleotide 5697 causes a frameshift, resulting in the replacement of the wild-type amino acid sequence from a location before the second ATP binding domain, up to the point of a premature protein termination. The 138 bp insertion following nucleotide 5062 in the other allele contains an inframe stop codon.

EXAMPLE 6

This example demonstrates that inhibitors of ABC1 transport activity also inhibit apo A-I-mediated cholesterol efflux from fibroblast cells.

Figure 5:
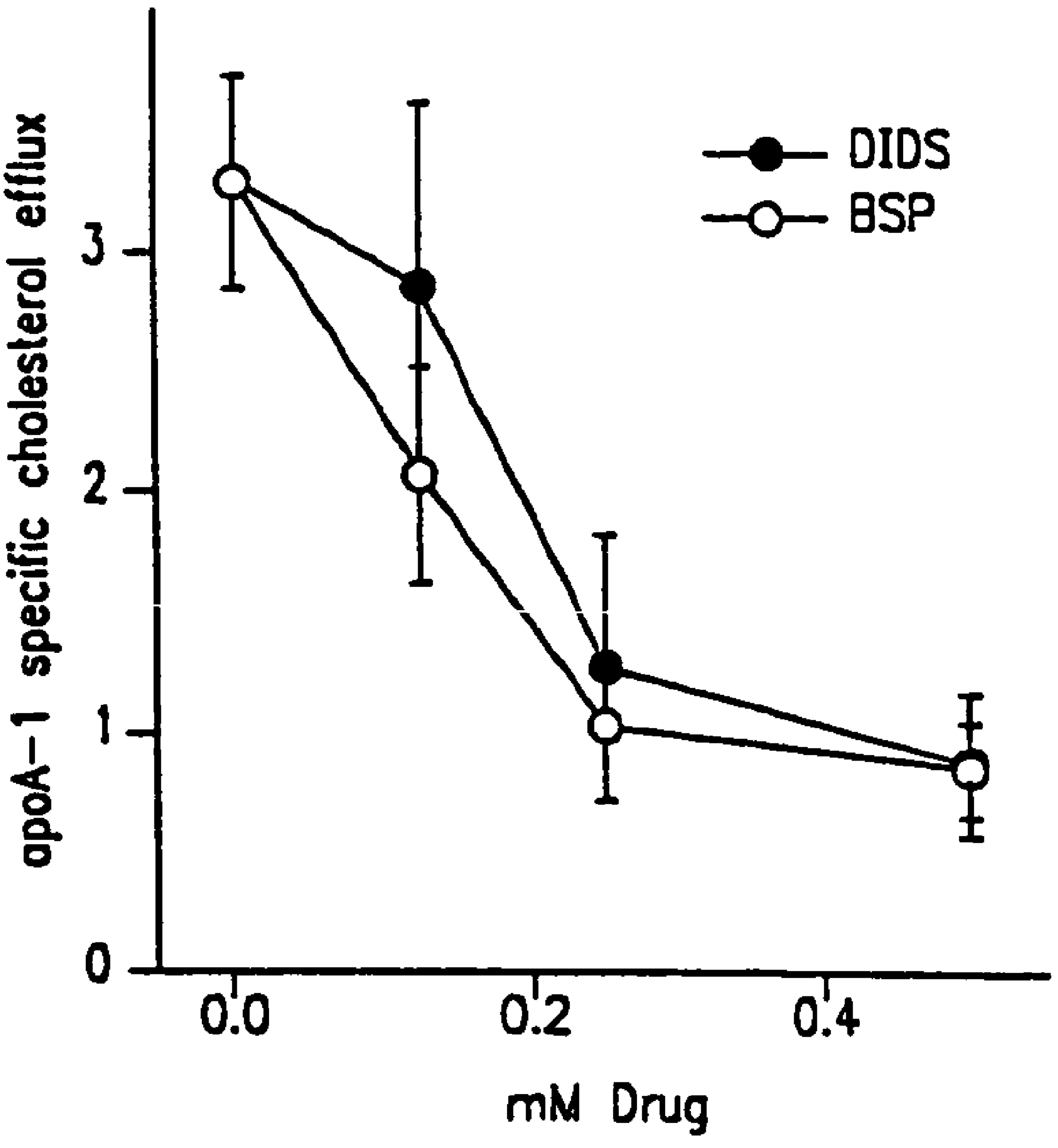
FIG. 5 is a graphical representation showing the inhibitory effect that ABC1 transport inhibitors 4,4-diisothiocyanostilbene-2,2'-disulfonic acid (DIDS) and sulphobromophtaleine (BSP) have on apo A-I-mediated cholesterol efflux, wherein the open circles indicate the apo A-I-mediated cholesterol in the presence of BSP and the closed circles indicate the apo A-I-mediated cholesterol in the presence of DIDS.

To test whether inhibition of ABC1 could affect the process of apolipoprotein-mediated cholesterol efflux, two compounds reported to be ABC1 inhibitors were tested in assays which monitor apolipoprotein mediated cholesterol efflux. The compounds 4,4-diisothiocyanostilbene-2,2'-disulfonic acid (DIDS) and sulphobromophthaleine (BSP) were reported to inhibit anion transport activities of ABC1 in a dose-dependent fashion (Becq et al., *J. Biol. Chem.,* 272: 2695-2699 (1997); Hamon et al., *Blood,* 90:2911-2915 (1997)). The apolipoprotein-mediated cholesterol efflux assays were performed as described in Example 1 with the noted changes. Cholesterol-loaded and [$^3$H]cholesterol-labeled normal fibroblasts (n=3) were incubated for 6 hours with or without 5 μg/ml apo A-I and either 0, 0.2 mM, or 0.4 mM DIDS. In addition, cholesterol-loaded and [$^3$H]cholesterol-labeled normal fibroblasts (n=3) were incubated for 6 hours with or without 5 μg/ml apo A-I and either 0, 0.2 mM, or 0.4 mM BSP. [$^3$H]cholesterol efflux was measured by scintillation counting as described in Example 1 and calculated as the percentage of total radiolabeled cholesterol appearing in the medium. The results are shown in FIG. 5 as the mean±SD (n=3) of efflux in the presence of apo A-I after subtraction of values for apo A-I-free medium. FIG. 5 shows that both DIDS and BSP inhibit the 6-hour efflux of tritiated cholesterol mediated by apolipoprotein A-I. In addition, similar inhibition was observed with the efflux of tritiated phosphatidyl choline using DIDS and BSP (data not shown). The results of these tests mimic the efflux defect in fibroblasts derived from patients with TD, described in Example 1.

EXAMPLE 7

This example demonstrates that antisense inhibition of ABC1 mRNA expression inhibits apo A-I-mediated cholesterol efflux from fibroblast cells.

Figure 6:
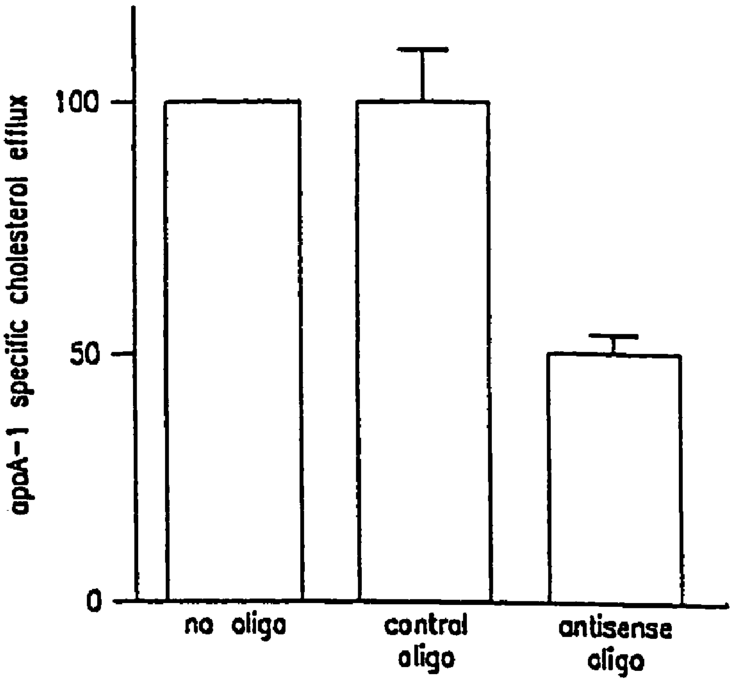
FIG. 6 is a graphical representation showing the inhibitory effect of an antisense ABC1 oligonucleotide on apo A-I-mediated cholesterol efflux, showing the apo A-I-mediated cholesterol efflux in cells incubated without antisense oligonucleotide, the apo A-I-mediated cholesterol efflux in cells exposed to 30 μM β-globin antisense oligonucleotide, and the apo A-I-mediated cholesterol efflux in cells exposed to 30 μM ABC1 antisense oligonucleotide.

Normal skin fibroblasts were labeled with [$^3$H]cholesterol as described in Example 1. The cells were then loaded with oligonucleotide by scraping in the presence of either 30 μM control Morpholino oligonucleotide (5'-CCTCTTACCTCAGTTACAATTTATA-3' corresponding to the antisense complement of a β-globin thalassemic mRNA; SEQ ID NO: 52) or 30 μM ABC1 antisense Morpholino oligonucleotide (5'-CATGTTGTTCATAGGGTGGGTAGCTC-3'; SEQ ID NO: 53) and reseeding on new dishes. Control cells were mock-loaded after [$^3$ H]cholesterol-labeling by scraping and reseeding in the absence of oligonucleotide. Apo A-I-mediated efflux was measured after 12 hours by scintillation counting as the percentage of total radiolabeled cholesterol appearing in the medium. The results are shown in FIG. 6 as the mean±SEM of three separate experiments, normalized to the value for apo A-I-specific efflux in the absence of oligonucleotide in each experiment. As shown in FIG. 6, antisense oligonucleotides directed against ABC1 mRNA caused a 50% reduction in cholesterol efflux from normal fibroblasts compared with control antisense oligonucleotide (β-globin antisense oligonucleotide).

EXAMPLE 8

This example demonstrates that over expression of the human ABC1 gene results in an increase in apo A-I-mediated cholesterol efflux from monocyte cells.

Stable Transfection of RAW 264.7 Cells: Mouse monocytic RAW 264.7 cells were stably transfected with the pCEPhABC1 expression plasmid for human ABC1. Construction of the pCEPhABC1 plasmid containing the open reading frame of human ABC1 is described in Example 4. Approximately $1\times10^6$ RAW 264.7 cells were transfected for 5 hours with 2 μg of pCEPhABC1 DNA and 12 μl Geneporter transfection reagent (Gene Therapy Systems, Inc., San Diego, Calif.; Cat. #T201007) in 0.8 ml serum-free DMEM. Two days later, cells were split at ratios ranging from 1:2-1:50 and selection applied by adding 150 μg/ml hygromycin to the culture medium. After two weeks, hygromycin-resistant colonies were picked and expanded.

Figure 7:
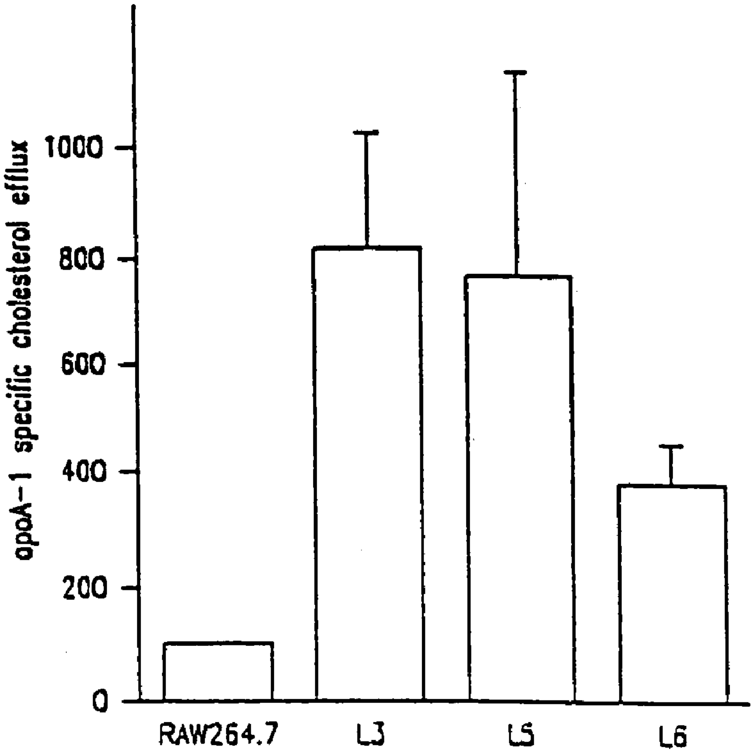
FIG. 7 is a graphical representation demonstrating the stimulation of apo A-I-mediated cholesterol efflux caused by overexpression of the ABC1 gene using RAW 264.7 mouse macrophage cells stably transfected with an expression plasmid for human ABC1 (pCEPhABC1), showing the apo A-I-mediated cholesterol efflux in control parental cells (no pCEPhABC1) and the apo A-I-mediated cholesterol efflux in clonal cells transfected with pCEPhABC1 (L3, L5, L6)

Apo A-I-mediated Cholesterol Efflux Assay: Parental RAW 264.7 cells and three clonal lines (L3, L5, and L6) stably expressing human ABC1 were grown to confluence. The cells were cholesterol-loaded and labeled by incubation for 24 hours with 0.5 μCi/ml [$^3$H]cholesterol and 50 μg/ml acetylated LDL as described in Example 1. After equilibrium of cholesterol pools by an overnight incubation in DMEM/BSA, cells were washed and the efflux medium was added as described in Example 1. Apo A-I-mediated cholesterol efflux was measured as previously described by scintillation counting of the tritiated cholesterol in the cell medium, expressed as a percentage of the total counts recovered from the cells and medium. The results are presented as the mean±SEM of three separate experiments normalized to the value for apo A-I-specific efflux from parental RAW 264.7 cells within each experiment. FIG. 7 shows the apo A-I-mediated cholesterol efflux from parental RAW 264.7 cells and L3, L5, and L6 transfected cell lines. As can be seen, transfection with the ABC1 expression vector results in a 4-fold (L6) to 8-fold (L3 and L5) increase in apo A-I-mediated cholesterol efflux. These results indicate that overexpression of the ABC1 gene can substantially increase the amount of cholesterol efflux from macrophage cells.

EXAMPLE 9

This example demonstrates that ABC1 mRNA expression is regulated by cellular conditions related to cholesterol efflux in normal skin fibroblasts, but not in TD fibroblasts.

To determine whether ABC1 plays a rate-limiting role in cellular sterol efflux, the synthesis of ABC1 was measured under various cellular conditions related to cholesterol efflux processes. Specifically, normal fibroblasts and TD fibroblasts were individually exposed to conditions of excess cAMP, cholesterol, or Apo A-I. Cell cultures of normal skin fibroblasts and TD1 and TD2 fibroblasts were prepared as described in Example 1. The level of ABC1 mRNA was measured by RT-PCR.

Cell cultures: Immortalized cell cultures of normal skin fibroblasts and TD1 and TD2 fibroblasts were prepared as described in Example 1. Cells were grown to subconfluence in DMEM/10% FBS before replacement with DMEM/BSA and the indicated additive for 24 or 48 hours. RNA was prepared as described in Example 2.

RT-PCR: Quantitative PCR was carried out using the GeneAmp 5700 Sequence Detection System (Perkin-Elmer Applied Biosystems, Foster City, Calif.). Briefly, 500 ng of DNase-treated mRNA was reverse transcribed using random hexamer primers at 2.5 μM. Approximately 5% of this reaction was amplified by PCR using the SYBR green core kit (PE Applied Biosystems, Foster City, Calif.; Cat. #4304886) and human ABC1 primers LF: 5'-CCTCTCATTACACAAAAACCAGAC (SEQ ID NO: 11) and LR: 5'-GCTTTCTTTCACTTCTCATCCTG (SEQ ID NO: 12) to yield an 82 bp fragment corresponding to nucleotides 7018-7099 of human ABC1. PCR cycle conditions were as follows: 10 minutes 95° C.; followed by 40 cycles of 95° C., 15 seconds; and 60° C., 60 seconds. The mRNA in each sample was quantitated by detecting the increase in fluorescence caused by SYBR green binding to the double-stranded amplification product generated during each PCR cycle. All samples were run in triplicate and normalized against β-actin mRNA, amplified in parallel reactions with primers actinF: 5'-TCACCCACACTGTGCCATCTACGA (SEQ ID NO: 54) and actinB: 5'-CAGCGGAACCGCTCATTGCCAATGG (SEQ ID NO: 55). Standard curves were run for both ABC1 and β-actin on the same PCR plate.

8-Br-cAMP Assay: Normal, TD1, and TD2 fibroblast cells were grown to subconfluence in DMEM/10% FBS and then treated with 1 mM 8-Br-cAMP in DMEM/BSA for 24 hours.

Cholesterol Assay: Normal, TD1, and TD2 fibroblast cells were grown to subconfluence in DMEM/10% FBS and then treated with 30 μg/ml free cholesterol in DMEM/BSA for 48 hours followed by 18-24 hours of equilibrium in DMEM/BSA.

Apo A-I Assay: Normal, TD1, and TD2 fibroblast cells were grown to subconfluence in DMEM/10% FBS and then treated with 30 μg/ml free cholesterol in DMEM/BSA for 48 hours followed by 18-24 hours of equilibrium in DMEM/BSA plus 10 μg/ml apo A-I.

Results: FIG. 8 shows that in normal fibroblasts ABC1 mRNA is increased approximately 10-fold by exposure to 8-Br-cAMP and increased approximately 17-fold by exposure to cholesterol in serum-free medium. Subsequent exposure of cholesterol-loaded cells to Apo A-I results in a marked decrease in ABC1 mRNA expression. Although the mechanism has not been demonstrated, previous studies have shown that cholesterol efflux is promoted in the presence of such compounds as cAMP and cholesterol (Hokland et al., *J. Biol. Chem.,* 268:25343-25349 (1993)). The present results indicate that in normal fibroblasts, ABC1 mRNA is induced by these known effectors of the cholesterol efflux pathway and repressed by exposure to an apolipoprotein cholesterol acceptor, demonstrating that the expression of ABC1 is regulated by cellular conditions related to apolipoprotein-mediated cholesterol efflux. In contrast, fibroblast cells from TD patients are not regulated by effectors of cholesterol efflux. First, the cAMP-inducible level of ABC1 mRNA in both TD1 and TD2 cells is only approximately 40% of that in normal cells. Further, exposure of cholesterol-loaded cells to Apo A-I either did not alter ABC1 expression (TD1 cells) or slightly increased ABC1 expression (TD2 cells). These results reflect the defect in Apo-A-I-mediated cholesterol efflux described for TD cells. Interestingly, growth of cells in serum-containing medium suppressed ABC1 message to near the limit of detection (data not shown). This may reflect the fact that functioning of the lipid efflux pathway requires cell quiescence or other cellular states of reduced cholesterol need. In conclusion, conditions that are associated with increased efflux of cellular cholesterol (i.e., cholesterol loading, cAMP treatment, serum deprivation) also result in increased expression of ABC1 mRNA in normal fibroblast cells. Conversely, exposure of cholesterol-loaded normal fibroblast cells to apo A-I reduces ABC1 expression.

EXAMPLE 10

This example demonstrates that ligands for the LXR nuclear receptor, such as 20-hydroxycholesterol, and ligands for the RXR receptor, such as 9-cis retinoic acid, can increase ABC1 gene expression in mouse RAW 264.7 cells.

LXR nuclear receptors are transcription factors that form obligate heterodimers with the nuclear receptor RXR, and are activated to enhance transcription of their target genes by binding a class of oxysterols including 22-hydroxycholesterol and 20-hydroxycholesterol (Janowski et al., *Nature,* 383:728-731 (1996)). As such, they are candidates for the mediation of cholesterol-induced gene transcription. Further, in light of studies which showed that ABC1 mRNA and protein increase in fibroblasts and macrophages in response to cholesterol loading, and other studies which showed that LXR and RXR expression increase in cholesterol-loaded macrophage cells by exposure to oxidized LDL, the LXR and RXR nuclear receptors are highly plausible candidates for transcriptional activators of the ABC1 gene. To determine whether LXR and RXR receptors play a role in ABC1 gene expression, the level of ABC1 mRNA was measured in response to 20-hydroxycholesterol and 9-cis retinoic acid.

Figure 9:
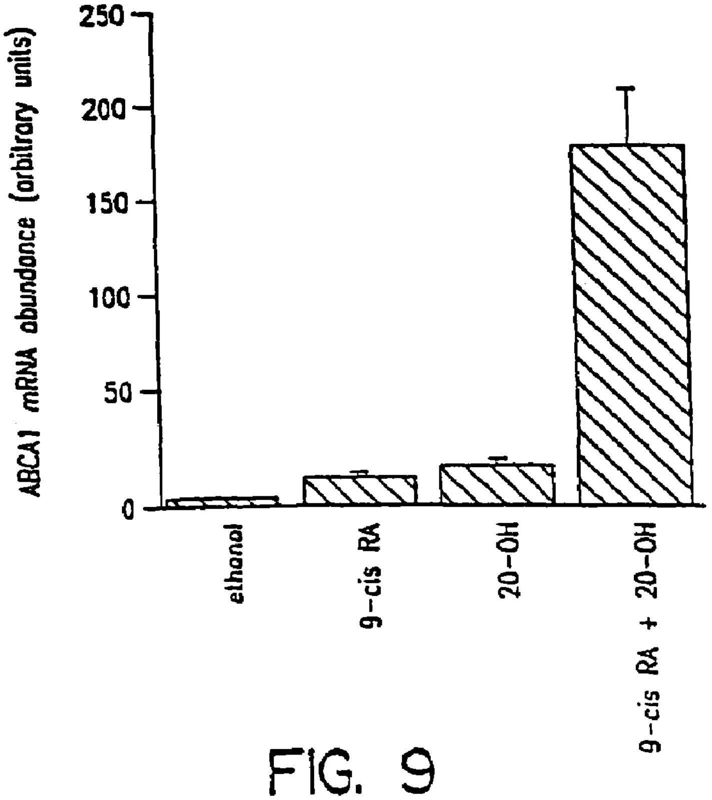
FIG. 9 is a graphical representation of the results of RT-PCR analyses showing the level of ABC1 gene expression in RAW 264.7 cells exposed to either ethanol (0.1% v/v), 9-cis retinoic acid (9-cis RA; 10 μM), 20(S) hydroxycholesterol (20(S)—OH; 10 μM), or 9-cis RA and 20(S)—OH (10 μM each)

Mouse RAW 264.7 cells were grown to subconfluence in DMEM/10% FBS and then treated for 24 hours in serum-free DMEM/BSA with either 9-cis retinoic acid (10 μM), 20-hydroxycholesterol (10 μM), or both ligands together (20 μM total). Control cells received ethanol vehicle only (0.1% v/v). RNA was extracted, treated with DNase, and ABC1 mRNA measured by RT-PCR using PE Biosystems SYBR Green Technology as described in Example 9. FIG. 9 shows that treatment with either 20-hydroxycholesterol or 9-cis retinoic acid results in an increase in ABC1 mRNA expression. In addition, FIG. 9 shows that treatment with both ligands together results in a markedly synergistic effect, with an approximate 6-fold increase over the ABC1 expression observed with either ligand alone. These results demonstrate that ligands for the nuclear receptors LXR and RXR can increase the expression of the ABC1 gene.

EXAMPLE 11

This example demonstrates that enhanced expression of ABC1 protein in the plasma membrane is associated with lipid efflux.

Cell-surface labeling and immunoprecipitation was used to determine whether increased expression of ABC1 protein in the plasma membrane is correlated with an increase in cholesterol efflux (FIG. 10). The relative amount of ABC1 on the cell surface was determined by cross-linking surface proteins on intact cells with the membrane-impermeable agent sulfo-NHS-biotin, followed by the steps of membrane solubilization, immunoprecipitation with ABC1 antibody, SDS-PAGE, and detection with streptavidin.

Cell Culture: Normal and TD1 fibroblast cells were immortalized as described in Example 1. Both normal and TD1 cells were cultured under control conditions and conditions known to increase apolipoprotein-mediated cholesterol efflux (Oram, et al., *J. Lip. Res.*, 40: 1769-1781 (1999)). Control cells were grown to confluence in DMEM/10% FBS and then incubated in DMEM/BSA for 18 hours with no additives (control). cAMP-treated cells were grown to confluence in DMEM/10% FBS and then incubated in DMEM/BSA for 18 hours with 1 mM 8-Br-cAMP(cAMP). Cholesterol-loaded cells were grown to confluence in DMEM/10% FBS and then incubated in DMEM/BSA for 48 hours with 30 μg/ml cholesterol plus 18 hours with no additives (cholesterol). Cholesterol-loaded cells treated with cAMP were grown to confluence in DMEM/10% FBS and then incubated in DMEM/BSA for 48 hours with 30 μg/ml cholesterol plus 18 hours with 1 mM 8-Br-cAMP (cholesterol+cAMP).

Cell-Surface Labeling: For selective labeling of plasma membrane ABC1, the cells were incubated for 30 minutes at 0° C. with PBS containing 1 mg/ml sulfo-NHS-biotin (Pierce, Rockford, Ill.; Cat. #21217) to biotinylate cell-surface proteins (see Walker et al., *Biochemistry,* 50:14009-14014 (1993)).

Immunoprecipitation: Rabbit antiserum for ABC1 was raised against a synthetic peptide corresponding to the deduced peptide KNQTVVDAVLTSFLQDEKVKES (SEQ ID NO: 60) located at the C-terminus of human ABC1. Immunoprecipitation was performed by solubilizing the cells in PBS containing 1% Triton X-100 (Sigma, St. Louis, Mo.) and protease inhibitors leupeptin (1 mM), pepstatin (1 mM), and aprotinin (1 mM). The cell extract was incubated overnight at 4° C. with anti-ABC1 antiserum at 1:200 dilution followed by an additional 1 hour incubation with 5 μl proteinA-coated magnetic beads (Dynal, Lake Success, N.Y.; Cat. #1001.01). The antibody-antigen complex was sedimented with a magnet, the beads were washed twice with 1% Triton-X/PBS, and the proteins were eluted with 1% acetic acid.

Detection of ABC1 Protein: The eluted biotinylated proteins were subjected to SDS-PAGE (6% gel; 150V, 5 hours) and transferred to nitrocellulose membrane (200 mA, 18 hours). The nitrocellulose was probed with streptavidin-horse radish peroxidase (Amersham Pharmacia, Piscataway, N.J.; Cat. #RPN 1231) diluted 300-fold and detected by enhanced chemiluminescence labeling (ECL) according to vendor's protocol (Amersham Pharmacia, Piscataway, N.J.). To test for possible biotinylation of intracellular proteins, the post-immunoprecipitation supernatant was treated with a mouse monoclonal antibody to the intracellular protein β-COP and immunoprecipitated biotinylated β-COP was assayed by streptavidin blotting. None was detected.

Results: As shown in FIG. 10, the 240 kDa ABC1 protein appears as a doublet. The ABC1 protein is partially localized to the plasma membrane in both normal (10A) and TD1 (10B) fibroblast cells. Similar results were seen with a second normal fibroblast cell line and with TD2 fibroblasts (data not shown). Cell-surface expression of ABC1 was increased slightly when cells grown in serum (normal and TD1 cells) were treated with 8-Br-cAMP. Serum deprivation and cholesterol-loading of both normal and TD1 cells markedly increased cell-surface expression of ABC1, which was further enhanced by cAMP treatment. These results indicate that expression of ABC1 at the cell surface is regulated by conditions that enhance apolipoprotein-mediated lipid efflux, consistent with the idea that its localization to the plasma membrane plays a key role in its lipid transport function. The mutations in TD1 and TD2 cells do not appear to severely impair expression or processing of ABC1, implying that secondary effects on lipid transport or interactions with accessory proteins depend on its NH2-terminal domain, where the mutations occur.

EXAMPLE 12

This example shows that agents that inhibit the degradation of 3'5' cyclic AMP, such as phosphodiesterase inhibitors, increase apolipoprotein A-I-mediated efflux from macrophage cells.

As shown in FIG. 10, cAMP increases the activity of ABC1. The present studies were performed to determine the cholesterol efflux from macrophage cells in the presence of elevated cAMP. Elevated levels of cAMP can be attained in the presence of agents that either stimulate cAMP synthesis or inhibit the degradation of cAMP. For example, rolipram is a compound that regulates cAMP levels by inhibiting phosphodiesterases, a group of enzymes that degrade cAMP. The effect of elevated cAMP on cholesterol efflux was determined using the apolipoprotein-mediated cholesterol efflux assays described in Example 1. Briefly, RAW 264.7 cells suspended at a density of $1.25 \times 10^5$ cells/ml were grown in DMEM/10% FBS supplemented with pyruvate. After 24 hours, the medium was removed and replaced with DMEM/BSA plus radiolabeled cholesterol (1 μCi/ml $^3$[H]-cholesterol) and 50 μg/ml of acetylated LDL for 24 hours. The cells were then maintained for 24 hours in equilibrium medium consisting of DMEM/BSA plus either apo A-I alone (20 μg/ml), apo A-I and 8-bromo 3', 5' cAMP (1 mM) or apo A-I and rolipram (50 μM). After 12-24 hours, [$^3$H]cholesterol efflux was measured by scintillation counting as described in Example 1 and calculated as the percentage of total radiolabeled cholesterol appearing in the medium. The results indicated that cholesterol-loaded control cells that received no apo A-I showed a 3% cholesterol efflux, while cells that received apo A-I only showed a 5% efflux. Cholesterol-loaded cells that received apo A-I and cAMP showed a 32% cholesterol efflux, demonstrating that elevated cAMP promotes cholesterol efflux. Similarly, cells that received apo A-I and a phosphodiesterase inhibitor (rolipram) showed a 17% cholesterol efflux.

EXAMPLE 13

This example shows that agents that are ligands for nuclear receptors, such as LXR, RXR, and PRAR nuclear receptors, increase apolipoprotein A-I-mediated efflux from macrophage cells.

To determine whether ligands for nuclear receptors affect the process of apolipoprotein-mediated cholesterol efflux, various ligands were tested using the apo A-I-mediated cholesterol efflux assay described in Example 12. The nuclear receptor superfamily includes several members, such as the liver receptor LXR, the retinoid receptor RXR, and the peroxisome proliferator-activated receptor PPAR, which have been implicated in lipid metabolism (Russell. D. W., *Cell,* 97:539-542 (1999); Spiegelman, B. W., *Cell,* 93:153-155 (1998); Janowski et al., *Nature,* 383:728-731 (1996)). Further, ligands for some of these receptors have been observed to increase plasma HDL and gene expression profiling (microarray) data have shown that hormone receptors respond to cholesterol loading via oxidized LDL. Using the above-described assay, 9 cis-retinoic acid (RXR ligand), oxysterol (LXR ligand), and fenfibrate (PPAR ligand) was tested to determine the effect on cholesterol efflux. Cholesterol-loaded control cells that received no apo A-I showed a 3% cholesterol efflux, while cells that receive apo A-I only showed a 5% efflux. In contrast, cholesterol-loaded cells that receive apo A-I and 9 cis-retinoic acid (30 ng/ml) showed a 16% cholesterol efflux. Cells that receive apo A-I and oxysterol (5 μg/ml) showed a 14% cholesterol efflux. Cells that receive apo A-I and fenfibrate (3 μg/ml) showed a 10% cholesterol efflux. These results indicate that hormone receptors may be modulated to increase the rate of apolipoprotein-mediated cholesterol efflux from macrophages.

Further, when the efflux assay was performed using various concentrations of 9-cis-RA (0.3 ng/ml, 3.0 ng/ml, or 30 ng/ml), the results showed that 9-cis-RA mediated cholesterol efflux from macrophage cells in a dose-dependent manner. Specifically, control cells (apo A-I only) showed 1890 c.p.m., 0.3 ng/ml 9-cis-RA showed 1522 c.p.m., 3.0 ng/ml 9-cis-RA showed 3568 c.p.m., and 30 ng/ml 9-cis-RA showed 8597 c.p.m. In addition, using a similar assay where RAW 264.7 cells were cholesterol-loaded for 48 hours, other nuclear receptor activators, such as 22-hydroxycholesterol (LXR ligand) and benzfibrate, were shown to increase cholesterol efflux (data not shown).

EXAMPLE 14

This example shows that eicosanoids, such as prostaglandin E1 and prostacyclin PG12, increase apolipoprotein A-I-mediated efflux from macrophage cells.

Eicosanoids, such as prostaglandins and prostacyclins, have been shown to be effective in the treatment of hypercholesterolemia. To determine whether eicosanoids affect the process of apolipoprotein-mediated cholesterol efflux, PGE1 and PG12 were tested using the apo A-I-mediated cholesterol efflux assay described in Example 12. This assay showed that cholesterol-loaded control cells that receive no apo A-I have a 3% cholesterol efflux, while cells that receive apo A-I only have a 5% efflux. Cholesterol-loaded cells that receive apo A-I and PG12 (25 nm) showed a 10% cholesterol efflux. Cells that receive apo A-I and PGE1 (25 nM) showed a 15% cholesterol efflux. These results demonstrate that eicoasnoids can increase the rate of apolipoprotein-mediated cholesterol efflux from macrophages.

EXAMPLE 15

This example demonstrates that a reporter gene under the control of an ABC1 promoter can be used to test compounds for the ability to regulate ABC1 gene expression.

The pGL3 luciferase reporter vector system (Promega, Madison, Wis.) was used to create a recombinant plasmid to measure reporter gene expression under control of the ABC1 promoter.

Construction of Reporter Plasmids: Plasmid pGL3-Basic (Promega, Madison, Wis.; Cat. #E1751) was used as a control plasmid containing the promoterless luciferase gene. The reporter construct containing the ABC1 promoter and luciferase gene was made by cloning a genomic fragment from the 5' flanking region of the ABC1 gene (hAPR1 5' promoter, corresponding to nucleotides 1080-1643 of SEQ ID NO: 3) into the SacI site of the GL3-Basic plasmid to generate plasmid GL-6a. Next, plasmid GL-6a was digested with SpeI and Acc65I. A BsiWI-SpeI fragment excised from a lambda subclone, representing the ABC1 genomic sequence corresponding to nucleotides 1-1534 of SEQ ID NO: 3 was ligated into the remaining vector/ABC1 promoter fragment produced by this digestion. The resultant plasmid, pAPR1, encodes the luciferase reporter gene under transcriptional control of 1.75 kb of the human ABC1 promoter sequence.

Transfection of Reporter Constructs: The above-described control or pAPR1 plasmid was transfected into confluent cultures of RAW 264.7 cells maintained in DMEM containing 10% fetal bovine serum. Each well of a 12 well dish was transfected for 5 hours with either pGL3-Basic, pGL3-Promoter or pAPR1 DNA (1 μg), luciferase plasmid DNA (1 μg), and 12 μl of Geneporter reagent (Gene Therapy Systems, San Diego, Calif.; Cat. #T201007). In addition, 0.1 μg of pCMVβ plasmid DNA (Clontech, Palo Alto, Calif., Cat. #6177-1) was added as a control for transfection efficiency. After 5 hours, the culture medium was replaced with serum-free DMEM/BSA in the presence of or absence of acetylated LDL (100 μg/ml) and incubated for 24 hours.

For added convenience in high throughput screening, cultured cells can be stably transfected with reporter plasmids using the following procedure. First, $5\times10^6$ RAW 264.7 cells are transfected for 5 hours in a 60 mm dish with 9 μg of the pAPR1 plasmid and pCMVscript (Stratagene, LaJolla, Calif.) in 10 ml of serum-free DMEM with 50 μl Geneporter transfection reagent (Gene Therapy Systems, San Diego, Calif.). Subsequently, the transfection medium is replaced with complete medium and the cells incubated overnight at 37° C. Subsequently, the cells are transferred to separate dishes at dilutions ranging from 1:5 to 1:1000 and incubated in selection medium containing 800 μg/ml G418 (Life Technologies, Bethesda, Md.) for 20 days. Visible colonies are picked, expanded, and assayed for luciferase activity as described below. Using this method, five clonal cell lines positive for luciferase activity were identified for use in high throughput assays.

Luciferase Assay: Following transfection, the cells in each well were lysed in 70 μl of 1X cell lysis reagent (Promega, Madison, Wisc., Cat. #E3971), subjected to one freeze-thaw cycle, and the lysate cleared by centrifugation for 5 minutes at at 12,000 g. After centrifugation, 100 μl of luciferase assay reagent (Promega, Madison, Wisc.; Cat. #E1501) was added to 10 μl of lysate. The luciferase activity of each lysate was measured as light units using a luminometer. Additionally, the β-galactosidase activity of each lysate was measured using the chemiluminescent assay reagents supplied in the Galacto-light kit according to the manufacturer's instructions (Tropix Inc., Bedford, Mass.: Cat. #BL100G). The normalized luciferase activity for each lysate was determined by dividing the luciferase activity value by the determined β-galactosidase value and reported as relative light units.

Results: The luciferase activity detected in cells transfected with pAPR1 was 3.3-fold higher than the activity detected in control cells transfected with pGL3-Basic plasmid containing luciferase cDNA only. These results indicated that the transcriptional regulatory regions of ABC1 were in place. When the pAPR1 transfected cells were incubated with 100 μg/ml acetyl LDL for 24 hours, the luciferase activity was 3.25-fold higher than in cells that had not been treated with acetyl LDL. These results suggest that the genomic ABC1 sequence contains a "cholesterol responsive" element found in the 5'flanking region which mediates the cholesterol loading response of the native ABC1 gene. This reporter system can also be used to test other compounds to determine whether the compound modulates ABC1 expression.

EXAMPLE 16

This example demonstrates an additional assay that can be used to test compounds for the ability to regulate ABC1 gene expression using a reporter gene under the control of an endogenous ABC1 promoter.

This assay involves constructing a recombination vector that contains a promoterless reporter gene and a selection marker gene. The vector is linearized and transfected into cells such that the reporter gene is integrated into the cellular genome downstream of the endogenous ABC1 promoter. Using this assay, expression of the reporter gene is driven by the endogenous ABC1 promoter in response to a test compound.

Construction of Reporter Plasmids: The recombination vector containing a promoterless reporter gene can be made starting with a 7 kb EcoRI genomic fragment of ABC1 that contains exon 0 (which includes the ABC1 start sites) and part of intronl. Using site-directed mutagenesis, a SalI restriction site can be generated in the exon 0 sequence downstream of the two known start sites. The recombination vector is generated by inserting a DNA fragment containing a promoterless reporter gene, such as luciferase, and a promoterless selective marker, such as puromycin resistance, into the SalI site. An internal ribosome entry signal should be inserted between the reporter gene and marker gene so that the genes will be transcribed in the correct orientation. The recombination vector contains two Eco47III sites, one of which must be eliminated, using, for example, site-directed mutagenesis. The remaining Eco47III site, located upsteam of of exon 0, is used to linearize the vector.

Transfection of Reporter Constructs: The linearized recombination vector containing the reporter gene and marker gene is introduced into cultured cells, including human cells, by any of the various transfection methods known in the art. For example, the linearized vector can be transfected using the methods described in Example 15. The linearized recombination vector contains ABC1 sequences which allow the vector to integrate into the cellular genome at the site of the endogenous ABC1 gene. The addition of an appropriate antibiotic to the culture medium allows the selection of only those cells in which the reporter gene and marker gene have integrated downstream of the endogenous ABC1 promoter in the proper orientation. For instance, if the vector contains a puromycin resistance gene inserted downstream of the reporter gene, the transfected cells should be grown in the presence of puromycin. Only those cells that have a properly integrated puromycin resistance gene, and can thereby encode a functional protein, will survive in the presence of puromycin. Thus, the transfected cells should be grown under conditions that induce ABC1 promoter activity in the presence of the appropriate antibiotic. Surviving cells can be clonally cultured and the DNA sequenced using PCR or southern blot analysis to test for proper integration of genomic sequences.

The resultant cells containing a reporter gene under the control of the endogenous ABC1 promoter can be used to determine whether a test compound modulates the expression of ABC1. The ABC1 modulating activity of a compound is determined by assaying the level of reporter gene expression found in the cells exposed to the test compound. For example, cells having an integrated luciferase gene can be used to determine the ABC1 modulating activity of a test compound by measuring the amount of luciferase activity found in cells exposed to the compound.

EXAMPLE 17

This example demonstrates that ligands for nuclear receptors up-regulate the expression of a reporter gene under the control of the ABC1 promoter.

To determine whether ligands for the LXRα, LXRβ and RXRα nuclear receptors could regulate ABC1 gene expression, the pAPR1 plasmid containing the luciferase reporter gene under control of the ABC1 promoter was transfected into RAW 264.7 cells treated with at least one ligand for the nuclear receptors (FIG. 12).

Construction and Transfection of Reporter Constructs: Reporter construct pAPR1 and control reporter construct pGL3-Basic were obtained as described in Example 15. RAW 264.7 cells were maintained in culture and transfected with either pGL3-Basic (1 μg) or pAPR1 (1 μg) as described in Example 15. The transfected RAW 264.7 cells were treated with either ethanol (EtOH) (0.1% v/v), 20(S)-hydroxycholesterol (20(S) OH-chol) (10 μM), 9-cis retinoic acid (9-cis RA) (10 μM) or both 20(S) OH-chol and 9-cis RA (20 μM total) for 24 hours. The luciferase activity was measured and reported as relative light units as described in Example 15.

Results: The results of this study are shown in FIG. 12. Control cells transfected with pGL3-Basic showed no luciferase activity (data not shown). Cells transfected with pAPR1 produced a 19-fold increase in luciferase reporter activity in the presence of 20 OH-chol, a 16-fold increase in luciferase activity in the presence of 9-cis RA, and a 280-fold increase in luciferase activity in the presence of both ligands compared with EtOH control. These results indicate that both the sterol and retinoid elicit a strong transcription response from the ABC1 5' flanking sequence in pAPR1. Further, there is an apparent synergistic effect of the two classes of compounds, as can be seen by the dramatic increase in luciferase activity found in cells treated with both ligands. It is known that LXRα and RXRα receptors form active heterodimers. Thus, the ligand-induced activation of both nuclear receptors simultaneously could produce the observed synergistic increase in transcription.

These data demonstrate that hydroxy sterols, such as 20(S) hydroxycholesterol, and retinoids, such as 9-cis retinoic acid, activate the ABC1 promoter, indicating that these and related compounds can be useful in the development of therapeutic compounds to increase ABC1 expression in macrophage cells to rid peripheral sites of excess cholesterol. Additionally, the present ABC1 promoter/reporter gene screening assay can be used to screen other compounds that increase ABC1 expression to identify further therapeutic compounds.

EXAMPLE 18

This example demonstrates the further characterization of the ABC1 promoter region, including the identification of an LXR response element.

To determine which portion of the 5' flanking region of ABC1 retains transcriptional activity in response to nuclear ligands, various plasmids containing a different portion of the 5' flanking region and a luciferase reporter gene were transfected into RAW 264.7 cells treated with at least one ligand for the nuclear receptors. Using this system, a sterol response element corresponding to nucleotides 1480-1510 of SEQ ID NO: 3 was identified. The sterol response element contains a direct repeat-4 element TGACCGatagTAACCT (SEQ ID NO: 61). Confirmation of the sterol response element was obtained using site-directed mutagenesis and band-shift assay techniques.

Construction of Reporter Constructs: Reporter construct pAPR1 and control reporter construct pGL3-Basic were obtained as described in Example 15. Reporter constructs containing either nucleotides 1-1532, 1080-1643, 1181-1643, 1292-1643, or 1394-1643 of SEQ ID NO: 3 were also constructed. A reporter construct containing nucleotides 1080-1643 of SEQ ID NO: 3 (GL-6a) was constructed as described in Example 15. A reporter construct containing nucleotides 1-1532 of SEQ ID NO: 3 was constructed by digestion of pAPR1 with Spe I and Nhe I, and re-ligation of the gel-purified vector fragment. A reporter construct containing nucleotides 1181 to 1643 was constructed by firstly digesting GL-6a with Sty I, blunting the cohesive ends with Klenow enzyme, digesting the resultant vector with Sac I, and isolating the 462 base pair blunt-Sac I cohesive end fragment. This was cloned into a vector obtained by digestion of GL-6a with Acc65 I, blunting of the cohesive ends with Klenow enzyme, digestion with Sac I and gel isolation of the vector fragment. A reporter construct containing nucleotides 1292-1643 was constructed by consecutive digestion of GL-6a with Acc65 I, blunting the ends with Klenow enzyme, digestion with Sac II, blunting the ends with T4 polymerase, and re-ligation of the gel-isolated vector fragment. A reporter construct containing nucleotides 1394-1643 was constructed by digestion of GL-6a with Acc65 I, blunting the ends with Klenow enzyme, subsequent digestion with Apa I, end-blunting with T4 polymerase and re-ligation of the gel-isolated vector fragment.

Transfection of Reporter Constructs: The RAW 264.7 cells were maintained in culture and transfected with either pGL3-Basic (1 μg), pAPR1 (1 μg), or one of the other reporter constructs according to the method described in Example 15. The transfected RAW 264.7 cells were treated with either ethanol (EtOH) (0.1% v/v), 20(S)-hydroxycholesterol (20(S) OH-chol) (10 μM), 22(R)-hydroxycholesterol (22(R) OH-chol) (10 μM), 9-cis retinoic acid (9-cis RA) (10 μM), or both 20(S) OH-chol and 9-cis RA (20 μM total) for 24 hours. The luciferase activity was measured and reported as relative light units as described in Example 15.

Site-Directed Mutagenesis: The sterol response element corresponding to nucleotides 1480-1510 of SEQ ID NO: 3 was mutated in the 1080-1643 sequence described above using site-directed mutagenesis. Specifically, the response element containing a direct repeat-4 element TGACCGatagTAACCT (SEQ ID NO: 61) was mutated to CTGCACatagTAACCT (SEQ ID NO: 62) using the GeneEditor system (Promega, Madison, Wisc.) according to the manufacturer's protocol.

Gel-Shift Assays: Nuclear extract was prepared from RAW 264.7 cells by the method of Ohlsson et al., *Cell,* 45:35-44 (1986). $^{32}$P-labeled oligonucleotides (5 ng) corresponding to the LXR response element (TCGAGTGACCGATAGTAACCTCTCGA; SEQ ID NO: 56) and its mutated counterpart (TCGAGCTGCACATAGTAACCTCTCGA; SEQ ID NO: 57) were individually incubated with 5 μg of nuclear protein for 30 minutes at room temperature in 20 mM HEPES, pH 7.9, 60 mM KCL, 1 mM $MgCl_2$, 1 mM DTT, 66.6 μg/ml poly(dIdC), and 10% glycerol in the presence or absence of 1 μg antiserum to LXRα and LXRβ (Santa Cruz Biotechnology, Cat. No. SC-1591, Santa Cruz, Calif.) or antiserum to RXR (Santa Cruz Biotechnology, Cat. No. SC-774, Santa Cruz, Calif.). The protein-DNA complexes were applied to a 4% non-denaturing polyacrylamide gel for 1.5 hours at 150V in 0.5×TBE buffer. The protein-DNA complexes were detected by autoradiography of the dried gel.

Results: Transfection with the individual reporter constructs containing the 5' flanking region corresponding to nucleotides 1-1643 (i.e., pAPR1), 1-1532, 1080-1643, 1181-1643, 1292-1643, or 1394-1643 of SEQ ID NO: 3 each produced the same results. All of the individual constructs produced a 3 to 4-fold increase in luciferase reporter activity in the presence of 20 (S) OH-chol or 22 (R) OH-chol compared with EtOH control. Also, all of the individual constructs produced an 8 to 10-fold increase luciferase reporter activity in the presence of 9-cis RA. In addition, transfection with any of the constructs produced a 25 to 50-fold increase in luciferase activity in the presence of oxysterol ligand (either (20 (S) OH-chol or 22(R) OH-chol)) and retinoid ligand (9-cis RA) together compared with EtOH control, indicating a synergistic interaction. Each of the described constructs demonstrated comparable levels of luciferase activity in response to the ligands tested, indicating that even the shorter 5' flanking sequences contained transcriptional regulatory sequences for sterols and retinoids. Specifically, these results demonstrated that the transcriptional regulatory sequences for sterols and retinoids are located in the 5' flanking region corresponding to nucleotides 1394-1532 of SEQ ID NO: 3.

These results were confirmed by luciferase assays using a reporter construct containing the wild-type sequence corresponding to nucleotides 1080-1643 of SEQ ID NO: 3 and a reporter construct containing a mutated sequence corresponding to nucleotides 1080-1643 of SEQ ID NO: 3, wherein the sterol response element found at nucleotides 1480-1500 was mutated as described above. Transfection with the wild-type sequence produced a transcritional response, as measured by an increase in luciferase activity, in the presence of either 20 (S) OH-chol or 9-cis RA alone and produced a synergistic response in the presence of both ligands together. In contrast, transfection with the mutated sequence did not produce a transcriptional response in the presence of 20 (S) OH-chol or 22 (R) OH-chol. Transfection of the mutated sequence preserved a reduced response to 9-cis RA, producing a 4 to 5-fold increase in transcriptional activity, rather than the 8 to 10-fold increase observed with the wild-type sequence. Transfection of the mutated sequence also abolished the synergistic transcriptional response seen in the presence of 20 (S) OH-chol and 9-cis RA together. These results were further confirmed by gel-shift assays using the sterol consensus sequence (nucleotides 1480-1510) and its mutated counterpart. The gel-shift assays showed that while nuclear binding proteins isolated from RAW 264.7 cells bound to the sterol consensus sequence, nuclear proteins did not bind to the mutated sequence. Furthermore, incubation of nuclear proteins with the wild-type sterol consensus sequence in the presence of LXR antiserum resulted in the formation of supershifted complexes (i.e. antibody-protein-DNA complexes), identifying the sequence as a sterol response element that binds nuclear receptor LXR. In contrast, incubation of nuclear proteins with the wild-type sterol response element in the presence of RXR antiserum did not result in the formation of supershifted complexes, indicating that RXR does not bind to this sequence. These results show that the mutation which destroys nuclear protein binding to the consensus sequence also abolishes the transcriptional response to LXR ligands and diminishes the response to RXR ligands. Furthermore, the nuclear binding studies performed in the presence of LXR or RXR antiserum confirmed that the consensus sequence found at nucleotides 1480-1510 is an LXR response element. This element also mediates a partial response to 9-cis RA.

All of the references cited herein, including patents and publications, are hereby incorporated in their entireties by reference. While the invention has been described with an emphasis upon preferred aspects of the invention, it will be readily apparent to those of ordinary skill in the art that variations of the preferred embodiments can be used and that it is intended that the invention can be practiced otherwise than is specifically described herein. Accordingly, the present invention includes all modifications encompassed within the spirit and scope of the invention as defined by the following claims.

---

We claim:

1. A method for screening a test compound for ABC1 expression modulating activity comprising the steps of:

operatively linking a reporter cDNA with an expression modulating portion of the mammalian ABC1 gene to produce a recombinant reporter construct, wherein the expression modulating portion of the mammalian ABC1 gene comprises SEQ ID NO: 3;

transfecting the recombinant reporter construct into a population of host cells;

assaying the level of reporter gene expression in a sample of the host cells;

contacting the host cells with the test compound being screened;

assaying the level of reporter gene expression in a sample of the host cells after contact with the test compound; and comparing the relative change in the level of reporter gene expression caused by exposure to the test compound, thereby determining the ABC1 expression modulating activity.

2. The method of claim 1, wherein the reporter cDNA is selected from the group consisting of luciferase, β-galactosidase, chloramphenicol acetyl transferase, and green fluorescent protein cDNA.

3. The method of claim 1, wherein the host cell is a mammalian cell.

4. The method of claim 2, wherein the recombinant reporter construct comprises SEQ ID NO: 3 and a luciferase reporter gene in a pGL3 vector.

5. A method for screening a test compound for ABC1 expression modulating activity comprising the steps of:

operatively linking a reporter cDNA with an expression modulating portion of the mammalian ABC 1 gene to produce a recombinant reporter construct, wherein the expression modulating portion of the mammalian ABC1 gene comprises a polynucleotide comprising nucleotides 1-1532, 1080-1643, 1181-1643, 1292-1643, 1394-1643, or 1394-1532 of SEQ ID NO: 3;

transfecting the recombinant reporter construct into a population of host cells;

assaying the level of reporter gene expression in a sample of the host cells;

contacting the host cells with the test compound being screened;

assaying the level of reporter gene expression in a sample of the host cells after contact with the test compound; and comparing the relative change in the level of reporter gene expression caused by exposure to the test compound, thereby determining the ABC1 expression modulating activity.

6. The method of claim 5, wherein the reporter cDNA is selected from the group consisting of luciferase, β-galactosidase, chloramphenicol acetyl transferase, and green fluorescent protein cDNA.

7. The method of claim 5, wherein the host cell is a mammalian cell.

* * * * *

SEQUENCE LISTING

```
<160> NUMBER OF SEQ ID NOS: 57

<210> SEQ ID NO 1
<211> LENGTH: 10442
<212> TYPE: DNA
<213> ORGANISM: Homo sapiens
<220> FEATURE:
<221> NAME/KEY: unsure
<222> LOCATION: (1)..(10442)
<223> OTHER INFORMATION: All n's are unknown.

<400> SEQUENCE: 1

ggccgggacc cgcagagccg agccgaccct tctctcccgg gctgcggcag ggcagggcgg     60

ggagctccgc gcaccaacag agccggttct cagggcgctt tgctccttgt tttttccccg    120

gttctgtttt ctccccttct ccggaaggct tgtcaagggg taggagaaag agacgcaaac    180

acaaaagtgg aaaacagtta atgaccagcc acgggcgtcc ctgctgtgag ctctggccgc    240

tgccttccag ggctcccgag ccacacgctg ggcgtgctgg ctgagggaac atggcttgtt    300

ggcctcagct gaggttgctg ctgtggaaga acctcacttt cagaagaaga caaacatgtc    360

agctgttact ggaagtggcc tggcctctat ttatcttcct gatcctgatc tctgttcggc    420

tgagctaccc accctatgaa caacatgaat gccattttcc aaataaagcc atgccctctg    480

caggaacact tccttgggtt caggggatta tctgtaatgc caacaacccc tgtttccgtt    540

acccgactcc tggggaggct cccggagttg ttggaaactt taacaaatcc attgtggctc    600

gcctgttctc agatgctcgg aggcttcttt tatacagcca gaaagacacc agcatgaagg    660

acatgcgcaa agttctgaga acattacagc agatcaagaa atccagctca aacttgaagc    720

ttcaagattt cctggtggac aatgaaacct tctctgggtt cctatatcac aacctctctc    780

tcccaaagtc tactgtggac aagatgctga gggctgatgt cattctccac aaggtatttt    840

tgcaaggcta ccagttacat ttgacaagtc tgtgcaatgg atcaaaatca gaagagatga    900

ttcaacttgg tgaccaagaa gtttctgagc tttgtggcct accaaaggag aaactggctg    960

cagcagagcg agtacttcgt tccaacatgg acatcctgaa gccaatcctg agaacactaa   1020

actctacatc tcccttcccg agcaaggagc tggctgaagc cacaaaaaca ttgctgcata   1080

gtcttgggac tctggcccag gagctgttca gcatgagaag ctggagtgac atgcgacagg   1140

aggtgatgtt tctgaccaat gtgaacagct ccagctcctc cacccaaatc taccaggctg   1200

tgtctcgtat tgtctgcggg catcccgagg gagggggct gaagatcaag tctctcaact   1260

ggtatgagga caacaactac aaagccctct ttggaggcaa tggcactgag gaagatgctg   1320

aaaccttcta tgacaactct acaactcctt actgcaatga tttgatgaag aatttggagt   1380

ctagtcctct ttcccgcatt atctggaaag ctctgaagcc gctgctcgtt gggaagatcc   1440

tgtatacacc tgacactcca gccacaaggc aggtcatggc tgaggtgaac aagaccttcc   1500

aggaactggc tgtgttccat gatctggaag gcatgtggga ggaactcagc cccaagatct   1560

ggaccttcat ggagaacagc caagaaatgg accttgtccg gatgctgttg gacagcaggg   1620
```

-continued

```
acaatgacca cttttgggaa cagcagttgg atggcttaga ttggacagcc caagacatcg   1680
tggcgttttt ggccaagcac ccagaggatg tccagtccag taatggttct gtgtacacct   1740
ggagagaagc tttcaacgag actaaccagg caatccggac catatctcgc ttcatggagt   1800
gtgtcaacct gaacaagcta gaacccatag caacagaagt ctggctcatc aacaagtcca   1860
tggagctgct ggatgagagg aagttctggg ctggtattgt gttcactgga attactccag   1920
gcagcattga gctgccccat catgtcaagt acaagatccg aatggacatt gacaatgtgg   1980
agaggacaaa taaaatcaag gatgggtact gggaccctgg tcctcgagct gaccccttg    2040
aggacatgcg gtacgtctgg gggggcttcg cctacttgca ggatgtggtg gagcaggcaa   2100
tcatcagggt gctgacgggc accgagaaga aaactggtgt ctatatgcaa cagatgccct   2160
atccctgtta cgttgatgac atctttctgc gggtgatgag ccggtcaatg cccctcttca   2220
tgacgctggc ctggatttac tcagtggctg tgatcatcaa gggcatcgtg tatgagaagg   2280
aggcacggct gaaagagacc atgcggatca tgggcctgga caacagcata ctctggttta   2340
gctggttcat tagtagcctc attcctcttc ttgtgagcgc tggcctgcta gtggtcatcc   2400
tgaagttagg aaacctgctg ccctacagtg atcccagcgt ggtgtttgtc ttcctgtccg   2460
tgtttgctgt ggtgacaatc ctgcagtgct tcctgattag cacactcttc tccagagcca   2520
acctggcagc agcctgtggg ggcatcatct acttcacgct gtacctgccc tacgtcctgt   2580
gtgtggcatg gcaggactac gtgggcttca cactcaagat cttcgctagc ctgctgtctc   2640
ctgtggcttt tgggtttggc tgtgagtact ttgccctttt tgaggagcag ggcattggag   2700
tgcagtggga caacctgttt gagagtcctg tggaggaaga tggcttcaat ctcaccactt   2760
cgatctccat gatgctgttt gacaccttcc tctatggggt gatgacctgg tacattgagg   2820
ctgtctttcc aggccagtac ggaattccca ggccctggta ttttccttgc accaagtcct   2880
actggtttgg cgaggaaagt gatgagaaga gccaccctgg ttccaaccag aagagaatgt   2940
cagaaatctg catggaggag gaacccaccc acttgaagct gggcgtgtcc attcagaacc   3000
tggtaaaagt ctaccgagat gggatgaagg tggctgtcga tggcctggca ctgaattttt   3060
atgagggcca gatcacctcc ttcctgggcc acaatggagc ggggaagacg accaccatgt   3120
caatcctgac cgggttgttc cccccgacct cgggcaccgc ctacatcctg ggaaaagaca   3180
ttcgctctga gatgagcacc atccggcaga acctgggggt ctgtccccag cataacgtgc   3240
tgtttgacat gctgactgtc gaagaacaca tctggttcta tgcccgcttg aaagggctct   3300
ctgagaagca cgtgaaggcg gagatggagc agatggccct ggatgttggt ttgccatcaa   3360
gcaagctgaa aagcaaaaca agccagctgt caggtggaat gcagagaaag ctatctgtgg   3420
ccttggcctt tgtcgggggga tctaaggttg tcattctgga tgaacccaca gctggtgtgg   3480
acccttactc ccgcagggga atatgggagc tgctgctgaa ataccgacaa ggccgcacca   3540
ttattctctc tacacaccac atggatgaag cggacgtcct gggggacagg attgccatca   3600
tctcccatgg gaagctgtgc tgtgtgggct cctccctgtt tctgaagaac cagctgggaa   3660
caggctacta cctgaccttg gtcaagaaag atgtggaatc ctccctcagt tcctgcagaa   3720
acagtagtag cactgtgtca tacctgaaaa aggaggacag tgtttctcag agcagttctg   3780
atgctggcct gggcagcgac catgagagtg acacgctgac catcgatgtc tctgctatct   3840
ccaacctcat caggaagcat gtgtctgaag cccggctggt ggaagacata gggcatgagc   3900
tgacctatgt gctgccatat gaagctgcta aggagggagc ctttgtggaa ctctttcatg   3960
agattgatga ccggctctca gacctgggca tttctagtta tggcatctca gagacgaccc   4020
```

-continued

```
tggaagaaat attcctcaag gtggccgaag agagtggggt ggatgctgag acctcagatg   4080
gtaccttgcc agcaagacga aacaggcggg ccttcgggga caagcagagc tgtcttcgcc   4140
cgttcactga agatgatgct gctgatccaa atgattctga catagaccca gaatccagag   4200
agacagactt gctcagtggg atggatggca aagggtccta ccaggtgaaa ggctggaaac   4260
ttacacagca acagtttgtg gcccttttgt ggaagagact gctaattgcc agacggagtc   4320
ggaaaggatt ttttgctcag attgtcttgc cagctgtgtt tgtctgcatt gcccttgtgt   4380
tcagcctgat cgtgccaccc tttggcaagt accccagcct ggaacttcag ccctggatgt   4440
acaacgaaca gtacacattt gtcagcaatg atgctcctga ggacacggga accctggaac   4500
tcttaaacgc cctcaccaaa gaccctggct tcgggacccg ctgtatggaa ggaaacccaa   4560
tcccagacac gccctgccag gcaggggagg aagagtggac cactgcccca gttccccaga   4620
ccatcatgga cctcttccag aatgggaact ggacaatgca gaacccttca cctgcatgcc   4680
agtgtagcag cgacaaaatc aagaagatgc tgcctgtgtg tcccccaggg gcaggggggc   4740
tgcctcctcc acaaagaaaa caaaacactg cagatatcct tcaggacctg acaggaagaa   4800
acatttcgga ttatctggtg aagacgtatg tgcagatcat agccaaaagc ttaaagaaca   4860
agatctgggt gaatgagttt aggtatggcg gcttttccct gggtgtcagt aatactcaag   4920
cacttcctcc gagtcaagaa gttaatgatg ccatcaaaca aatgaagaaa cacctaaagc   4980
tggccaagga cagttctgca gatcgatttc tcaacagctt gggaagattt atgacaggac   5040
tggacaccag aaataatgtc aaggtgtggt tcaataacaa gggctggcat gcaatcagct   5100
ctttcctgaa tgtcatcaac aatgccattc tccgggccaa cctgcaaaag ggagagaacc   5160
ctagccatta tggaattact gctttcaatc atcccctgaa tctcaccaag cagcagctct   5220
cagaggtggc tctgatgacc acatcagtgg atgtccttgt gtccatctgt gtcatctttg   5280
caatgtcctt cgtcccagcc agctttgtcg tattcctgat ccaggagcgg gtcagcaaag   5340
caaaacacct gcagttcatc agtggagtga agcctgtcat ctactggctc tctaattttg   5400
tctgggatat gtgcaattac gttgtccctg ccacactggt cattatcatc ttcatctgct   5460
tccagcagaa gtcctatgtg tcctccacca atctgcctgt gctagccctt ctacttttgc   5520
tgtatgggtg gtcaatcaca cctctcatgt acccagcctc ctttgtgttc aagatcccca   5580
gcacagccta tgtggtgctc accagcgtga acctcttcat tggcattaat ggcagcgtgg   5640
ccacctttgt gctggagctg ttcaccgaca ataagctgaa taatatcaat gatatcctga   5700
agtccgtgtt cttgatcttc ccacattttt gcctgggacg agggctcatc gacatggtga   5760
aaaaccaggc aatggctgat gccctggaaa ggtttgggga gaatcgcttt gtgtcaccat   5820
tatcttggga cttggtggga cgaaacctct tcgccatggc cgtggaaggg gtggtgttct   5880
tcctcattac tgttctgatc cagtacagat tcttcatcag gcccagacct gtaaatgcaa   5940
agctatctcc tctgaatgat gaagatgaag atgtgaggcg ggaaagacag agaattcttg   6000
atggtggagg ccagaatgac atcttagaaa tcaaggagtt gacgaagata tatagaagga   6060
agcggaagcc tgctgttgac aggatttgcg tgggcattcc tcctggtgag tgctttgggc   6120
tcctgggagt taatggggct ggaaaatcat caactttcaa gatgttaaca ggagatacca   6180
ctgttaccag aggagatgct ttccttaaca aaaatagtat cttatcaaac atccatgaag   6240
tacatcagaa catgggctac tgccctcagt ttgatgccat cacagagctg ttgactggga   6300
gagaacacgt ggagttcttt gcccttttga gaggagtccc agagaaagaa gttggcaagg   6360
```

-continued

```
ttggtgagtg ggcgattcgg aaactgggcc tcgtgaagta tggagaaaaa tatgctggta   6420
actatagtgg aggcaacaaa cgcaagctct ctacagccat ggctttgatc ggcgggcctc   6480
ctgtggtgtt tctggatgaa cccaccacag gcatggatcc caaagcccgg cggttcttgt   6540
ggaattgtgc cctaagtgtt gtcaaggagg ggagatcagt agtgcttaca tctcatagta   6600
tggaagaatg tgaagctctt tgcactagga tggcaatcat ggtcaatgga aggttcaggt   6660
gccttggcag tgtccagcat ctaaaaaata ggtttggaga tggttataca atagttgtac   6720
gaatagcagg gtccaacccg gacctgaagc ctgtccagga tttctttgga cttgcatttc   6780
ctggaagtgt tctaaaagag aaacaccgga acatgctaca ataccagctt ccatcttcat   6840
tatcttctct ggccaggata ttcagcatcc tctcccagag caaaaagcga ctccacatag   6900
aagactactc tgtttctcag acaacacttg accaagtatt tgtgaacttt gccaaggacc   6960
aaagtgatga tgaccactta aaagacctct cattacacaa aaaccagaca gtagtggacg   7020
ttgcagttct cacatctttt ctacaggatg agaaagtgaa agaaagctat gtatgaagaa   7080
tcctgttcat acggggtggc tgaaagtaaa gaggaactag actttccttt gcaccatgtg   7140
aagtgttgtg gagaaaagag ccagaagttg atgtgggaag aagtaaactg gatactgtac   7200
tgatactatt caatgcaatg caattcaatg caatgaaaac aaaattccat tacaggggca   7260
gtgcctttgt agcctatgtc ttgtatggct ctcaagtgaa agacttgaat ttagtttttt   7320
acctatacct atgtgaaact ctattatgga acccaatgga catatgggtt tgaactcaca   7380
cttttttttt tttttgttc ctgtgtattc tcattggggt tgcaacaata attcatcaag    7440
taatcatggc cagcgattat tgatcaaaat caaaaggtaa tgcacatcct cattcactaa   7500
gccatgccat gcccaggaga ctggtttccc ggtgacacat ccattgctgg caatgagtgt   7560
gccagagtta ttagtgccaa gtttttcaga aagtttgaag caccatggtg tgtcatgctc   7620
acttttgtga aagctgctct gctcagagtc tatcaacatt gaatatcagt tgacagaatg   7680
gtgccatgcg tggctaacat cctgctttga ttccctctga taagctgttc tggtggcagt   7740
aacatgcaac aaaaatgtgg gtgtctctag gcacgggaaa cttggttcca ttgttatatt   7800
gtcctatgct tcgagccatg ggtctacagg gtcatcctta tgagactctt aaatatactt   7860
agatcctggt aagaggcaaa gaatcaacag ccaaactgct ggggctgcaa gctgctgaag   7920
ccagggcatg ggattaaaga gattgtgcgt tcaaacctag ggaagcctgt gcccatttgt   7980
cctgactgtc tgctaacatg gtacactgca tctcaagatg tttatctgac acaagtgtat   8040
tatttctggc tttttgaatt aatctagaaa atgaaaagat ggagttgtat tttgacaaaa   8100
atgtttgtac tttttaatgt tatttggaat tttaagttct atcagtgact tctgaatcct   8160
tagaatggcc tctttgtaga accctgtggt atagaggagt atggccactg ccccactatt   8220
tttattttct tatgtaagtt tgcatatcag tcatgactag tgcctagaaa gcaatgtgat   8280
ggtcaggatc tcatgacatt atatttgagt ttctttcaga tcatttagga tactcttaat   8340
ctcacttcat caatcaaata ttttttgagt gtatgctgta gctgaaagag tatgtacgta   8400
cgtataagac tagagagata ttaagtctca gtacacttcc tgtgccatgt tattcagctc   8460
actggtttac aaatataggt tgtcttgtgg ttgtaggagc ccactgtaac aatattgggc   8520
agcctttttt tttttttttt aattgcaaca atgcaaaagc caagaaagta taagggtcac   8580
aagtttaaac aatgaattct tcaacaggga aaacagctag cttgaaaact tgctgaaaaa   8640
cacaacttgt gtttatggca tttagtacct tcaaataatt ggctttgcag atattggata   8700
ccccattaaa tctgacagtc tcaaattttt catctcttca atcactagtc aagaaaaata   8760
```

-continued

```
taaaaacaac aaatacttcc atatggagca tttttcagag ttttctaacc cagtcttatt   8820
tttctagtca gtaaacattt gtaaaaatac tgtttcacta atacttactg ttaactgtct   8880
tgagagaaaa gaaaaatatg agagaactat tgtttgggga agttcaagtg atctttcaat   8940
atcattacta acttcttcca ctttttccaa aatttgaata ttaacgctaa aggtgtaaga   9000
cttcagattt caaattaatc tttctatatt ttttaaattt acagaatatt atataaccca   9060
ctgctgaaaa agaaaaaaat gattgtttta gaagttaaag tcaatattga ttttaaatat   9120
aagtaatgaa ggcatatttc caataactag tgatatggca tcgttgcaat ttacagtatc   9180
ttcaaaaata cagaatttat agaataattt ctcctcattt aatatttttc aaaatcaaag   9240
ttatggtttc ctcattttac taaaatcgta ttctaattct tcattatagt aaatctatga   9300
gcaactcctt acttcggttc ctctgatttc aaggccatat tttaaaaaat caaaaggcac   9360
tgtgaactat tttgaagaaa acacgacatt ttaatacaga ttgaaaggac ctcttctgaa   9420
gctagaaaca atctatagtt atacatcttc attaatactg tgttaccttt taaaatagta   9480
atttttttaca ttttcctgtg taaacctaat tgtggtagaa atttttacca actctatact   9540
caatcaagca aaatttctgt atattccctg tggaatgtac ctatgtgagt ttcagaaatt   9600
ctcaaaatac gtgttcaaaa atttctgctt ttgcatcttt gggacacctc agaaaactta   9660
ttaacaactg tgaatatgag aaatacagaa gaaaataata agccctctat acataaatgc   9720
ccagcacaat tcattgttaa aaaacaacca aacctcacac tactgtattt cattatctgt   9780
actgaaagca aatgctttgt gactattaaa tgttgcacat cattcattca ctgtatagta   9840
atcattgact aaagccattt gctgtgtttt cttcttgtgg ntgnatatat caggtaaaat   9900
attttccaaa gagccatgtg tcatgtaata ctgaaccctt tgatattgag acattaattt   9960
ggacccttgg tattatctac tagaataatg taatactgna gaaatattgc tctaattctt  10020
tcaaaatggt gcatccccct taaaangttc tatttccata aggatttagc ttgcttatcc  10080
cttcttatac cctaagatga agctgttttt gtgctctttg ttcatcattg gccctcattc  10140
caagcacttt acgctgtctg taatgggatc tatttttgca ctggaatatc tgagaattgc  10200
aaaactagac aaaagtttca caacagattt ctaagttaaa tcattttcat taaaaggaaa  10260
aaagaaaaaa aattttgtat gtcaataact ttatatgaag tattaaaatg catatttcta  10320
tgttgtaata taatgagtca caaaataaag ctgtgacagt tctgttaaaa aaaaaaaaaa  10380
aaaaaaaaaa aaaaaaaaaa aaaaaaaaaa aaaaaaaaaa aaaaaaaaaa aaaaaaaaaa  10440
aa                                                                 10442
```

<210> SEQ ID NO 2
<211> LENGTH: 2261
<212> TYPE: PRT
<213> ORGANISM: Homo sapiens

<400> SEQUENCE: 2

```
Met Ala Cys Trp Pro Gln Leu Arg Leu Leu Leu Trp Lys Asn Leu Thr
  1               5                  10                  15

Phe Arg Arg Arg Gln Thr Cys Gln Leu Leu Leu Glu Val Ala Trp Pro
             20                  25                  30

Leu Phe Ile Phe Leu Ile Leu Ile Ser Val Arg Leu Ser Tyr Pro Pro
         35                  40                  45

Tyr Glu Gln His Glu Cys His Phe Pro Asn Lys Ala Met Pro Ser Ala
     50                  55                  60
```

-continued

```
Gly Thr Leu Pro Trp Val Gln Gly Ile Ile Cys Asn Ala Asn Asn Pro
 65                 70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Ser Asn Leu Lys Leu
    130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
        195                 200                 205

Gln Glu Val Ser Glu Leu Cys Gly Leu Pro Lys Glu Lys Leu Ala Ala
    210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
            260                 265                 270

Phe Ser Met Arg Ser Trp Ser Asp Met Arg Gln Glu Val Met Phe Leu
        275                 280                 285

Thr Asn Val Asn Ser Ser Ser Ser Ser Thr Gln Ile Tyr Gln Ala Val
    290                 295                 300

Ser Arg Ile Val Cys Gly His Pro Glu Gly Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
        435                 440                 445

Trp Glu Gln Gln Leu Asp Gly Leu Asp Trp Thr Ala Gln Asp Ile Val
    450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
```

-continued

```
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
        515                 520                 525

Glu Arg Lys Phe Trp Ala Gly Ile Val Phe Thr Gly Ile Thr Pro Gly
    530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
        595                 600                 605

Thr Gly Thr Glu Lys Lys Thr Gly Val Tyr Met Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Ile Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ser Asp Glu Lys Ser His Pro Gly Ser Asn Gln
865                 870                 875                 880

Lys Arg Met Ser Glu Ile Cys Met Glu Glu Glu Pro Thr His Leu Lys
                885                 890                 895

Leu Gly Val Ser Ile Gln Asn Leu Val Lys Val Tyr Arg Asp Gly Met
            900                 905                 910
```

-continued

```
Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                 1000                1005

Lys Ala Glu Met Glu Gln Met Ala Leu Asp Val Gly Leu Pro Ser Ser
    1010                1015                1020

Lys Leu Lys Ser Lys Thr Ser Gln Leu Ser Gly Gly Met Gln Arg Lys
1025                1030                1035                1040

Leu Ser Val Ala Leu Ala Phe Val Gly Gly Ser Lys Val Val Ile Leu
                1045                1050                1055

Asp Glu Pro Thr Ala Gly Val Asp Pro Tyr Ser Arg Arg Gly Ile Trp
            1060                1065                1070

Glu Leu Leu Leu Lys Tyr Arg Gln Gly Arg Thr Ile Ile Leu Ser Thr
        1075                1080                1085

His His Met Asp Glu Ala Asp Val Leu Gly Asp Arg Ile Ala Ile Ile
    1090                1095                1100

Ser His Gly Lys Leu Cys Cys Val Gly Ser Ser Leu Phe Leu Lys Asn
1105                1110                1115                1120

Gln Leu Gly Thr Gly Tyr Tyr Leu Thr Leu Val Lys Lys Asp Val Glu
                1125                1130                1135

Ser Ser Leu Ser Ser Cys Arg Asn Ser Ser Ser Thr Val Ser Tyr Leu
            1140                1145                1150

Lys Lys Glu Asp Ser Val Ser Gln Ser Ser Ser Asp Ala Gly Leu Gly
        1155                1160                1165

Ser Asp His Glu Ser Asp Thr Leu Thr Ile Asp Val Ser Ala Ile Ser
    1170                1175                1180

Asn Leu Ile Arg Lys His Val Ser Glu Ala Arg Leu Val Glu Asp Ile
1185                1190                1195                1200

Gly His Glu Leu Thr Tyr Val Leu Pro Tyr Glu Ala Ala Lys Glu Gly
                1205                1210                1215

Ala Phe Val Glu Leu Phe His Glu Ile Asp Asp Arg Leu Ser Asp Leu
            1220                1225                1230

Gly Ile Ser Ser Tyr Gly Ile Ser Glu Thr Thr Leu Glu Glu Ile Phe
        1235                1240                1245

Leu Lys Val Ala Glu Glu Ser Gly Val Asp Ala Glu Thr Ser Asp Gly
    1250                1255                1260

Thr Leu Pro Ala Arg Arg Asn Arg Arg Ala Phe Gly Asp Lys Gln Ser
1265                1270                1275                1280

Cys Leu Arg Pro Phe Thr Glu Asp Asp Ala Ala Asp Pro Asn Asp Ser
                1285                1290                1295

Asp Ile Asp Pro Glu Ser Arg Glu Thr Asp Leu Leu Ser Gly Met Asp
            1300                1305                1310

Gly Lys Gly Ser Tyr Gln Val Lys Gly Trp Lys Leu Thr Gln Gln Gln
        1315                1320                1325
```

-continued

```
Phe Val Ala Leu Leu Trp Lys Arg Leu Leu Ile Ala Arg Arg Ser Arg
    1330                1335                1340

Lys Gly Phe Phe Ala Gln Ile Val Leu Pro Ala Val Phe Val Cys Ile
1345                1350                1355                1360

Ala Leu Val Phe Ser Leu Ile Val Pro Pro Phe Gly Lys Tyr Pro Ser
                1365                1370                1375

Leu Glu Leu Gln Pro Trp Met Tyr Asn Glu Gln Tyr Thr Phe Val Ser
            1380                1385                1390

Asn Asp Ala Pro Glu Asp Thr Gly Thr Leu Glu Leu Leu Asn Ala Leu
        1395                1400                1405

Thr Lys Asp Pro Gly Phe Gly Thr Arg Cys Met Glu Gly Asn Pro Ile
    1410                1415                1420

Pro Asp Thr Pro Cys Gln Ala Gly Glu Glu Glu Trp Thr Thr Ala Pro
1425                1430                1435                1440

Val Pro Gln Thr Ile Met Asp Leu Phe Gln Asn Gly Asn Trp Thr Met
                1445                1450                1455

Gln Asn Pro Ser Pro Ala Cys Gln Cys Ser Ser Asp Lys Ile Lys Lys
            1460                1465                1470

Met Leu Pro Val Cys Pro Pro Gly Ala Gly Gly Leu Pro Pro Pro Gln
        1475                1480                1485

Arg Lys Gln Asn Thr Ala Asp Ile Leu Gln Asp Leu Thr Gly Arg Asn
    1490                1495                1500

Ile Ser Asp Tyr Leu Val Lys Thr Tyr Val Gln Ile Ile Ala Lys Ser
1505                1510                1515                1520

Leu Lys Asn Lys Ile Trp Val Asn Glu Phe Arg Tyr Gly Gly Phe Ser
                1525                1530                1535

Leu Gly Val Ser Asn Thr Gln Ala Leu Pro Pro Ser Gln Glu Val Asn
            1540                1545                1550

Asp Ala Ile Lys Gln Met Lys Lys His Leu Lys Leu Ala Lys Asp Ser
        1555                1560                1565

Ser Ala Asp Arg Phe Leu Asn Ser Leu Gly Arg Phe Met Thr Gly Leu
    1570                1575                1580

Asp Thr Arg Asn Asn Val Lys Val Trp Phe Asn Asn Lys Gly Trp His
1585                1590                1595                1600

Ala Ile Ser Ser Phe Leu Asn Val Ile Asn Asn Ala Ile Leu Arg Ala
                1605                1610                1615

Asn Leu Gln Lys Gly Glu Asn Pro Ser His Tyr Gly Ile Thr Ala Phe
            1620                1625                1630

Asn His Pro Leu Asn Leu Thr Lys Gln Gln Leu Ser Glu Val Ala Leu
        1635                1640                1645

Met Thr Thr Ser Val Asp Val Leu Val Ser Ile Cys Val Ile Phe Ala
    1650                1655                1660

Met Ser Phe Val Pro Ala Ser Phe Val Val Phe Leu Ile Gln Glu Arg
1665                1670                1675                1680

Val Ser Lys Ala Lys His Leu Gln Phe Ile Ser Gly Val Lys Pro Val
                1685                1690                1695

Ile Tyr Trp Leu Ser Asn Phe Val Trp Asp Met Cys Asn Tyr Val Val
            1700                1705                1710

Pro Ala Thr Leu Val Ile Ile Ile Phe Ile Cys Phe Gln Gln Lys Ser
        1715                1720                1725

Tyr Val Ser Ser Thr Asn Leu Pro Val Leu Ala Leu Leu Leu Leu Leu
    1730                1735                1740

Tyr Gly Trp Ser Ile Thr Pro Leu Met Tyr Pro Ala Ser Phe Val Phe
```

-continued

```
1745                1750                1755                1760

Lys Ile Pro Ser Thr Ala Tyr Val Val Leu Thr Ser Val Asn Leu Phe
                1765                1770                1775

Ile Gly Ile Asn Gly Ser Val Ala Thr Phe Val Leu Glu Leu Phe Thr
            1780                1785                1790

Asp Asn Lys Leu Asn Asn Ile Asn Asp Ile Leu Lys Ser Val Phe Leu
        1795                1800                1805

Ile Phe Pro His Phe Cys Leu Gly Arg Gly Leu Ile Asp Met Val Lys
    1810                1815                1820

Asn Gln Ala Met Ala Asp Ala Leu Glu Arg Phe Gly Glu Asn Arg Phe
1825                1830                1835                1840

Val Ser Pro Leu Ser Trp Asp Leu Val Gly Arg Asn Leu Phe Ala Met
                1845                1850                1855

Ala Val Glu Gly Val Val Phe Phe Leu Ile Thr Val Leu Ile Gln Tyr
            1860                1865                1870

Arg Phe Phe Ile Arg Pro Arg Pro Val Asn Ala Lys Leu Ser Pro Leu
        1875                1880                1885

Asn Asp Glu Asp Glu Asp Val Arg Arg Glu Arg Gln Arg Ile Leu Asp
    1890                1895                1900

Gly Gly Gly Gln Asn Asp Ile Leu Glu Ile Lys Glu Leu Thr Lys Ile
1905                1910                1915                1920

Tyr Arg Arg Lys Arg Lys Pro Ala Val Asp Arg Ile Cys Val Gly Ile
                1925                1930                1935

Pro Pro Gly Glu Cys Phe Gly Leu Leu Gly Val Asn Gly Ala Gly Lys
            1940                1945                1950

Ser Ser Thr Phe Lys Met Leu Thr Gly Asp Thr Thr Val Thr Arg Gly
        1955                1960                1965

Asp Ala Phe Leu Asn Lys Asn Ser Ile Leu Ser Asn Ile His Glu Val
    1970                1975                1980

His Gln Asn Met Gly Tyr Cys Pro Gln Phe Asp Ala Ile Thr Glu Leu
1985                1990                1995                2000

Leu Thr Gly Arg Glu His Val Glu Phe Phe Ala Leu Leu Arg Gly Val
                2005                2010                2015

Pro Glu Lys Glu Val Gly Lys Val Gly Glu Trp Ala Ile Arg Lys Leu
            2020                2025                2030

Gly Leu Val Lys Tyr Gly Glu Lys Tyr Ala Gly Asn Tyr Ser Gly Gly
        2035                2040                2045

Asn Lys Arg Lys Leu Ser Thr Ala Met Ala Leu Ile Gly Gly Pro Pro
    2050                2055                2060

Val Val Phe Leu Asp Glu Pro Thr Thr Gly Met Asp Pro Lys Ala Arg
2065                2070                2075                2080

Arg Phe Leu Trp Asn Cys Ala Leu Ser Val Val Lys Glu Gly Arg Ser
                2085                2090                2095

Val Val Leu Thr Ser His Ser Met Glu Glu Cys Glu Ala Leu Cys Thr
            2100                2105                2110

Arg Met Ala Ile Met Val Asn Gly Arg Phe Arg Cys Leu Gly Ser Val
        2115                2120                2125

Gln His Leu Lys Asn Arg Phe Gly Asp Gly Tyr Thr Ile Val Val Arg
    2130                2135                2140

Ile Ala Gly Ser Asn Pro Asp Leu Lys Pro Val Gln Asp Phe Phe Gly
2145                2150                2155                2160

Leu Ala Phe Pro Gly Ser Val Leu Lys Glu Lys His Arg Asn Met Leu
                2165                2170                2175
```

-continued

```
Gln Tyr Gln Leu Pro Ser Ser Leu Ser Ser Leu Ala Arg Ile Phe Ser
            2180                2185                2190

Ile Leu Ser Gln Ser Lys Lys Arg Leu His Ile Glu Asp Tyr Ser Val
        2195                2200                2205

Ser Gln Thr Thr Leu Asp Gln Val Phe Val Asn Phe Ala Lys Asp Gln
    2210                2215                2220

Ser Asp Asp Asp His Leu Lys Asp Leu Ser Leu His Lys Asn Gln Thr
2225                2230                2235                2240

Val Val Asp Val Ala Val Leu Thr Ser Phe Leu Gln Asp Glu Lys Val
                2245                2250                2255

Lys Glu Ser Tyr Val
            2260


<210> SEQ ID NO 3
<211> LENGTH: 1643
<212> TYPE: DNA
<213> ORGANISM: Homo sapiens

<400> SEQUENCE: 3

gaattccttg ctggtggctc cacatgcact tccagggcct gcttggctct tctatgggtc     60

tgtcctgagt gttgatagaa ccactgatgt gagtacctgg gcttgagcgt ggcctggaga    120

tcctgttgac tgtagcatgg agggggcttg tcagctgaat gtctgtatgc aggtggtggg    180

agttctggaa tatgatggag ctggaggtgg gaagagaagt aggcttgggg cagctctctc    240

atgccacctc attctggcca aaactcaggt caaactgtga agagtctaaa tgtgaatctg    300

cccttcaagg tggctacaaa ggtatctttg tcaaggtagg agaccttgtg gcctccacgt    360

gcacttccag ggcctgcttg gcctcttcta cgggtctgtc ctgagtcttc tatgaatctc    420

ccttcagggc agattcatat ttagactctt cacagtttga cctgagtttt ggccagaata    480

aggtgacatt tagtttgttg gcttgatgaa tgacttaaat atttagacat atggtgtgta    540

ggcctgcatt cctactcttg cctttttttt tgcccctcca gtgtttttggg tagttttgct    600

ccccctacag ccaaaggcaa acagataagt tggaggtctg gagtggctac ataattttac    660

acgactgcaa ttctctggct gcacttcaca aatgtataca aactaaatac aagtcctgtg    720

tttttatcac agggaggctg atcaatataa tgaaattaaa agggggctgg tcccatattg    780

ttctgtgttt ttgtttgttt gtttcttttt ttgtttttgt ggcctccttc ctctcaattt    840

atgaagagaa gcagtaagat gttcctctcg ggtcctctga gggacctggg gagctcaggc    900

tgggaatctc caaggcagta ggtcgcctat caaaaatcaa agtccaggtt tgtgggggga    960

aaacaaaagc agcccattac ccagaggact gtccgccttc ccctcacccc agcctaggcc   1020

tttgaaagga aacaaaagac aagacaaaat gattggcgtc ctgagggaga ttcagcctag   1080

agctctctct cccccaatcc ctccctccgg ctgaggaaac taacaaagga aaaaaaaatt   1140

gcggaaagca ggatttagag gaagcaaatt ccactggtgc ccttggctgc cgggaacgtg   1200

gactagagag tctgcggcgc agccccgagc ccagcgcttc ccgcgcgtct taggccggcg   1260

ggcccgggcg ggggaagggg acgcagaccg cggaccctaa gacacctgct gtaccctcca   1320

cccccacccc acccacctcc ccccaactcc ctagatgtgt cgtgggcggc tgaacgtcgc   1380

ccgtttaagg ggcgggcccc ggctccacgt gctttctgct gagtgactga actacataaa   1440

cagaggccgg gaacggggcg gggaggaggg agagcacagg ctttgaccga tagtaacctc   1500

tgcgctcggt gcagccgaat ctataaaagg aactagtccc ggcaaaaacc ccgtaattgc   1560
```

-continued gagcgagagt gagtggggcc gggacccgca gagccgagcc gacccttctc tcccgggctg 1620
cggcagggca gggcggggag ctc 1643

<210> SEQ ID NO 4
<211> LENGTH: 748
<212> TYPE: DNA
<213> ORGANISM: Homo sapiens
<220> FEATURE:
<221> NAME/KEY: unsure
<222> LOCATION: (1)..(748)
<223> OTHER INFORMATION: All n's are unknown.

<400> SEQUENCE: 4
attccaanaa cattttccng catctgtggt tgccaactca caatgtcttt cattttctga 60
acttacccnc caaatgaagn tcggcacgca attatgtagt agcnactctt aggcccccgg 120
cttacactta tgcttccggc tngttgtgtg ggaattggac ggataccatt tcacncagga 180
aacagatatg nccatgatta cgccaagtta tttaggtgcn cgatagaata ctcaagcttg 240
gaattcgcgg ccgcagtcga cggacccccg ggaaagattc ctctcattac acaaaaacca 300
gacagtagtg gacgttgcag ttctcacatc ttctctacag gatgagaaag tgaaagaaag 360
ctatgtatga agaatcctgt tcatacgggg tggctgaaag taaagaggaa ctagactttc 420
ctttgcacca tgtgaagtgt tgtggagaaa agagccagaa gttgatgtgg gaagaagtaa 480
actggatact gtactgatac tattcaatgc aatgcaattc aatgcaatga aaacaaaatt 540
ccattacagg ggcagtgcct ttgtagccta tgtcttgtat ggctctcaag tgaaagactt 600
gaatttagtt ttttacctat acctatgtga aactctatta tggaacccaa tggacatatg 660
ggtttgaact cacacttttt ttttttgtt cctgtgtatt ctcattgggg ttgcaacaat 720
aattcatcaa gtaaaaaaaa aaaaaaaa 748

<210> SEQ ID NO 5
<211> LENGTH: 2011
<212> TYPE: DNA
<213> ORGANISM: Homo sapiens

<400> SEQUENCE: 5
agaatcctgt tcatactggg gtggcttgaa agtaaatgga ggaactagac tttcctttgc 60
accatgtgaa gtgttgtgga gaaaagagcc agaagttgat gtgggaagaa gtaaactgga 120
tactgtactg atactattca atgcaatgca attcaatgca atgaaaacaa aattccatta 180
caggggcaag tgcctttgta gcccatgtct tgtatggctc tcaagtgaaa gacttgaatt 240
tagtttttta cctataccta tgtgaaactc tattatggaa cccaatggac atatgggttt 300
gaactcacac tttttttttt ttttgttcct gtgtattctc attggggttg caacaataat 360
tcatcaagta atcatggcca gcgattattg atcaaaatca aaaggtaatg cacatcctca 420
ttcactaagc catgccatgc ccaggagact ggtttcccgg tgacacatcc attgctggca 480
atgagtgtgc cagagttatt agtgccaagt ttttcagaaa gtttgaagca ccatggtgtg 540
tcatgctcac ttttgtgaaa gctgctctgc tcagagtcta tcaacattga atatcagttg 600
acagaatggt gccatgcgtg gctaacatcc tgctttgatt ccctctgata agctgttctg 660
gtggcagtaa catgcaacaa aaatgtgggt gtctctaggc acgggaaact tggttccatt 720
gttatattgt cctatgcttc gagccatggg tctacagggt catccttatg agactcttaa 780
atatacttag atcctggtaa gaggcaaaga atcaacagcc aaactgctgg ggctgcaagc 840
tgctgaagcc agggcatggg attaaagaga ttgtgcgttc aaacctaggg aagcctgtgc 900

-continued

```
ccatttgtcc tgactgtctg ctaacatggt acactgcatc tcaagatgtt tatctgacac    960
aagtgtatta tttctggctt tttgaattaa tctagaaaat gaaaagatgg agttgtattt   1020
tgacaaaaat gtttgtactt tttaatgtta tttggaattt taagttctat cagtgacttc   1080
tgaatcctta gaatggcctc tttgtagaac cctgtggtat agaggagtat ggccactgcc   1140
ccactatttt tattttctta tgtaagtttg catatcagtc atgactagtg cctagaaagc   1200
aatgtgatgg tcaggatctc atgacattat atttgagttt ctttcagatc atttaggata   1260
ctcttaatct cacttcatca atcaaatatt ttttgagtgt atgctgtagc tgaaagagta   1320
tgtacgtacg tataagacta gagagatatt aagtctcagt acacttcctg tgccatgtta   1380
ttcagctcac tggtttacaa atataggttg tcttgtggtt gtaggagccc actgtaacaa   1440
tattgggcag cctttttttt tttttttttt aattgcaaca atgcaaaagc caagaaagta   1500
taagggtcac aagtctaaac aatgaattct tcaacaggga aaacagctag ctagaaaact   1560
tgctgaaaac acaacttgtg tttatggcat ttagtacctt caaataattg gctttgcaga   1620
tattggatac cccattaaat ctgacagtct caaatttttc atctcttcaa tcactagtca   1680
agaaaaatat aaaaacaaca aatacttcca tatggagcat ttttcagagt tttctaaccc   1740
agtcttattt ttctagtcag taaacatttg taaaaatact gtttcactaa tacttactgt   1800
taactgtctt gagagaaaag aaaaatatga gagaactatt gtttggggaa gttcaagtga   1860
tctttcaata tcattactaa cttcttccac tttttccaaa atttgaatat taacgctaaa   1920
ggtgtaagga cttcagattt caaattaatc tttctatatt ttttaaattt acagaatatt   1980
atataaccca ctgctgaaaa aaaaaaaaaa a                                  2011
```

<210> SEQ ID NO 6
<211> LENGTH: 3366
<212> TYPE: DNA
<213> ORGANISM: Homo sapiens
<220> FEATURE:
<221> NAME/KEY: unsure
<222> LOCATION: (1)..(3366)
<223> OTHER INFORMATION: All n's are unknown.

<400> SEQUENCE: 6

```
agaatcctgt tcatacgggg tggctgaaag taaagaggaa ctagactttc ctttgcacca     60
tgtgaagtgt tgtggagaaa agagccagaa gttgatgtgg gaagaagtaa actggatact    120
gtactgatac tattcaatgc aatgcaattc aatgcaatga aaacaaaatt ccattacagg    180
ggcagtgcct ttgtagccta tgtcttgtat ggctctcaag tgaaagactt gaatttagtt    240
ttttacctat acctatgtga aactctatta tggaacccaa tggacatatg ggtttgaact    300
cacacttttt tttttttttt gttcctgtgt attctcattg gggttgcaac aataattcat    360
caagtaatca tggccagcga ttattgatca aaatcaaaag gtaatgcaca tcctcattca    420
ctaagccatg ccatgcccag gagactggtt tcccggtgac acatccattg ctggcaatga    480
gtgtgccaga gttattagtg ccaagttttt cagaaagttt gaagcaccat ggtgtgtcat    540
gctcactttt gtgaaagctg ctctgctcag agtctatcaa cattgaatat cagttgacag    600
aatggtgcca tgcgtggcta acatcctgct ttgattccct ctgataagct gttctggtgg    660
cagtaacatg caacaaaaat gtgggtgtct ctaggcacgg gaaacttggt tccattgtta    720
tattgtccta tgcttcgagc catgggtcta cagggtcatc cttatgagac tcttaaatat    780
acttagatcc tggtaagagg caaagaatca acagccaaac tgctggggct gcaagctgct    840
```

-continued

```
gaagccaggg catgggatta aagagattgt gcgttcaaac ctagggaagc ctgtgcccat    900
ttgtcctgac tgtctgctaa catggtacac tgcatctcaa gatgtttatc tgacacaagt    960
gtattatttc tggcttttg aattaatcta gaaaatgaaa agatggagtt gtattttgac   1020
aaaaatgttt gtacttttta atgttatttg gaattttaag ttctatcagt gacttctgaa   1080
tccttagaat ggcctctttg tagaaccctg tggtatagag gagtatggcc actgccccac   1140
tatttttatt ttcttatgta agtttgcata tcagtcatga ctagtgccta gaaagcaatg   1200
tgatggtcag gatctcatga cattatattt gagtttcttt cagatcattt aggatactct   1260
taatctcact tcatcaatca aatatttttt gagtgtatgc tgtagctgaa agagtatgta   1320
cgtacgtata agactagaga gatattaagt ctcagtacac ttcctgtgcc atgttattca   1380
gctcactggt ttacaaatat aggttgtctt gtggttgtag gagcccactg taacaatatt   1440
gggcagcctt ttttttttt ttttaattgc aacaatgcaa aagccaagaa agtataaggg   1500
tcacaagttt aaacaatgaa ttcttcaaca gggaaaacag ctagcttgaa aacttgctga   1560
aaaacacaac ttgtgtttat ggcatttagt accttcaaat aattggcttt gcagatattg   1620
gataccccat taaatctgac agtctcaaat ttttcatctc ttcaatcact agtcaagaaa   1680
aatataaaaa caacaaatac ttccatatgg agcatttttc agagttttct aacccagtct   1740
tatttttcta gtcagtaaac atttgtaaaa atactgtttc actaatactt actgttaact   1800
gtcttgagag aaaagaaaaa tatgagagaa ctattgtttg gggaagttca agtgatcttt   1860
caatatcatt actaacttct tccacttttt ccaaaatttg aatattaacg ctaaaggtgt   1920
aagacttcag atttcaaatt aatctttcta tattttttaa atttacagaa tattatataa   1980
cccactgctg aaaaagaaaa aaatgattgt tttagaagtt aaagtcaata ttgattttaa   2040
atataagtaa tgaaggcata tttccaataa ctagtgatat ggcatcgttg caatttacag   2100
tatcttcaaa aatacagaat ttatagaata atttctcctc atttaatatt tttcaaaatc   2160
aaagttatgg tttcctcatt ttactaaaat cgtattctaa ttcttcatta tagtaaatct   2220
atgagcaact ccttacttcg gttcctctga tttcaaggcc atattttaaa aaatcaaaag   2280
gcactgtgaa ctattttgaa gaaaacacga cattttaata cagattgaaa ggacctcttc   2340
tgaagctaga aacaatctat agttatacat cttcattaat actgtgttac cttttaaaat   2400
agtaattttt tacattttcc tgtgtaaacc taattgtggt agaaattttt accaactcta   2460
tactcaatca agcaaaattt ctgtatattc cctgtggaat gtacctatgt gagtttcaga   2520
aattctcaaa atacgtgttc aaaaatttct gcttttgcat ctttgggaca cctcagaaaa   2580
cttattaaca actgtgaata tgagaaatac agaagaaaat aataagccct ctatacataa   2640
atgcccagca caattcattg ttaaaaaaca accaaacctc acactactgt atttcattat   2700
ctgtactgaa agcaaatgct ttgtgactat taaatgttgc acatcattca ttcactgtat   2760
agtaatcatt gactaaagcc atttgctgtg ttttcttctt gtggntgnat atatcaggta   2820
aaatattttc caaagagcca tgtgtcatgt aatactgaac cctttgatat tgagacatta   2880
atttggaccc ttggtattat ctactagaat aatgtaatac tgnagaaata ttgctctaat   2940
tctttcaaaa tggtgcatcc cccttaaaan gttctatttc cataaggatt tagcttgctt   3000
atcccttctt ataccctaag atgaagctgt ttttgtgctc tttgttcatc attggccctc   3060
attccaagca ctttacgctg tctgtaatgg gatctatttt tgcactggaa tatctgagaa   3120
ttgcaaaact agacaaaagt ttcacaacag atttctaagt taaatcattt tcattaaaag   3180
gaaaaaagaa aaaaaatttt gtatgtcaat aactttatat gaagtattaa aatgcatatt   3240
```

-continued

```
tctatgttgt aatataatga gtcacaaaat aaagctgtga cagttctgtt aaaaaaaaaa   3300

aaaaaaaaaa aaaaaaaaaa aaaaaaaaaa aaaaaaaaaa aaaaaaaaaa aaaaaaaaaa   3360

aaaaaa                                                              3366
```

<210> SEQ ID NO 7
<211> LENGTH: 10474
<212> TYPE: DNA
<213> ORGANISM: Homo sapiens
<220> FEATURE:
<221> NAME/KEY: unsure
<222> LOCATION: (1)..(10474)
<223> OTHER INFORMATION: All n's are unknown.

<400> SEQUENCE: 7

```
tctagaactg ggtaccagct gctagcaagc ttcggcacga gccgcagagc cgagccgacc     60

cttctctccc gggctgcggc agggcagggc ggggagctcc gcgcaccaac agagccggtt    120

ctcagggcgc tttgctcctt gttttttccc cggttctgtt ttctcccctt ctccggaagg    180

cttgtcaagg ggtaggagaa agagacgcaa acacaaaagt ggaaaacagt taatgaccag    240

ccacgggcgt ccctgctgtg agctctggcc gctgccttcc agggctcccg agccacacgc    300

tgggcgtgct ggctgaggga acatggcttg ttggcctcag ctgaggttgc tgctgtggaa    360

gaacctcact ttcagaagaa gacaaacatg tcagctgtta ctggaagtgg cctggcctct    420

atttatcttc ctgatcctga tctctgttcg gctgagctac ccaccctatg aacaacatga    480

atgccatttt ccaaataaag ccatgccctc tgcaggaaca cttccttggg ttcaggggat    540

tatctgtaat gccaacaacc cctgtttccg ttacccgact cctggggagg ctcccggagt    600

tgttggaaac tttaacaaat ccattgtggc tcgcctgttc tcagatgctc ggaggcttct    660

tttatacagc cagaaagaca ccagcatgaa ggacatgcgc aaagttctga gaacattaca    720

gcagatcaag aaatccagct caaacttgaa gcttcaagat ttcctggtgg acaatgaaac    780

cttctctggg ttcctatatc acaacctctc tctcccaaag tctactgtgg acaagatgct    840

gagggctgat gtcattctcc acaaggtatt tttgcaaggc taccagttac atttgacaag    900

tctgtgcaat ggatcaaaat cagaagagat gattcaactt ggtgaccaag aagtttctga    960

gctttgtggc ctaccaaagg agaaactggc tgcagcagag cgagtacttc gttccaacat   1020

ggacatcctg aagccaatcc tgagaacact aaactctaca tctcccttcc cgagcaagga   1080

gctggctgaa gccacaaaaa cattgctgca tagtcttggg actctggccc aggagctgtt   1140

cagcatgaga agctggagtg acatgcgaca ggaggtgatg tttctgacca atgtgaacag   1200

ctccagctcc tccacccaaa tctaccaggc tgtgtctcgt attgtctgcg ggcatcccga   1260

gggagggggg ctgaagatca agtctctcaa ctggtatgag gacaacaact acaaagccct   1320

ctttggaggc aatggcactg aggaagatgc tgaaaccttc tatgacaact ctacaactcc   1380

ttactgcaat gatttgatga agaatttgga gtctagtcct ctttcccgca ttatctggaa   1440

agctctgaag ccgctgctcg ttgggaagat cctgtataca cctgacactc cagccacaag   1500

gcaggtcatg gctgaggtga acaagacctt ccaggaactg gctgtgttcc atgatctgga   1560

aggcatgtgg gaggaactca gccccaagat ctggaccttc atggagaaca gccaagaaat   1620

ggaccttgtc cggatgctgt tggacagcag ggacaatgac cacttttggg aacagcagtt   1680

ggatggctta gattggacag cccaagacat cgtggcgttt ttggccaagc acccagagga   1740

tgtccagtcc agtaatggtt ctgtgtacac ctggagagaa gctttcaacg agactaacca   1800
```

-continued

```
ggcaatccgg accatatctc gcttcatgga gtgtgtcaac ctgaacaagc tagaacccat   1860
agcaacagaa gtctggctca tcaacaagtc catggagctg ctggatgaga ggaagttctg   1920
ggctggtatt gtgttcactg gaattactcc aggcagcatt gagctgcccc atcatgtcaa   1980
gtacaagatc cgaatggaca ttgacaatgt ggagaggaca aataaaatca aggatgggta   2040
ctgggaccct ggtcctcgag ctgacccctt tgaggacatg cggtacgtct ggggggggctt   2100
cgcctacttg cgggatgtgg tggagcaggc aatcatcagg gtgctgacgg gcaccgagaa   2160
gaaaactggt gtctatatgc aacagatgcc ctatccctgt tacgttgatg acatctttct   2220
gcgggtgatg agccggtcaa tgcccctctt catgacgctg gcctggattt actcagtggc   2280
tgtgatcatc aagggcatcg tgtatgagaa ggaggcacgg ctgaaagaga ccatgcggat   2340
catgggcctg gacaacagca tactctggtt tagctggttc attagtagcc tcattcctct   2400
tcttgtgagc gctggcctgc tagtggtcat cctgaagtta ggaaacctgc tgccctacag   2460
tgatcccagc gtggtgtttg tcttcctgtc cgtgtttgct gtggtgacaa tcctgcagtg   2520
cttcctgatt agcacactct tctccagagc caacctggca gcagcctgtg gggcatcat   2580
ctacttcacg ctgtacctgc cctacgtcct gtgtgtggca tggcaggact acgtgggctt   2640
cacactcaag atcttcgcta gcctgctgtc tcctgtggct tttgggtttg gctgtgagta   2700
ctttgccctt tttgaggagc agggcattgg agtgcagtgg gacaacctgt ttgagagtcc   2760
tgtggaggaa gatggcttca atctcaccac ttcgatctcc atgatgctgt ttgacacctt   2820
cctctatggg gtgatgacct ggtacattga ggctgtcttt ccaggccagt acggaattcc   2880
caggccctgg tattttcctt gcaccaagtc ctactggttt ggcgaggaaa gtgatgagaa   2940
gagccaccct ggttccaacc agaagagaat gtcagaaatc tgcatggagg aggaacccac   3000
ccacttgaag ctgggcgtgt ccattcagaa cctggtaaaa gtctaccgag atgggatgaa   3060
ggtggctgtc gatggcctgg cactgaattt ttatgagggc cagatcacct ccttcctggg   3120
ccacaatgga gcggggaaga cgaccaccat gtcaatcctg accgggttgt tccccccgac   3180
ctcgggcacc gcctacatcc tgggaaaaga cattcgctct gagatgagca ccatccggca   3240
gaacctgggg gtctgtcccc agcataacgt gctgtttgac atgctgactg tcgaagaaca   3300
catctggttc tatgcccgct tgaaagggct ctctgagaag cacgtgaagg cggagatgga   3360
gcagatggcc ctggatgttg gtttgccatc aagcaagctg aaaagcaaaa caagccagct   3420
gtcaggtgga atgcagagaa agctatctgt ggccttggcc tttgtcgggg gatctaaggt   3480
tgtcattctg gatgaaccca cagctggtgt ggaccccttac tcccgcaggg gaatatggga   3540
gctgctgctg aaataccgac aaggccgcac cattattctc tctacacacc acatggatga   3600
agcggacgtc ctgggggaca ggattgccat catctcccat gggaagctgt gctgtgtggg   3660
ctcctccctg tttctgaaga accagctggg aacaggctac tacctgacct tggtcaagaa   3720
agatgtggaa tcctccctca gttcctgcag aaacagtagt agcactgtgt catacctgaa   3780
aaaggaggac agtgtttctc agagcagttc tgatgctggc ctgggcagcg accatgagag   3840
tgacacgctg accatcgatg tctctgctat ctccaacctc atcaggaagc atgtgtctga   3900
agcccggctg gtggaagaca tagggcatga gctgacctat gtgctgccat atgaagctgc   3960
taaggaggga gcctttgtgg aactctttca tgagattgat gaccggctct cagacctggg   4020
catttctagt tatggcatct cagagacgac cctggaagaa atattcctca aggtggccga   4080
agagagtggg gtggatgctg agacctcaga tggtaccttg ccagcaagac gaaacaggcg   4140
ggccttcggg gacaagcaga gctgtcttcg cccgttcact gaagatgatg ctgctgatcc   4200
```

-continued

```
aaatgattct gacatagacc cagaatccag agagacagac ttgctcagtg ggatggatgg   4260
caaagggtcc taccaggtga aaggctggaa acttacacag caacagtttg tggccctttt   4320
gtggaagaga ctgctaattg ccagacggag tcggaaagga ttttttgctc agattgtctt   4380
gccagctgtg tttgtctgca ttgcccttgt gttcagcctg atcgtgccac cctttggcaa   4440
gtaccccagc ctggaacttc agccctggat gtacaacgaa cagtacacat ttgtcagcaa   4500
tgatgctcct gaggacacgg gaaccctgga actcttaaac gccctcacca aagaccctgg   4560
cttcgggacc cgctgtatgg aaggaaaccc aatcccagac acgccctgcc aggcagggga   4620
ggaagagtgg accactgccc cagttcccca gaccatcatg gacctcttcc agaatgggaa   4680
ctggacaatg cagaaccctt cacctgcatg ccagtgtagc agcgacaaaa tcaagaagat   4740
gctgcctgtg tgtcccccag gggcaggggg gctgcctcct ccacaaagaa aacaaaacac   4800
tgcagatatc cttcaggacc tgacaggaag aaacatttcg gattatctgg tgaagacgta   4860
tgtgcagatc atagccaaaa gcttaaagaa caagatctgg gtgaatgagt ttaggtatgg   4920
cggcttttcc ctgggtgtca gtaatactca agcacttcct ccgagtcaag aagttaatga   4980
tgccatcaaa caaatgaaga aacacctaaa gctggccaag gacagttctg cagatcgatt   5040
tctcaacagc ttgggaagat ttatgacagg actggacacc agaaataatg tcaaggtgtg   5100
gttcaataac aagggctggc atgcaatcag ctctttcctg aatgtcatca acaatgccat   5160
tctccgggcc aacctgcaaa agggagagaa ccctagccat tatggaatta ctgctttcaa   5220
tcatcccctg aatctcacca agcagcagct ctcagaggtg gctctgatga ccacatcagt   5280
ggatgtcctt gtgtccatct gtgtcatctt tgcaatgtcc ttcgtcccag ccagctttgt   5340
cgtattcctg atccaggagc gggtcagcaa agcaaaacac ctgcagttca tcagtggagt   5400
gaagcctgtc atctactggc tctctaattt tgtctgggat atgtgcaatt acgttgtccc   5460
tgccacactg gtcattatca tcttcatctg cttccagcag aagtcctatg tgtcctccac   5520
caatctgcct gtgctagccc ttctactttt gctgtatggg tggtcaatca cacctctcat   5580
gtacccagcc tcctttgtgt tcaagatccc cagcacagcc tatgtggtgc tcaccagcgt   5640
gaacctcttc attggcatta atggcagcgt ggccaccttt gtgctggagc tgttcaccga   5700
caataagctg aataatatca atgatatcct gaagtccgtg ttcttgatct tcccacattt   5760
ttgcctggga cgagggctca tcgacatggt gaaaaaccag gcaatggctg atgccctgga   5820
aaggtttggg gagaatcgct ttgtgtcacc attatcttgg gacttggtgg gacgaaacct   5880
cttcgccatg gccgtggaag ggtggtgtt cttcctcatt actgttctga tccagtacag   5940
attcttcatc aggcccagac ctgtaaatgc aaagctatct cctctgaatg atgaagatga   6000
agatgtgagg cgggaaagac agagaattct tgatggtgga ggccagaatg acatcttaga   6060
aatcaaggag ttgacgaaga tatatagaag gaagcggaag cctgctgttg acaggatttg   6120
cgtgggcatt cctcctggtg agtgctttgg gctcctggga gttaatgggg ctggaaaatc   6180
atcaactttc aagatgttaa caggagatac cactgttacc agaggagatg ctttccttaa   6240
caaaaatagt atcttatcaa acatccatga agtacatcag aacatgggct actgccctca   6300
gtttgatgcc atcacagagc tgttgactgg gagagaacac gtggagttct ttgccctttt   6360
gagaggagtc ccagagaaag aagttggcaa ggttggtgag tgggcgattc ggaaactggg   6420
cctcgtgaag tatggagaaa aatatgctgg taactatagt ggaggcaaca aacgcaagct   6480
ctctacagcc atggctttga tcggcgggcc tcctgtggtg tttctggatg aacccaccac   6540
```

-continued

```
aggcatggat cccaaagccc ggcggttctt gtggaattgt gccctaagtg ttgtcaagga   6600
ggggagatca gtagtgctta catctcatag tatggaagaa tgtgaagctc tttgcactag   6660
gatggcaatc atggtcaatg gaaggttcag gtgccttggc agtgtccagc atctaaaaaa   6720
taggtttgga gatggttata caatagttgt acgaatagca gggtccaacc cggacctgaa   6780
gcctgtccag gatttctttg gacttgcatt tcctggaagt gttctaaaag agaaacaccg   6840
gaacatgcta caataccagc ttccatcttc attatcttct ctggccagga tattcagcat   6900
cctctcccag agcaaaaagc gactccacat agaagactac tctgtttctc agacaacact   6960
tgaccaagta tttgtgaact ttgccaagga ccaaagtgat gatgaccact taaaagacct   7020
ctcattacac aaaaaccaga cagtagtgga cgttgcagtt ctcacatctt ttctacagga   7080
tgagaaagtg aaagaaagct atgtatgaag aatcctgttc atacggggtg gctgaaagta   7140
aagaggaact agactttcct ttgcaccatg tgaagtgttg tggagaaaag agccagaagt   7200
tgatgtggga agaagtaaac tggatactgt actgatacta ttcaatgcaa tgcaattcaa   7260
tgcaatgaaa acaaaattcc attacagggg cagtgccttt gtagcctatg tcttgtatgg   7320
ctctcaagtg aaagacttga atttagtttt ttacctatac ctatgtgaaa ctctattatg   7380
gaacccaatg gacatatggg tttgaactca cacttttttt tttttttgt tcctgtgtat   7440
tctcattggg gttgcaacaa taattcatca agtaatcatg gccagcgatt attgatcaaa   7500
atcaaaaggt aatgcacatc ctcattcact aagccatgcc atgcccagga gactggtttc   7560
ccggtgacac atccattgct ggcaatgagt gtgccagagt tattagtgcc aagtttttca   7620
gaaagtttga agcaccatgg tgtgtcatgc tcacttttgt gaaagctgct ctgctcagag   7680
tctatcaaca ttgaatatca gttgacagaa tggtgccatg cgtggctaac atcctgcttt   7740
gattccctct gataagctgt tctggtggca gtaacatgca acaaaaatgt gggtgtctct   7800
aggcacggga aacttggttc cattgttata ttgtcctatg cttcgagcca tgggtctaca   7860
gggtcatcct tatgagactc ttaaatatac ttagatcctg gtaagaggca aagaatcaac   7920
agccaaactg ctggggctgc aagctgctga agccagggca tgggattaaa gagattgtgc   7980
gttcaaacct agggaagcct gtgcccattt gtcctgactg tctgctaaca tggtacactg   8040
catctcaaga tgtttatctg acacaagtgt attatttctg gctttttgaa ttaatctaga   8100
aaatgaaaag atggagttgt attttgacaa aaatgtttgt actttttaat gttatttgga   8160
attttaagtt ctatcagtga cttctgaatc cttagaatgg cctctttgta gaaccctgtg   8220
gtatagagga gtatggccac tgccccacta tttttatttt cttatgtaag tttgcatatc   8280
agtcatgact agtgcctaga aagcaatgtg atggtcagga tctcatgaca ttatatttga   8340
gtttctttca gatcatttag gatactctta atctcacttc atcaatcaaa tattttttga   8400
gtgtatgctg tagctgaaag agtatgtacg tacgtataag actagagaga tattaagtct   8460
cagtacactt cctgtgccat gttattcagc tcactggttt acaaatatag gttgtcttgt   8520
ggttgtagga gcccactgta acaatattgg gcagcctttt tttttttttt ttaattgcaa   8580
caatgcaaaa gccaagaaag tataagggtc acaagtttaa acaatgaatt cttcaacagg   8640
gaaaacagct agcttgaaaa cttgctgaaa aacacaactt gtgtttatgg catttagtac   8700
cttcaaataa ttggctttgc agatattgga taccccatta aatctgacag tctcaaattt   8760
ttcatctctt caatcactag tcaagaaaaa tataaaaaca acaaatactt ccatatggag   8820
catttttcag agttttctaa cccagtctta tttttctagt cagtaaacat ttgtaaaaat   8880
actgtttcac taatacttac tgttaactgt cttgagagaa aagaaaaata tgagagaact   8940
```

-continued

```
attgtttggg gaagttcaag tgatctttca atatcattac taacttcttc cactttttcc   9000
aaaatttgaa tattaacgct aaaggtgtaa gacttcagat ttcaaattaa tctttctata   9060
ttttttaaat ttacagaata ttatataacc cactgctgaa aaagaaaaaa atgattgttt   9120
tagaagttaa agtcaatatt gattttaaat ataagtaatg aaggcatatt tccaataact   9180
agtgatatgg catcgttgca atttacagta tcttcaaaaa tacagaattt atagaataat   9240
ttctcctcat ttaatatttt tcaaaatcaa agttatggtt tcctcatttt actaaaatcg   9300
tattctaatt cttcattata gtaaatctat gagcaactcc ttacttcggt tcctctgatt   9360
tcaaggccat attttaaaaa atcaaaaggc actgtgaact attttgaaga aaacacgaca   9420
ttttaataca gattgaaagg acctcttctg aagctagaaa caatctatag ttatacatct   9480
tcattaatac tgtgttacct tttaaaatag taattttta cattttcctg tgtaaaccta   9540
attgtggtag aaatttttac caactctata ctcaatcaag caaaatttct gtatattccc   9600
tgtggaatgt acctatgtga gtttcagaaa ttctcaaaat acgtgttcaa aaatttctgc   9660
ttttgcatct ttgggacacc tcagaaaact tattaacaac tgtgaatatg agaaatacag   9720
aagaaaataa taagccctct atacataaat gcccagcaca attcattgtt aaaaaacaac   9780
caaacctcac actactgtat ttcattatct gtactgaaag caaatgcttt gtgactatta   9840
aatgttgcac atcattcatt cactgtatag taatcattga ctaaagccat ttgctgtgtt   9900
ttcttcttgt ggntgnatat atcaggtaaa atattttcca aagagccatg tgtcatgtaa   9960
tactgaaccc tttgatattg agacattaat ttggaccctt ggtattatct actagaataa  10020
tgtaatactg nagaaatatt gctctaattc tttcaaaatg gtgcatcccc cttaaaangt  10080
tctatttcca taaggattta gcttgcttat cccttcttat accctaagat gaagctgttt  10140
ttgtgctctt tgttcatcat tggccctcat tccaagcact ttacgctgtc tgtaatggga  10200
tctatttttg cactggaata tctgagaatt gcaaaactag acaaaagttt cacaacagat  10260
ttctaagtta aatcattttc attaaaagga aaaaagaaaa aaaattttgt atgtcaataa  10320
ctttatatga agtattaaaa tgcatatttc tatgttgtaa tataatgagt cacaaaataa  10380
agctgtgaca gttctgttaa aaaaaaaaaa aaaaaaaaaa aaaaaaaaaa aaaaaaaaaa  10440
aaaaaaaaaa aaaaaaaaaa aaaaaaaaaa aaaa                             10474
```

<210> SEQ ID NO 8
<211> LENGTH: 2261
<212> TYPE: PRT
<213> ORGANISM: Homo sapiens

<400> SEQUENCE: 8

```
Met Ala Cys Trp Pro Gln Leu Arg Leu Leu Leu Trp Lys Asn Leu Thr
  1               5                  10                  15

Phe Arg Arg Arg Gln Thr Cys Gln Leu Leu Leu Glu Val Ala Trp Pro
             20                  25                  30

Leu Phe Ile Phe Leu Ile Leu Ile Ser Val Arg Leu Ser Tyr Pro Pro
         35                  40                  45

Tyr Glu Gln His Glu Cys His Phe Pro Asn Lys Ala Met Pro Ser Ala
     50                  55                  60

Gly Thr Leu Pro Trp Val Gln Gly Ile Ile Cys Asn Ala Asn Asn Pro
 65                  70                  75                  80

Cys Phe Arg Tyr Pro Thr Pro Gly Glu Ala Pro Gly Val Val Gly Asn
                 85                  90                  95
```

-continued

```
Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Ser Asn Leu Lys Leu
    130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
        195                 200                 205

Gln Glu Val Ser Glu Leu Cys Gly Leu Pro Lys Glu Lys Leu Ala Ala
    210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
            260                 265                 270

Phe Ser Met Arg Ser Trp Ser Asp Met Arg Gln Glu Val Met Phe Leu
        275                 280                 285

Thr Asn Val Asn Ser Ser Ser Ser Ser Thr Gln Ile Tyr Gln Ala Val
    290                 295                 300

Ser Arg Ile Val Cys Gly His Pro Glu Gly Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
        435                 440                 445

Trp Glu Gln Gln Leu Asp Gly Leu Asp Trp Thr Ala Gln Asp Ile Val
    450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
```

-continued

```
        515                 520                 525

Glu Arg Lys Phe Trp Ala Gly Ile Val Phe Thr Gly Ile Thr Pro Gly
    530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Arg Asp Val Val Glu Gln Ala Ile Ile Arg Val Leu
        595                 600                 605

Thr Gly Thr Glu Lys Lys Thr Gly Val Tyr Met Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Ile Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ser Asp Glu Lys Ser His Pro Gly Ser Asn Gln
865                 870                 875                 880

Lys Arg Met Ser Glu Ile Cys Met Glu Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940
```

-continued

Ile Leu Thr Gly Leu Phe Pro Pro Thr Ser Gly Thr Ala Tyr Ile Leu
945 950 955 960

Gly Lys Asp Ile Arg Ser Glu Met Ser Thr Ile Arg Gln Asn Leu Gly
965 970 975

Val Cys Pro Gln His Asn Val Leu Phe Asp Met Leu Thr Val Glu Glu
980 985 990

His Ile Trp Phe Tyr Ala Arg Leu Lys Gly Leu Ser Glu Lys His Val
995 1000 1005

Lys Ala Glu Met Glu Gln Met Ala Leu Asp Val Gly Leu Pro Ser Ser
1010 1015 1020

Lys Leu Lys Ser Lys Thr Ser Gln Leu Ser Gly Gly Met Gln Arg Lys
1025 1030 1035 1040

Leu Ser Val Ala Leu Ala Phe Val Gly Gly Ser Lys Val Val Ile Leu
1045 1050 1055

Asp Glu Pro Thr Ala Gly Val Asp Pro Tyr Ser Arg Arg Gly Ile Trp
1060 1065 1070

Glu Leu Leu Leu Lys Tyr Arg Gln Gly Arg Thr Ile Ile Leu Ser Thr
1075 1080 1085

His His Met Asp Glu Ala Asp Val Leu Gly Asp Arg Ile Ala Ile Ile
1090 1095 1100

Ser His Gly Lys Leu Cys Cys Val Gly Ser Ser Leu Phe Leu Lys Asn
1105 1110 1115 1120

Gln Leu Gly Thr Gly Tyr Tyr Leu Thr Leu Val Lys Lys Asp Val Glu
1125 1130 1135

Ser Ser Leu Ser Ser Cys Arg Asn Ser Ser Ser Thr Val Ser Tyr Leu
1140 1145 1150

Lys Lys Glu Asp Ser Val Ser Gln Ser Ser Ser Asp Ala Gly Leu Gly
1155 1160 1165

Ser Asp His Glu Ser Asp Thr Leu Thr Ile Asp Val Ser Ala Ile Ser
1170 1175 1180

Asn Leu Ile Arg Lys His Val Ser Glu Ala Arg Leu Val Glu Asp Ile
1185 1190 1195 1200

Gly His Glu Leu Thr Tyr Val Leu Pro Tyr Glu Ala Ala Lys Glu Gly
1205 1210 1215

Ala Phe Val Glu Leu Phe His Glu Ile Asp Asp Arg Leu Ser Asp Leu
1220 1225 1230

Gly Ile Ser Ser Tyr Gly Ile Ser Glu Thr Thr Leu Glu Glu Ile Phe
1235 1240 1245

Leu Lys Val Ala Glu Glu Ser Gly Val Asp Ala Glu Thr Ser Asp Gly
1250 1255 1260

Thr Leu Pro Ala Arg Arg Asn Arg Arg Ala Phe Gly Asp Lys Gln Ser
1265 1270 1275 1280

Cys Leu Arg Pro Phe Thr Glu Asp Asp Ala Ala Asp Pro Asn Asp Ser
1285 1290 1295

Asp Ile Asp Pro Glu Ser Arg Glu Thr Asp Leu Leu Ser Gly Met Asp
1300 1305 1310

Gly Lys Gly Ser Tyr Gln Val Lys Gly Trp Lys Leu Thr Gln Gln Gln
1315 1320 1325

Phe Val Ala Leu Leu Trp Lys Arg Leu Leu Ile Ala Arg Arg Ser Arg
1330 1335 1340

Lys Gly Phe Phe Ala Gln Ile Val Leu Pro Ala Val Phe Val Cys Ile
1345 1350 1355 1360

-continued

```
Ala Leu Val Phe Ser Leu Ile Val Pro Pro Phe Gly Lys Tyr Pro Ser
                1365                1370                1375

Leu Glu Leu Gln Pro Trp Met Tyr Asn Glu Gln Tyr Thr Phe Val Ser
            1380                1385                1390

Asn Asp Ala Pro Glu Asp Thr Gly Thr Leu Glu Leu Leu Asn Ala Leu
        1395                1400                1405

Thr Lys Asp Pro Gly Phe Gly Thr Arg Cys Met Glu Gly Asn Pro Ile
    1410                1415                1420

Pro Asp Thr Pro Cys Gln Ala Gly Glu Glu Glu Trp Thr Thr Ala Pro
1425                1430                1435                1440

Val Pro Gln Thr Ile Met Asp Leu Phe Gln Asn Gly Asn Trp Thr Met
                1445                1450                1455

Gln Asn Pro Ser Pro Ala Cys Gln Cys Ser Ser Asp Lys Ile Lys Lys
            1460                1465                1470

Met Leu Pro Val Cys Pro Pro Gly Ala Gly Gly Leu Pro Pro Pro Gln
        1475                1480                1485

Arg Lys Gln Asn Thr Ala Asp Ile Leu Gln Asp Leu Thr Gly Arg Asn
    1490                1495                1500

Ile Ser Asp Tyr Leu Val Lys Thr Tyr Val Gln Ile Ile Ala Lys Ser
1505                1510                1515                1520

Leu Lys Asn Lys Ile Trp Val Asn Glu Phe Arg Tyr Gly Gly Phe Ser
                1525                1530                1535

Leu Gly Val Ser Asn Thr Gln Ala Leu Pro Pro Ser Gln Glu Val Asn
            1540                1545                1550

Asp Ala Ile Lys Gln Met Lys Lys His Leu Lys Leu Ala Lys Asp Ser
        1555                1560                1565

Ser Ala Asp Arg Phe Leu Asn Ser Leu Gly Arg Phe Met Thr Gly Leu
    1570                1575                1580

Asp Thr Arg Asn Asn Val Lys Val Trp Phe Asn Asn Lys Gly Trp His
1585                1590                1595                1600

Ala Ile Ser Ser Phe Leu Asn Val Ile Asn Asn Ala Ile Leu Arg Ala
                1605                1610                1615

Asn Leu Gln Lys Gly Glu Asn Pro Ser His Tyr Gly Ile Thr Ala Phe
            1620                1625                1630

Asn His Pro Leu Asn Leu Thr Lys Gln Gln Leu Ser Glu Val Ala Leu
        1635                1640                1645

Met Thr Thr Ser Val Asp Val Leu Val Ser Ile Cys Val Ile Phe Ala
    1650                1655                1660

Met Ser Phe Val Pro Ala Ser Phe Val Val Phe Leu Ile Gln Glu Arg
1665                1670                1675                1680

Val Ser Lys Ala Lys His Leu Gln Phe Ile Ser Gly Val Lys Pro Val
                1685                1690                1695

Ile Tyr Trp Leu Ser Asn Phe Val Trp Asp Met Cys Asn Tyr Val Val
            1700                1705                1710

Pro Ala Thr Leu Val Ile Ile Ile Phe Ile Cys Phe Gln Gln Lys Ser
        1715                1720                1725

Tyr Val Ser Ser Thr Asn Leu Pro Val Leu Ala Leu Leu Leu Leu Leu
    1730                1735                1740

Tyr Gly Trp Ser Ile Thr Pro Leu Met Tyr Pro Ala Ser Phe Val Phe
1745                1750                1755                1760

Lys Ile Pro Ser Thr Ala Tyr Val Val Leu Thr Ser Val Asn Leu Phe
                1765                1770                1775

Ile Gly Ile Asn Gly Ser Val Ala Thr Phe Val Leu Glu Leu Phe Thr
```

-continued

```
            1780                1785                1790

Asp Asn Lys Leu Asn Asn Ile Asn Asp Ile Leu Lys Ser Val Phe Leu
        1795                1800                1805

Ile Phe Pro His Phe Cys Leu Gly Arg Gly Leu Ile Asp Met Val Lys
    1810                1815                1820

Asn Gln Ala Met Ala Asp Ala Leu Glu Arg Phe Gly Glu Asn Arg Phe
1825                1830                1835                1840

Val Ser Pro Leu Ser Trp Asp Leu Val Gly Arg Asn Leu Phe Ala Met
                1845                1850                1855

Ala Val Glu Gly Val Val Phe Phe Leu Ile Thr Val Leu Ile Gln Tyr
            1860                1865                1870

Arg Phe Phe Ile Arg Pro Arg Pro Val Asn Ala Lys Leu Ser Pro Leu
        1875                1880                1885

Asn Asp Glu Asp Glu Asp Val Arg Arg Glu Arg Gln Arg Ile Leu Asp
    1890                1895                1900

Gly Gly Gly Gln Asn Asp Ile Leu Glu Ile Lys Glu Leu Thr Lys Ile
1905                1910                1915                1920

Tyr Arg Arg Lys Arg Lys Pro Ala Val Asp Arg Ile Cys Val Gly Ile
                1925                1930                1935

Pro Pro Gly Glu Cys Phe Gly Leu Leu Gly Val Asn Gly Ala Gly Lys
            1940                1945                1950

Ser Ser Thr Phe Lys Met Leu Thr Gly Asp Thr Thr Val Thr Arg Gly
        1955                1960                1965

Asp Ala Phe Leu Asn Lys Asn Ser Ile Leu Ser Asn Ile His Glu Val
    1970                1975                1980

His Gln Asn Met Gly Tyr Cys Pro Gln Phe Asp Ala Ile Thr Glu Leu
1985                1990                1995                2000

Leu Thr Gly Arg Glu His Val Glu Phe Phe Ala Leu Leu Arg Gly Val
                2005                2010                2015

Pro Glu Lys Glu Val Gly Lys Val Gly Glu Trp Ala Ile Arg Lys Leu
            2020                2025                2030

Gly Leu Val Lys Tyr Gly Glu Lys Tyr Ala Gly Asn Tyr Ser Gly Gly
        2035                2040                2045

Asn Lys Arg Lys Leu Ser Thr Ala Met Ala Leu Ile Gly Gly Pro Pro
    2050                2055                2060

Val Val Phe Leu Asp Glu Pro Thr Thr Gly Met Asp Pro Lys Ala Arg
2065                2070                2075                2080

Arg Phe Leu Trp Asn Cys Ala Leu Ser Val Val Lys Glu Gly Arg Ser
                2085                2090                2095

Val Val Leu Thr Ser His Ser Met Glu Glu Cys Glu Ala Leu Cys Thr
            2100                2105                2110

Arg Met Ala Ile Met Val Asn Gly Arg Phe Arg Cys Leu Gly Ser Val
        2115                2120                2125

Gln His Leu Lys Asn Arg Phe Gly Asp Gly Tyr Thr Ile Val Val Arg
    2130                2135                2140

Ile Ala Gly Ser Asn Pro Asp Leu Lys Pro Val Gln Asp Phe Phe Gly
2145                2150                2155                2160

Leu Ala Phe Pro Gly Ser Val Leu Lys Glu Lys His Arg Asn Met Leu
                2165                2170                2175

Gln Tyr Gln Leu Pro Ser Ser Leu Ser Ser Leu Ala Arg Ile Phe Ser
            2180                2185                2190

Ile Leu Ser Gln Ser Lys Lys Arg Leu His Ile Glu Asp Tyr Ser Val
        2195                2200                2205
```

-continued

Ser Gln Thr Thr Leu Asp Gln Val Phe Val Asn Phe Ala Lys Asp Gln
2210 2215 2220

Ser Asp Asp Asp His Leu Lys Asp Leu Ser Leu His Lys Asn Gln Thr
2225 2230 2235 2240

Val Val Asp Val Ala Val Leu Thr Ser Phe Leu Gln Asp Glu Lys Val
2245 2250 2255

Lys Glu Ser Tyr Val
2260

<210> SEQ ID NO 9
<211> LENGTH: 10474
<212> TYPE: DNA
<213> ORGANISM: Homo sapiens
<220> FEATURE:
<221> NAME/KEY: unsure
<222> LOCATION: (1)..(10474)
<223> OTHER INFORMATION: All n's are unknown.

<400> SEQUENCE: 9
tctagaactg ggtaccagct gctagcaagc ttcggcacga gccgcagagc cgagccgacc 60
cttctctccc gggctgcggc agggcagggc ggggagctcc gcgcaccaac agagccggtt 120
ctcagggcgc tttgctcctt gtttttttccc cggttctgtt ttctcccctt ctccggaagg 180
cttgtcaagg ggtaggagaa agagacgcaa acacaaaagt ggaaaacagt taatgaccag 240
ccacgggcgt ccctgctgtg agctctggcc gctgccttcc agggctcccg agccacacgc 300
tgggcgtgct ggctgaggga acatggcttg ttggcctcag ctgaggttgc tgctgtggaa 360
gaacctcact ttcagaagaa gacaaacatg tcagctgtta ctggaagtgg cctggcctct 420
atttatcttc ctgatcctga tctctgttcg gctgagctac ccaccctatg aacaacatga 480
atgccatttt ccaaataaag ccatgccctc tgcaggaaca cttccttggg ttcaggggat 540
tatctgtaat gccaacaacc cctgtttccg ttacccgact cctggggagg ctcccggagt 600
tgttggaaac tttaacaaat ccattgtggc tcgcctgttc tcagatgctc ggaggcttct 660
tttatacagc cagaaagaca ccagcatgaa ggacatgcgc aaagttctga gaacattaca 720
gcagatcaag aaatccagct caaacttgaa gcttcaagat ttcctggtgg acaatgaaac 780
cttctctggg ttcctatatc acaacctctc tctcccaaag tctactgtgg acaagatgct 840
gagggctgat gtcattctcc acaaggtatt tttgcaaggc taccagttac atttgacaag 900
tctgtgcaat ggatcaaaat cagaagagat gattcaactt ggtgaccaag aagtttctga 960
gctttgtggc ctaccaaagg agaaactggc tgcagcagag cgagtacttc gttccaacat 1020
ggacatcctg aagccaatcc tgagaacact aaactctaca tctcccttcc cgagcaagga 1080
gctggctgaa gccacaaaaa cattgctgca tagtcttggg actctggccc aggagctgtt 1140
cagcatgaga agctggagtg acatgcgaca ggaggtgatg tttctgacca atgtgaacag 1200
ctccagctcc tccacccaaa tctaccaggc tgtgtctcgt attgtctgcg ggcatcccga 1260
gggagggggg ctgaagatca agtctctcaa ctggtatgag gacaacaact acaaagccct 1320
ctttggaggc aatggcactg aggaagatgc tgaaaccttc tatgacaact ctacaactcc 1380
ttactgcaat gatttgatga agaatttgga gtctagtcct ctttcccgca ttatctggaa 1440
agctctgaag ccgctgctcg ttgggaagat cctgtataca cctgacactc cagccacaag 1500
gcaggtcatg gctgaggtga acaagacctt ccaggaactg gctgtgttcc atgatctgga 1560
aggcatgtgg gaggaactca gccccaagat ctggaccttc atggagaaca gccaagaaat 1620

-continued

```
ggaccttgtc cggatgctgt tggacagcag ggacaatgac cacttttggg aacagcagtt   1680
ggatggctta gattggacag cccaagacat cgtggcgttt ttggccaagc acccagagga   1740
tgtccagtcc agtaatggtt ctgtgtacac ctggagagaa gctttcaacg agactaacca   1800
ggcaatccgg accatatctc gcttcatgga gtgtgtcaac ctgaacaagc tagaacccat   1860
agcaacagaa gtctggctca tcaacaagtc catggagctg ctggatgaga ggaagttctg   1920
ggctggtatt gtgttcactg gaattactcc aggcagcatt gagctgcccc atcatgtcaa   1980
gtacaagatc cgaatggaca ttgacaatgt ggagaggaca aataaaatca aggatgggta   2040
ctgggaccct ggtcctcgag ctgacccctt tgaggacatg tggtacgtct ggggggggctt   2100
cgcctacttg caggatgtgg tggagcaggc aatcatcagg gtgctgacgg gcaccgagaa   2160
gaaaactggt gtctatatgc aacagatgcc ctatccctgt tacgttgatg acatctttct   2220
gcgggtgatg agccggtcaa tgcccctctt catgacgctg gcctggattt actcagtggc   2280
tgtgatcatc aagggcatcg tgtatgagaa ggaggcacgg ctgaaagaga ccatgcggat   2340
catgggcctg gacaacagca tactctggtt tagctggttc attagtagcc tcattcctct   2400
tcttgtgagc gctggcctgc tagtggtcat cctgaagtta ggaaacctgc tgccctacag   2460
tgatcccagc gtggtgtttg tcttcctgtc cgtgtttgct gtggtgacaa tcctgcagtg   2520
cttcctgatt agcacactct tctccagagc caacctggca gcagcctgtg gggcatcat   2580
ctacttcacg ctgtacctgc cctacgtcct gtgtgtggca tggcaggact acgtgggctt   2640
cacactcaag atcttcgcta gcctgctgtc tcctgtggct tttgggtttg gctgtgagta   2700
ctttgccctt tttgaggagc agggcattgg agtgcagtgg gacaacctgt ttgagagtcc   2760
tgtggaggaa gatggcttca atctcaccac ttcgatctcc atgatgctgt ttgacacctt   2820
cctctatggg gtgatgacct ggtacattga ggctgtcttt ccaggccagt acggaattcc   2880
caggccctgg tattttcctt gcaccaagtc ctactggttt ggcgaggaaa gtgatgagaa   2940
gagccaccct ggttccaacc agaagagaat gtcagaaatc tgcatggagg aggaacccac   3000
ccacttgaag ctgggcgtgt ccattcagaa cctggtaaaa gtctaccgag atgggatgaa   3060
ggtggctgtc gatggcctgg cactgaattt ttatgagggc cagatcacct ccttcctggg   3120
ccacaatgga gcggggaaga cgaccaccat gtcaatcctg accgggttgt tcccccccgac   3180
ctcgggcacc gcctacatcc tgggaaaaga cattcgctct gagatgagca ccatccggca   3240
gaacctgggg gtctgtcccc agcataacgt gctgtttgac atgctgactg tcgaagaaca   3300
catctggttc tatgcccgct tgaaagggct ctctgagaag cacgtgaagg cggagatgga   3360
gcagatggcc ctggatgttg gtttgccatc aagcaagctg aaaagcaaaa caagccagct   3420
gtcaggtgga atgcagagaa agctatctgt ggccttggcc tttgtcgggg gatctaaggt   3480
tgtcattctg gatgaaccca cagctggtgt ggacccttac tcccgcaggg gaatatggga   3540
gctgctgctg aaataccgac aaggccgcac cattattctc tctacacacc acatggatga   3600
agcggacgtc ctgggggaca ggattgccat catctcccat gggaagctgt gctgtgtggg   3660
ctcctccctg tttctgaaga accagctggg aacaggctac tacctgacct tggtcaagaa   3720
agatgtggaa tcctccctca gttcctgcag aaacagtagt agcactgtgt catacctgaa   3780
aaaggaggac agtgtttctc agagcagttc tgatgctggc ctgggcagcg accatgagag   3840
tgacacgctg accatcgatg tctctgctat ctccaacctc atcaggaagc atgtgtctga   3900
agcccggctg gtggaagaca tagggcatga gctgacctat gtgctgccat atgaagctgc   3960
taaggaggga gcctttgtgg aactctttca tgagattgat gaccggctct cagacctggg   4020
```

-continued

```
catttctagt tatggcatct cagagacgac cctggaagaa atattcctca aggtggccga   4080
agagagtggg gtggatgctg agacctcaga tggtaccttg ccagcaagac gaaacaggcg   4140
ggccttcggg gacaagcaga gctgtcttcg cccgttcact gaagatgatg ctgctgatcc   4200
aaatgattct gacatagacc cagaatccag agagacagac ttgctcagtg ggatggatgg   4260
caaagggtcc taccaggtga aaggctggaa acttacacag caacagtttg tggccctttt   4320
gtggaagaga ctgctaattg ccagacggag tcggaaagga ttttttgctc agattgtctt   4380
gccagctgtg tttgtctgca ttgcccttgt gttcagcctg atcgtgccac cctttggcaa   4440
gtaccccagc ctggaacttc agccctggat gtacaacgaa cagtacacat ttgtcagcaa   4500
tgatgctcct gaggacacgg gaaccctgga actcttaaac gccctcacca aagaccctgg   4560
cttcgggacc cgctgtatgg aaggaaaccc aatcccagac acgccctgcc aggcagggga   4620
ggaagagtgg accactgccc cagttcccca gaccatcatg gacctcttcc agaatgggaa   4680
ctggacaatg cagaaccctt cacctgcatg ccagtgtagc agcgacaaaa tcaagaagat   4740
gctgcctgtg tgtcccccag gggcaggggg gctgcctcct ccacaaagaa aacaaaacac   4800
tgcagatatc cttcaggacc tgacaggaag aaacatttcg gattatctgg tgaagacgta   4860
tgtgcagatc atagccaaaa gcttaaagaa caagatctgg gtgaatgagt ttaggtatgg   4920
cggcttttcc ctgggtgtca gtaatactca agcacttcct ccgagtcaag aagttaatga   4980
tgccatcaaa caaatgaaga aacacctaaa gctggccaag gacagttctg cagatcgatt   5040
tctcaacagc ttgggaagat ttatgacagg actggacacc agaaataatg tcaaggtgtg   5100
gttcaataac aagggctggc atgcaatcag ctctttcctg aatgtcatca acaatgccat   5160
tctccgggcc aacctgcaaa agggagagaa ccctagccat tatggaatta ctgctttcaa   5220
tcatcccctg aatctcacca agcagcagct ctcagaggtg gctctgatga ccacatcagt   5280
ggatgtcctt gtgtccatct gtgtcatctt tgcaatgtcc ttcgtcccag ccagctttgt   5340
cgtattcctg atccaggagc gggtcagcaa agcaaaacac ctgcagttca tcagtggagt   5400
gaagcctgtc atctactggc tctctaattt tgtctgggat atgtgcaatt acgttgtccc   5460
tgccacactg gtcattatca tcttcatctg cttccagcag aagtcctatg tgtcctccac   5520
caatctgcct gtgctagccc ttctactttt gctgtatggg tggtcaatca cacctctcat   5580
gtacccagcc tcctttgtgt tcaagatccc cagcacagcc tatgtggtgc tcaccagcgt   5640
gaacctcttc attggcatta atggcagcgt ggccaccttt gtgctggagc tgttcaccga   5700
caataagctg aataatatca atgatatcct gaagtccgtg ttcttgatct tcccacattt   5760
ttgcctggga cgagggctca tcgacatggt gaaaaaccag gcaatggctg atgccctgga   5820
aaggtttggg gagaatcgct ttgtgtcacc attatcttgg gacttggtgg gacgaaacct   5880
cttcgccatg gccgtggaag gggtggtgtt cttcctcatt actgttctga tccagtacag   5940
attcttcatc aggcccagac ctgtaaatgc aaagctatct cctctgaatg atgaagatga   6000
agatgtgagg cgggaaagac agagaattct tgatggtgga ggccagaatg acatcttaga   6060
aatcaaggag ttgacgaaga tatatagaag gaagcggaag cctgctgttg acaggatttg   6120
cgtgggcatt cctcctggtg agtgctttgg gctcctggga gttaatgggg ctggaaaatc   6180
atcaactttc aagatgttaa caggagatac cactgttacc agaggagatg ctttccttaa   6240
caaaaatagt atcttatcaa acatccatga agtacatcag aacatgggct actgccctca   6300
gtttgatgcc atcacagagc tgttgactgg gagagaacac gtggagttct ttgccctttt   6360
```

-continued

```
gagaggagtc ccagagaaag aagttggcaa ggttggtgag tgggcgattc ggaaactggg   6420
cctcgtgaag tatggagaaa aatatgctgg taactatagt ggaggcaaca aacgcaagct   6480
ctctacagcc atggctttga tcggcgggcc tcctgtggtg tttctggatg aacccaccac   6540
aggcatggat cccaaagccc ggcggttctt gtggaattgt gccctaagtg ttgtcaagga   6600
ggggagatca gtagtgctta catctcatag tatggaagaa tgtgaagctc tttgcactag   6660
gatggcaatc atggtcaatg gaaggttcag gtgccttggc agtgtccagc atctaaaaaa   6720
taggtttgga gatggttata caatagttgt acgaatagca gggtccaacc cggacctgaa   6780
gcctgtccag gatttctttg gacttgcatt tcctggaagt gttctaaaag agaaacaccg   6840
gaacatgcta caataccagc ttccatcttc attatcttct ctggccagga tattcagcat   6900
cctctcccag agcaaaaagc gactccacat agaagactac tctgtttctc agacaacact   6960
tgaccaagta tttgtgaact ttgccaagga ccaaagtgat gatgaccact taaaagacct   7020
ctcattacac aaaaaccaga cagtagtgga cgttgcagtt ctcacatctt ttctacagga   7080
tgagaaagtg aaagaaagct atgtatgaag aatcctgttc atacggggtg gctgaaagta   7140
aagaggaact agactttcct ttgcaccatg tgaagtgttg tggagaaaag agccagaagt   7200
tgatgtggga agaagtaaac tggatactgt actgatacta ttcaatgcaa tgcaattcaa   7260
tgcaatgaaa acaaaattcc attacagggg cagtgccttt gtagcctatg tcttgtatgg   7320
ctctcaagtg aaagacttga atttagtttt ttacctatac ctatgtgaaa ctctattatg   7380
gaacccaatg gacatatggg tttgaactca cacttttttt tttttttgt tcctgtgtat   7440
tctcattggg gttgcaacaa taattcatca agtaatcatg gccagcgatt attgatcaaa   7500
atcaaaaggt aatgcacatc ctcattcact aagccatgcc atgcccagga gactggtttc   7560
ccggtgacac atccattgct ggcaatgagt gtgccagagt tattagtgcc aagtttttca   7620
gaaagtttga agcaccatgg tgtgtcatgc tcacttttgt gaaagctgct ctgctcagag   7680
tctatcaaca ttgaatatca gttgacagaa tggtgccatg cgtggctaac atcctgcttt   7740
gattccctct gataagctgt tctggtggca gtaacatgca acaaaaatgt gggtgtctct   7800
aggcacggga aacttggttc cattgttata ttgtcctatg cttcgagcca tgggtctaca   7860
gggtcatcct tatgagactc ttaaatatac ttagatcctg gtaagaggca aagaatcaac   7920
agccaaactg ctggggctgc aagctgctga agccagggca tgggattaaa gagattgtgc   7980
gttcaaacct agggaagcct gtgcccattt gtcctgactg tctgctaaca tggtacactg   8040
catctcaaga tgtttatctg acacaagtgt attatttctg gctttttgaa ttaatctaga   8100
aaatgaaaag atggagttgt attttgacaa aaatgtttgt actttttaat gttatttgga   8160
attttaagtt ctatcagtga cttctgaatc cttagaatgg cctctttgta gaaccctgtg   8220
gtatagagga gtatggccac tgccccacta tttttatttt cttatgtaag tttgcatatc   8280
agtcatgact agtgcctaga aagcaatgtg atggtcagga tctcatgaca ttatatttga   8340
gtttctttca gatcatttag gatactctta atctcacttc atcaatcaaa tattttttga   8400
gtgtatgctg tagctgaaag agtatgtacg tacgtataag actagagaga tattaagtct   8460
cagtacactt cctgtgccat gttattcagc tcactggttt acaaatatag gttgtcttgt   8520
ggttgtagga gcccactgta acaatattgg gcagcctttt tttttttttt ttaattgcaa   8580
caatgcaaaa gccaagaaag tataagggtc acaagtttaa acaatgaatt cttcaacagg   8640
gaaaacagct agcttgaaaa cttgctgaaa aacacaactt gtgtttatgg catttagtac   8700
cttcaaataa ttggctttgc agatattgga taccccatta aatctgacag tctcaaattt   8760
```

-continued

```
ttcatctctt caatcactag tcaagaaaaa tataaaaaca acaaatactt ccatatggag   8820

catttttcag agttttctaa cccagtctta tttttctagt cagtaaacat ttgtaaaaat   8880

actgtttcac taatacttac tgttaactgt cttgagagaa aagaaaaata tgagagaact   8940

attgtttggg gaagttcaag tgatctttca atatcattac taacttcttc cactttttcc   9000

aaaatttgaa tattaacgct aaaggtgtaa gacttcagat ttcaaattaa tctttctata   9060

tttttaaat ttacagaata ttatataacc cactgctgaa aaagaaaaaa atgattgttt   9120

tagaagttaa agtcaatatt gattttaaat ataagtaatg aaggcatatt tccaataact   9180

agtgatatgg catcgttgca atttacagta tcttcaaaaa tacagaattt atagaataat   9240

ttctcctcat ttaatatttt tcaaaatcaa agttatggtt tcctcatttt actaaaatcg   9300

tattctaatt cttcattata gtaaatctat gagcaactcc ttacttcggt tcctctgatt   9360

tcaaggccat attttaaaaa atcaaaaggc actgtgaact attttgaaga aaacacgaca   9420

ttttaataca gattgaaagg acctcttctg aagctagaaa caatctatag ttatacatct   9480

tcattaatac tgtgttacct tttaaaatag taattttta cattttcctg tgtaaaccta   9540

attgtggtag aaatttttac caactctata ctcaatcaag caaaatttct gtatattccc   9600

tgtggaatgt acctatgtga gtttcagaaa ttctcaaaat acgtgttcaa aaatttctgc   9660

ttttgcatct ttgggacacc tcagaaaact tattaacaac tgtgaatatg agaaatacag   9720

aagaaaataa taagccctct atacataaat gcccagcaca attcattgtt aaaaaacaac   9780

caaacctcac actactgtat ttcattatct gtactgaaag caaatgcttt gtgactatta   9840

aatgttgcac atcattcatt cactgtatag taatcattga ctaaagccat ttgctgtgtt   9900

ttcttcttgt ggntgnatat atcaggtaaa atattttcca aagagccatg tgtcatgtaa   9960

tactgaaccc tttgatattg agacattaat ttggaccctt ggtattatct actagaataa  10020

tgtaatactg nagaaatatt gctctaattc tttcaaaatg gtgcatcccc cttaaaangt  10080

tctatttcca taaggattta gcttgcttat cccttcttat accctaagat gaagctgttt  10140

ttgtgctctt tgttcatcat tggccctcat tccaagcact ttacgctgtc tgtaatggga  10200

tctatttttg cactggaata tctgagaatt gcaaaactag acaaaagttt cacaacagat  10260

ttctaagtta aatcattttc attaaaagga aaaaagaaaa aaaattttgt atgtcaataa  10320

ctttatatga agtattaaaa tgcatatttc tatgttgtaa tataatgagt cacaaaataa  10380

agctgtgaca gttctgttaa aaaaaaaaaa aaaaaaaaaa aaaaaaaaaa aaaaaaaaaa  10440

aaaaaaaaaa aaaaaaaaaa aaaaaaaaaa aaaa                              10474


<210> SEQ ID NO 10
<211> LENGTH: 2261
<212> TYPE: PRT
<213> ORGANISM: Homo sapiens

<400> SEQUENCE: 10

Met Ala Cys Trp Pro Gln Leu Arg Leu Leu Leu Trp Lys Asn Leu Thr
  1               5                  10                  15

Phe Arg Arg Arg Gln Thr Cys Gln Leu Leu Leu Glu Val Ala Trp Pro
             20                  25                  30

Leu Phe Ile Phe Leu Ile Leu Ile Ser Val Arg Leu Ser Tyr Pro Pro
         35                  40                  45

Tyr Glu Gln His Glu Cys His Phe Pro Asn Lys Ala Met Pro Ser Ala
     50                  55                  60
```

-continued

```
Gly Thr Leu Pro Trp Val Gln Gly Ile Ile Cys Asn Ala Asn Asn Pro
 65                  70                  75                  80

Cys Phe Arg Tyr Pro Thr Pro Gly Glu Ala Pro Gly Val Val Gly Asn
                 85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Ser Asn Leu Lys Leu
    130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
        195                 200                 205

Gln Glu Val Ser Glu Leu Cys Gly Leu Pro Lys Glu Lys Leu Ala Ala
    210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
            260                 265                 270

Phe Ser Met Arg Ser Trp Ser Asp Met Arg Gln Glu Val Met Phe Leu
        275                 280                 285

Thr Asn Val Asn Ser Ser Ser Ser Ser Thr Gln Ile Tyr Gln Ala Val
    290                 295                 300

Ser Arg Ile Val Cys Gly His Pro Glu Gly Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
        435                 440                 445

Trp Glu Gln Gln Leu Asp Gly Leu Asp Trp Thr Ala Gln Asp Ile Val
    450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
```

-continued

```
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
        515                 520                 525

Glu Arg Lys Phe Trp Ala Gly Ile Val Phe Thr Gly Ile Thr Pro Gly
    530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Trp Tyr Val Trp Gly Gly
            580                 585                 590

Phe Ala Tyr Leu Gln Asp Val Val Glu Gln Ala Ile Ile Arg Val Leu
        595                 600                 605

Thr Gly Thr Glu Lys Lys Thr Gly Val Tyr Met Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Ile Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ser Asp Glu Lys Ser His Pro Gly Ser Asn Gln
865                 870                 875                 880

Lys Arg Met Ser Glu Ile Cys Met Glu Glu Glu Pro Thr His Leu Lys
                885                 890                 895

Leu Gly Val Ser Ile Gln Asn Leu Val Lys Val Tyr Arg Asp Gly Met
            900                 905                 910
```

-continued

```
Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                 1000                1005

Lys Ala Glu Met Glu Gln Met Ala Leu Asp Val Gly Leu Pro Ser Ser
    1010                1015                1020

Lys Leu Lys Ser Lys Thr Ser Gln Leu Ser Gly Gly Met Gln Arg Lys
1025                1030                1035                1040

Leu Ser Val Ala Leu Ala Phe Val Gly Gly Ser Lys Val Val Ile Leu
                1045                1050                1055

Asp Glu Pro Thr Ala Gly Val Asp Pro Tyr Ser Arg Arg Gly Ile Trp
            1060                1065                1070

Glu Leu Leu Leu Lys Tyr Arg Gln Gly Arg Thr Ile Ile Leu Ser Thr
        1075                1080                1085

His His Met Asp Glu Ala Asp Val Leu Gly Asp Arg Ile Ala Ile Ile
    1090                1095                1100

Ser His Gly Lys Leu Cys Cys Val Gly Ser Ser Leu Phe Leu Lys Asn
1105                1110                1115                1120

Gln Leu Gly Thr Gly Tyr Tyr Leu Thr Leu Val Lys Lys Asp Val Glu
                1125                1130                1135

Ser Ser Leu Ser Ser Cys Arg Asn Ser Ser Ser Thr Val Ser Tyr Leu
            1140                1145                1150

Lys Lys Glu Asp Ser Val Ser Gln Ser Ser Ser Asp Ala Gly Leu Gly
        1155                1160                1165

Ser Asp His Glu Ser Asp Thr Leu Thr Ile Asp Val Ser Ala Ile Ser
    1170                1175                1180

Asn Leu Ile Arg Lys His Val Ser Glu Ala Arg Leu Val Glu Asp Ile
1185                1190                1195                1200

Gly His Glu Leu Thr Tyr Val Leu Pro Tyr Glu Ala Ala Lys Glu Gly
                1205                1210                1215

Ala Phe Val Glu Leu Phe His Glu Ile Asp Asp Arg Leu Ser Asp Leu
            1220                1225                1230

Gly Ile Ser Ser Tyr Gly Ile Ser Glu Thr Thr Leu Glu Glu Ile Phe
        1235                1240                1245

Leu Lys Val Ala Glu Glu Ser Gly Val Asp Ala Glu Thr Ser Asp Gly
    1250                1255                1260

Thr Leu Pro Ala Arg Arg Asn Arg Arg Ala Phe Gly Asp Lys Gln Ser
1265                1270                1275                1280

Cys Leu Arg Pro Phe Thr Glu Asp Asp Ala Ala Asp Pro Asn Asp Ser
                1285                1290                1295

Asp Ile Asp Pro Glu Ser Arg Glu Thr Asp Leu Leu Ser Gly Met Asp
            1300                1305                1310

Gly Lys Gly Ser Tyr Gln Val Lys Gly Trp Lys Leu Thr Gln Gln Gln
        1315                1320                1325
```

-continued

```
Phe Val Ala Leu Leu Trp Lys Arg Leu Leu Ile Ala Arg Arg Ser Arg
    1330                1335                1340

Lys Gly Phe Phe Ala Gln Ile Val Leu Pro Ala Val Phe Val Cys Ile
1345                1350                1355                1360

Ala Leu Val Phe Ser Leu Ile Val Pro Pro Phe Gly Lys Tyr Pro Ser
                1365                1370                1375

Leu Glu Leu Gln Pro Trp Met Tyr Asn Glu Gln Tyr Thr Phe Val Ser
            1380                1385                1390

Asn Asp Ala Pro Glu Asp Thr Gly Thr Leu Glu Leu Leu Asn Ala Leu
        1395                1400                1405

Thr Lys Asp Pro Gly Phe Gly Thr Arg Cys Met Glu Gly Asn Pro Ile
    1410                1415                1420

Pro Asp Thr Pro Cys Gln Ala Gly Glu Glu Glu Trp Thr Thr Ala Pro
1425                1430                1435                1440

Val Pro Gln Thr Ile Met Asp Leu Phe Gln Asn Gly Asn Trp Thr Met
                1445                1450                1455

Gln Asn Pro Ser Pro Ala Cys Gln Cys Ser Ser Asp Lys Ile Lys Lys
            1460                1465                1470

Met Leu Pro Val Cys Pro Pro Gly Ala Gly Gly Leu Pro Pro Pro Gln
        1475                1480                1485

Arg Lys Gln Asn Thr Ala Asp Ile Leu Gln Asp Leu Thr Gly Arg Asn
    1490                1495                1500

Ile Ser Asp Tyr Leu Val Lys Thr Tyr Val Gln Ile Ile Ala Lys Ser
1505                1510                1515                1520

Leu Lys Asn Lys Ile Trp Val Asn Glu Phe Arg Tyr Gly Gly Phe Ser
                1525                1530                1535

Leu Gly Val Ser Asn Thr Gln Ala Leu Pro Pro Ser Gln Glu Val Asn
            1540                1545                1550

Asp Ala Ile Lys Gln Met Lys Lys His Leu Lys Leu Ala Lys Asp Ser
        1555                1560                1565

Ser Ala Asp Arg Phe Leu Asn Ser Leu Gly Arg Phe Met Thr Gly Leu
    1570                1575                1580

Asp Thr Arg Asn Asn Val Lys Val Trp Phe Asn Asn Lys Gly Trp His
1585                1590                1595                1600

Ala Ile Ser Ser Phe Leu Asn Val Ile Asn Asn Ala Ile Leu Arg Ala
                1605                1610                1615

Asn Leu Gln Lys Gly Glu Asn Pro Ser His Tyr Gly Ile Thr Ala Phe
            1620                1625                1630

Asn His Pro Leu Asn Leu Thr Lys Gln Gln Leu Ser Glu Val Ala Leu
        1635                1640                1645

Met Thr Thr Ser Val Asp Val Leu Val Ser Ile Cys Val Ile Phe Ala
    1650                1655                1660

Met Ser Phe Val Pro Ala Ser Phe Val Val Phe Leu Ile Gln Glu Arg
1665                1670                1675                1680

Val Ser Lys Ala Lys His Leu Gln Phe Ile Ser Gly Val Lys Pro Val
                1685                1690                1695

Ile Tyr Trp Leu Ser Asn Phe Val Trp Asp Met Cys Asn Tyr Val Val
            1700                1705                1710

Pro Ala Thr Leu Val Ile Ile Ile Phe Ile Cys Phe Gln Gln Lys Ser
        1715                1720                1725

Tyr Val Ser Ser Thr Asn Leu Pro Val Leu Ala Leu Leu Leu Leu Leu
    1730                1735                1740

Tyr Gly Trp Ser Ile Thr Pro Leu Met Tyr Pro Ala Ser Phe Val Phe
```

-continued

```
1745                1750                1755                1760

Lys Ile Pro Ser Thr Ala Tyr Val Val Leu Thr Ser Val Asn Leu Phe
                1765                1770                1775

Ile Gly Ile Asn Gly Ser Val Ala Thr Phe Val Leu Glu Leu Phe Thr
            1780                1785                1790

Asp Asn Lys Leu Asn Asn Ile Asn Asp Ile Leu Lys Ser Val Phe Leu
        1795                1800                1805

Ile Phe Pro His Phe Cys Leu Gly Arg Gly Leu Ile Asp Met Val Lys
    1810                1815                1820

Asn Gln Ala Met Ala Asp Ala Leu Glu Arg Phe Gly Glu Asn Arg Phe
1825                1830                1835                1840

Val Ser Pro Leu Ser Trp Asp Leu Val Gly Arg Asn Leu Phe Ala Met
                1845                1850                1855

Ala Val Glu Gly Val Val Phe Phe Leu Ile Thr Val Leu Ile Gln Tyr
            1860                1865                1870

Arg Phe Phe Ile Arg Pro Arg Pro Val Asn Ala Lys Leu Ser Pro Leu
        1875                1880                1885

Asn Asp Glu Asp Glu Asp Val Arg Arg Glu Arg Gln Arg Ile Leu Asp
    1890                1895                1900

Gly Gly Gly Gln Asn Asp Ile Leu Glu Ile Lys Glu Leu Thr Lys Ile
1905                1910                1915                1920

Tyr Arg Arg Lys Arg Lys Pro Ala Val Asp Arg Ile Cys Val Gly Ile
                1925                1930                1935

Pro Pro Gly Glu Cys Phe Gly Leu Leu Gly Val Asn Gly Ala Gly Lys
            1940                1945                1950

Ser Ser Thr Phe Lys Met Leu Thr Gly Asp Thr Thr Val Thr Arg Gly
        1955                1960                1965

Asp Ala Phe Leu Asn Lys Asn Ser Ile Leu Ser Asn Ile His Glu Val
    1970                1975                1980

His Gln Asn Met Gly Tyr Cys Pro Gln Phe Asp Ala Ile Thr Glu Leu
1985                1990                1995                2000

Leu Thr Gly Arg Glu His Val Glu Phe Phe Ala Leu Leu Arg Gly Val
                2005                2010                2015

Pro Glu Lys Glu Val Gly Lys Val Gly Glu Trp Ala Ile Arg Lys Leu
            2020                2025                2030

Gly Leu Val Lys Tyr Gly Glu Lys Tyr Ala Gly Asn Tyr Ser Gly Gly
        2035                2040                2045

Asn Lys Arg Lys Leu Ser Thr Ala Met Ala Leu Ile Gly Gly Pro Pro
    2050                2055                2060

Val Val Phe Leu Asp Glu Pro Thr Thr Gly Met Asp Pro Lys Ala Arg
2065                2070                2075                2080

Arg Phe Leu Trp Asn Cys Ala Leu Ser Val Val Lys Glu Gly Arg Ser
                2085                2090                2095

Val Val Leu Thr Ser His Ser Met Glu Glu Cys Glu Ala Leu Cys Thr
            2100                2105                2110

Arg Met Ala Ile Met Val Asn Gly Arg Phe Arg Cys Leu Gly Ser Val
        2115                2120                2125

Gln His Leu Lys Asn Arg Phe Gly Asp Gly Tyr Thr Ile Val Val Arg
    2130                2135                2140

Ile Ala Gly Ser Asn Pro Asp Leu Lys Pro Val Gln Asp Phe Phe Gly
2145                2150                2155                2160

Leu Ala Phe Pro Gly Ser Val Leu Lys Glu Lys His Arg Asn Met Leu
                2165                2170                2175
```

-continued

```
Gln Tyr Gln Leu Pro Ser Ser Leu Ser Ser Leu Ala Arg Ile Phe Ser
            2180                2185                2190

Ile Leu Ser Gln Ser Lys Lys Arg Leu His Ile Glu Asp Tyr Ser Val
        2195                2200                2205

Ser Gln Thr Thr Leu Asp Gln Val Phe Val Asn Phe Ala Lys Asp Gln
    2210                2215                2220

Ser Asp Asp Asp His Leu Lys Asp Leu Ser Leu His Lys Asn Gln Thr
2225                2230                2235                2240

Val Val Asp Val Ala Val Leu Thr Ser Phe Leu Gln Asp Glu Lys Val
                2245                2250                2255

Lys Glu Ser Tyr Val
            2260
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: ABC1 amplification primer

<400> SEQUENCE: 11
cctctcatta cacaaaaacc agac 24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: ABC1 amplification primer

<400> SEQUENCE: 12
gctttctttc acttctcatc ctg 23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: ABC1 RT-PCR primer

<400> SEQUENCE: 13
tccttgggtt caggggatta tc 22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: ABC1 RT-PCR primer

<400> SEQUENCE: 14
caatgttttt gtggcttcgg c 21

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: ABC1 RT-PCR primer -continued

<400> SEQUENCE: 15
agtcgagctc caaacatgtc agctgttact ggaagtggcc 40

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: ABC1 RT-PCR
primer

<400> SEQUENCE: 16
tctctggatt ctgggtctat gtcag 25

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: ABC1 RT-PCR
primer

<400> SEQUENCE: 17
gggagccttt gtggaactct ttc 23

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: ABC1 RT-PCR
primer

<400> SEQUENCE: 18
actggtcgac cattgaattg cattgcattg aatagtatca g 41

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 19
tttcctggtg gacaatgaa 19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 20
agtgacatgc gacaggag 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer -continued

<400> SEQUENCE: 21
gatctggaag gcatgtgg 18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 22
ccaggcagca ttgagctg 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 23
ggcctggaca acagcata 18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 24
ggacaacctg tttgagagt 19

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 25
aagacgacca ccatgtca 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 26
atatgggagc tgctgctg 18

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 27

-continued

```
gggcatgagc tgacctatgt gctg                                          24


<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 28

aagagactgc taattgcc                                                 18


<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 29

agcgacaaaa tcaagaag                                                 18


<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 30

tggcatgcaa tcagctct                                                 18


<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 31

tcctccacca atctgcct                                                 18


<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 32

ttcttcctca ttactgtt                                                 18


<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: ABC1
      sequencing primer

<400> SEQUENCE: 33
```

-continued gatgccatca cagagctg 18

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 34
agtgtccagc atctaaa 17

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 35
caaagttcac aaatactt 18

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 36
cttagggcac aattccaca 19

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 37
tgaaagttga tgattttc 18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 38
tttttcacca tgtcgatga 19

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 39
ctccactgat gaactgc 17

-continued

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 40
gtttcttcat ttgtttga 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 41
agggcgtgtc tgggattg 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 42
cagaatcatt tggatcag 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 43
catcagaact gctctgag 18

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 44
agctggcttg ttttgcttt 19

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: ABC1
sequencing primer

<400> SEQUENCE: 45
tggacacgcc cagcttca 18

-continued

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 46
cctgccatgc cacacaca 18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 47
ctcatcaccc gcagaaag 18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 48
cacactccat gaagcgag 18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 49
tccagataat gcgggaaa 18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 50
tcaggattgg cttcagga 18

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: ABC1 sequencing primer

<400> SEQUENCE: 51
aagtttgagc tggatttctt g 21

-continued

```
<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: beta-globin
      antisense oligonucleotide

<400> SEQUENCE: 52

cctcttacct cagttacaat ttata                                           25


<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: ABC1
      antisense oligonucleotide

<400> SEQUENCE: 53

catgttgttc atagggtggg tagctc                                          26


<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: beta-actin
      amplification primer

<400> SEQUENCE: 54

tcacccacac tgtgccatct acga                                            24


<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: beta-actin
      amplification primer

<400> SEQUENCE: 55

cagcggaacc gctcattgcc aatgg                                           25


<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: sterol
      response element oligonucleotide

<400> SEQUENCE: 56

tcgagtgacc gatagtaacc tctcga                                          26


<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: mutated
      sterol response element oligonucleotide

<400> SEQUENCE: 57

tcgagctgca catagtaacc tctcga                                          26
```